US008900553B2

(12) United States Patent
Tamarkin et al.

(10) Patent No.: US 8,900,553 B2
(45) Date of Patent: *Dec. 2, 2014

(54) OIL AND LIQUID SILICONE FOAMABLE CARRIERS AND FORMULATIONS

(75) Inventors: Dov Tamarkin, Ness Ziona (IL); Helena Shifrin, Rehovot (IL); Rita Keynan, Rehovot (IL); Enbal Ziv, Gedera (IL); Tal Berman, Rishon Lezion (IL); David Schuz, Moshav Gimzu (IL); Elana Gazal, Rehovot (IL)

(73) Assignee: Foamix Pharmaceuticals Ltd., Rehovot (IL)

( * ) Notice: Subject to any disclaimer, the term of this patent is extended or adjusted under 35 U.S.C. 154(b) by 129 days.

This patent is subject to a terminal disclaimer.

(21) Appl. No.: 12/795,213

(22) Filed: Jun. 7, 2010

(65) Prior Publication Data

US 2011/0212033 A1    Sep. 1, 2011

Related U.S. Application Data

(63) Continuation of application No. PCT/IB2008/003939, filed on Dec. 8, 2008.

(60) Provisional application No. 61/012,414, filed on Dec. 7, 2007, provisional application No. 61/103,500, filed on Oct. 7, 2008.

(51) Int. Cl.
| A61K 9/12 | (2006.01) |
| A61K 8/04 | (2006.01) |
| A61K 9/00 | (2006.01) |
| A61K 31/65 | (2006.01) |
| A61K 47/06 | (2006.01) |
| A61K 47/14 | (2006.01) |
| A61K 47/24 | (2006.01) |

(52) U.S. Cl.
CPC ............. *A61K 9/122* (2013.01); *A61K 9/0014* (2013.01); *A61K 31/65* (2013.01); *A61K 47/06* (2013.01); *A61K 47/14* (2013.01); *A61K 47/24* (2013.01); *A61K 8/046* (2013.01); *Y10S 514/871* (2013.01); *Y10S 514/945* (2013.01)
USPC ........... 424/43; 424/78.07; 514/871; 514/945

(58) Field of Classification Search
CPC ....... A61K 31/65; A61K 47/06; A61K 47/14; A61K 47/24; A61K 8/046
USPC .......................... 424/43, 78.07; 514/871, 945
See application file for complete search history.

(56) References Cited

U.S. PATENT DOCUMENTS

| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |

(Continued)

FOREIGN PATENT DOCUMENTS

| AU | 198780257 | 9/1986 |
| AU | 782515 | 12/2005 |

(Continued)

OTHER PUBLICATIONS

"HLB Systems", http://pharmcal.tripod.com/ch17.htm, Accessed Sep. 17, 2010, pp. 1-3.
Adachi, Shuji. "Storage and Oxidative Stability of O/W/ Nano-emulsions." Foods Food Ingredients. J. Jpn. vol. 209, No. 11. 2004. 1 page.
Alcohol SDA 40B.http://www.pharmco-prod.com/pages/MSDS/SDA.sub.--40B.sub.--200.pdf Accessed Dec. 9, 2008, 2 pages.
Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds,"Antimicrobial Agents and Chemotherapy, vol. 35, No. 9, pp. 1799-1803, 1991.

(Continued)

*Primary Examiner* — Mina Haghighatian
(74) *Attorney, Agent, or Firm* — Fish & Richardson P.C.

(57) ABSTRACT

A waterless foamable pharmaceutical composition suitable for external administration is disclosed. The composition includes a foamable carrier least one liquefied or compressed gas propellant. The foamable carrier includes at least one liquid oil; at least one silicone and at least one least one stabilizing agent; wherein the stabilizing agent selected from the group consisting of about 0.01% to about 25% by weight of at least one surface-active agent alone or on combination with a foam adjuvant; and about 0% to about 5% by weight of at least one polymeric agent alone or on combination with a foam adjuvant; and mixtures thereof. Pharmaceutical compositions comprising active agents, methods for their preparation, propellants suitable for use with the carriers and uses thereof are further described.

23 Claims, 1 Drawing Sheet

(56) References Cited

U.S. PATENT DOCUMENTS

| | | |
|---|---|---|
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki et al. |
| 3,563,098 A | 2/1971 | Weber, III |
| 3,574,821 A | 4/1971 | Pfirrmann and Geitlich |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |

(56) References Cited

U.S. PATENT DOCUMENTS

| | | |
|---|---|---|
| 4,981,677 A | 1/1991 | Thau |
| 4,981,679 A | 1/1991 | Briggs et al. |
| 4,981,845 A | 1/1991 | Pereira |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,700,396 A | 12/1997 | Suzuki et al. |
| 5,716,611 A | 2/1998 | Oshlack et al. |
| 5,716,621 A | 2/1998 | Bello et al. |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |

(56) References Cited

U.S. PATENT DOCUMENTS

| | | |
|---|---|---|
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,261,544 B1 | 7/2001 | Coury et al. |
| 6,270,781 B1 | 8/2001 | Gehlsen |
| 6,271,295 B1 | 8/2001 | Powell et al. |
| 6,274,150 B1 | 8/2001 | Simonnet et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,532 B1 | 11/2002 | Kamimura et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |

(56) References Cited

U.S. PATENT DOCUMENTS

| | | |
|---|---|---|
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin |
| 6,911,211 B2 | 6/2005 | Eini et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2* | 8/2009 | Tamarkin et al. ............... 424/43 |
| 7,645,803 B2 | 1/2010 | Tamarkin et al. |
| 7,654,415 B2 | 2/2010 | van der Heijden |
| 7,682,523 B2 | 3/2010 | Weisman et al. |
| 7,682,623 B2 | 3/2010 | Eini et al. |
| 7,700,076 B2 | 4/2010 | Tamarkin et al. |
| 7,704,518 B2* | 4/2010 | Tamarkin et al. ............. 424/405 |
| 7,758,888 B2 | 7/2010 | Lapidot et al. |
| 7,793,807 B2 | 9/2010 | Goujon et al. |
| 7,820,145 B2* | 10/2010 | Tamarkin et al. ............... 424/45 |
| 7,960,416 B2 | 6/2011 | Sato et al. |
| 8,114,385 B2 | 2/2012 | Tamarkin et al. |
| 8,158,109 B2 | 4/2012 | Abram et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,375 B2 | 7/2013 | Tamarkin et al. |
| 8,518,376 B2 | 8/2013 | Tamarkin et al. |
| 8,618,081 B2 | 12/2013 | Tamarkin et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0036450 A1 | 11/2001 | Verite et al. |
| 2001/0054574 A1 | 12/2001 | Navarro |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Haslwanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0122811 A1 | 9/2002 | Stein et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0078172 A1 | 4/2003 | Guiramand et al. |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215472 A1 | 11/2003 | Bonda et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |

(56) References Cited

U.S. PATENT DOCUMENTS

| | | |
|---|---|---|
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0258628 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 * | 2/2005 | Tamarkin et al. ............... 424/45 |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0014990 A1 | 1/2006 | Kuechler et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0224143 A1 | 9/2007 | Konis et al. |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0053290 A1 | 2/2009 | Sand et al. |
| 2009/0068118 A1 | 3/2009 | Eini et al. |
| 2009/0093514 A1 | 4/2009 | Statham et al. |

(56) References Cited

U.S. PATENT DOCUMENTS

| | | |
|---|---|---|
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0137198 A1 | 6/2010 | Eini et al. |
| 2010/0221194 A1 | 9/2010 | Loupenok |
| 2010/0221195 A1 | 9/2010 | Tamarkin et al. |
| 2010/0266510 A1 | 10/2010 | Tamarkin et al. |
| 2011/0002857 A1 | 1/2011 | Tamarkin et al. |
| 2011/0002969 A1 | 1/2011 | Serraima et al. |
| 2011/0008266 A1 | 1/2011 | Tamarkin et al. |
| 2011/0045037 A1 | 2/2011 | Tamarkin et al. |
| 2011/0097279 A1 | 4/2011 | Tamarkin et al. |
| 2011/0212033 A1 | 9/2011 | Tamarkin et al. |
| 2011/0268665 A1 | 11/2011 | Tamarkin et al. |
| 2012/0064136 A1 | 3/2012 | Baker, Jr. et al. |
| 2012/0087872 A1 | 4/2012 | Tamarkin et al. |
| 2012/0128598 A1 | 5/2012 | Trumbore et al. |
| 2012/0148503 A1 | 6/2012 | Tamarkin et al. |
| 2012/0156144 A1 | 6/2012 | Tamarkin et al. |
| 2012/0195836 A1 | 8/2012 | Tamarkin et al. |
| 2012/0213709 A1 | 8/2012 | Tamarkin et al. |
| 2012/0213710 A1 | 8/2012 | Tamarkin et al. |
| 2012/0237453 A1 | 9/2012 | Tamarkin et al. |
| 2013/0011342 A1 | 1/2013 | Tamarkin et al. |
| 2013/0028850 A1 | 1/2013 | Tamarkin et al. |
| 2013/0053353 A1 | 2/2013 | Tamarkin et al. |
| 2013/0064777 A1 | 3/2013 | Tamarkin et al. |
| 2013/0161351 A1 | 6/2013 | Eini et al. |
| 2013/0164225 A1 | 6/2013 | Tamarkin et al. |
| 2013/0183250 A1 | 7/2013 | Friedman et al. |
| 2013/0183251 A1 | 7/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0189196 A1 | 7/2013 | Tamarkin et al. |
| 2013/0195769 A1 | 8/2013 | Tamarkin et al. |
| 2013/0225536 A1 | 8/2013 | Tamarkin et al. |
| 2013/0295022 A1 | 11/2013 | Friedman et al. |
| 2014/0050673 A1 | 2/2014 | Tamarkin et al. |

FOREIGN PATENT DOCUMENTS

| | | |
|---|---|---|
| AU | 2010219295 | 9/2012 |
| CA | 2154438 | 1/1996 |
| CA | 2422244 | 9/2003 |
| CA | 2502986 | 8/2011 |
| CA | 2534372 | 1/2012 |
| CA | 2536482 | 7/2012 |
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 A1 | 2/2003 |
| DE | 102004016710 | 10/2005 |
| DE | 2 608 226 | 9/2007 |
| EP | 0156507 A1 | 10/1985 |
| EP | 0186453 A2 | 7/1986 |
| EP | 211550 | 2/1987 |
| EP | 0214865 A2 | 3/1987 |
| EP | 0216856 | 4/1987 |
| EP | 0270316 | 6/1988 |
| EP | 297436 A2 | 1/1989 |
| EP | 326196 | 8/1989 |
| EP | 336812 | 10/1989 |
| EP | 0391124 A2 | 10/1990 |
| EP | 0404376 | 12/1990 |
| EP | 414920 | 3/1991 |
| EP | 0484530 A1 | 5/1992 |
| EP | 485299 | 5/1992 |
| EP | 0488089 A1 | 6/1992 |
| EP | 504301 | 9/1992 |
| EP | 0506197 A1 | 9/1992 |
| EP | 0 528 190 | 2/1993 |
| EP | 0535327 A1 | 4/1993 |
| EP | 0 552 612 | 7/1993 |
| EP | 0569773 A2 | 11/1993 |
| EP | 0598412 A2 | 5/1994 |
| EP | 0 662 431 | 7/1995 |
| EP | 0676198 | 10/1995 |
| EP | 0 738 516 | 10/1996 |
| EP | 0 757 959 | 2/1997 |
| EP | 0824911 | 2/1998 |
| EP | 829259 | 3/1998 |
| EP | 928608 | 7/1999 |
| EP | 0979654 A1 | 2/2000 |
| EP | 0993827 A1 | 4/2000 |
| EP | 1025836 A1 | 8/2000 |
| EP | 1055425 A2 | 11/2000 |
| EP | 1215258 | 6/2002 |
| EP | 1287813 | 3/2003 |
| EP | 1308169 | 5/2003 |
| EP | 1 375 386 | 1/2004 |
| EP | 1428521 | 6/2004 |
| EP | 1438946 | 7/2004 |
| EP | 1189579 | 9/2004 |
| EP | 1475381 | 11/2004 |
| EP | 1483001 | 12/2004 |
| EP | 1500385 | 1/2005 |
| EP | 1 537 916 | 6/2005 |
| EP | 1600185 | 11/2005 |
| EP | 1734927 | 12/2006 |
| EP | 1758547 | 3/2007 |
| EP | 1584324 | 11/2007 |
| EP | 1889609 | 2/2008 |
| EP | 2422768 | 2/2012 |
| EP | 2494959 | 9/2012 |
| FR | 2 591 331 | 6/1987 |
| FR | 2 640 942 | 6/1990 |
| FR | 2736824 | 1/1997 |
| FR | 2774595 A | 8/1999 |
| FR | 2 789 371 | 8/2000 |
| FR | 2 793 479 | 11/2000 |
| FR | 2 814 959 | 4/2002 |
| FR | 2 833 246 | 6/2003 |
| FR | 2840903 | 12/2003 |
| FR | 2 843 373 | 2/2004 |
| FR | 2 845 672 | 4/2004 |
| FR | 2 848 998 | 6/2004 |
| FR | 2860976 | 4/2005 |
| FR | 2915891 | 11/2008 |
| GB | 808104 | 1/1959 |
| GB | 808105 A | 1/1959 |
| GB | 922930 | 4/1963 |
| GB | 933486 A | 8/1963 |
| GB | 998 490 | 7/1965 |
| GB | 1026831 | 4/1966 |
| GB | 1033299 | 6/1966 |
| GB | 1081949 A | 9/1967 |
| GB | 1121358 | 7/1968 |
| GB | 1 162 684 | 8/1969 |
| GB | 1170152 A | 11/1969 |
| GB | 1 201 918 | 8/1970 |
| GB | 1347950 | 2/1974 |
| GB | 1 351 761 | 5/1974 |
| GB | 1 351 762 | 5/1974 |
| GB | 1 353 381 | 5/1974 |
| GB | 1376649 | 12/1974 |
| GB | 1397285 | 6/1975 |
| GB | 1408036 | 10/1975 |
| GB | 1 457 671 | 12/1976 |
| GB | 1489672 A | 10/1977 |
| GB | 2004746 A | 4/1979 |
| GB | 1561423 | 2/1980 |
| GB | 2114580 | 8/1983 |
| GB | 2153686 | 8/1985 |
| GB | 2172298 | 9/1986 |
| GB | 2 206 099 | 12/1988 |
| GB | 2166651 | 5/1996 |

(56) References Cited

FOREIGN PATENT DOCUMENTS

| | | |
|---|---|---|
| GB | 2337461 | 11/1999 |
| GB | 2 367 809 | 4/2002 |
| GB | 2 406 330 | 3/2005 |
| GB | 2406791 | 4/2005 |
| GB | 2 474 930 | 7/2012 |
| IL | 49491 | 9/1971 |
| IL | 0152486 A | 5/2003 |
| JP | 60001113 | 4/1978 |
| JP | 55069682 | 5/1980 |
| JP | 57044429 | 3/1982 |
| JP | 56039815 | 4/1984 |
| JP | 61275395 | 12/1986 |
| JP | 62241701 | 10/1987 |
| JP | 63119420 | 5/1988 |
| JP | 01100111 | 4/1989 |
| JP | 01156906 | 6/1989 |
| JP | 02184614 A | 7/1990 |
| JP | 2255890 | 10/1990 |
| JP | 04282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 8501529 | 2/1996 |
| JP | 2008040899 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000017174 A | 1/2000 |
| JP | 2000080017 | 3/2000 |
| JP | 2000128734 | 5/2000 |
| JP | 2000191429 | 7/2000 |
| JP | 2000239140 | 9/2000 |
| JP | 2000351726 | 12/2000 |
| JP | 2000354623 | 12/2000 |
| JP | 2001002526 | 1/2001 |
| JP | 2001019606 | 1/2001 |
| JP | 2001072963 | 3/2001 |
| JP | 2002012513 | 1/2002 |
| JP | 2002047136 | 2/2002 |
| JP | 2002/524490 | 8/2002 |
| JP | 2002302419 | 10/2002 |
| JP | 2003/012511 | 1/2003 |
| JP | 2003055146 | 2/2003 |
| JP | 2004047136 A | 2/2004 |
| JP | 2004250435 | 9/2004 |
| JP | 2004/348277 | 12/2004 |
| JP | 2005314323 | 11/2005 |
| JP | 2005350378 | 12/2005 |
| JP | 2006008574 | 1/2006 |
| JP | 2006/036317 | 2/2006 |
| JP | 2006/103799 | 4/2006 |
| JP | 2006525145 | 11/2006 |
| JP | 2007131539 | 5/2007 |
| JP | 2007326996 | 12/2007 |
| KR | 143232 | 7/1998 |
| KR | 2001003063 | 1/2001 |
| NZ | 520014 | 5/2005 |
| NZ | 540166 | 6/2007 |
| RU | 2277501 | 6/2006 |
| UA | 66796 | 6/2004 |
| WO | WO-8201821 | 6/1982 |
| WO | WO-86/05389 | 9/1986 |
| WO | WO-88/01863 | 3/1988 |
| WO | WO-8801502 | 3/1988 |
| WO | WO-88/08316 | 11/1988 |
| WO | WO-89/06537 | 7/1989 |
| WO | WO-90/05774 | 5/1990 |
| WO | 91/011991 | 8/1991 |
| WO | WO-91/11991 | 8/1991 |
| WO | WO-92/00077 | 1/1992 |
| WO | 92/05763 | 4/1992 |
| WO | WO-9205142 A1 | 4/1992 |
| WO | WO-92/11839 | 7/1992 |
| WO | WO-9325189 | 12/1993 |
| WO | WO-9406440 | 3/1994 |
| WO | WO-96/03115 | 2/1996 |
| WO | WO-96/19921 | 7/1996 |
| WO | WO-9624325 A1 | 8/1996 |
| WO | 96/26711 | 9/1996 |
| WO | WO-96/27376 | 9/1996 |
| WO | WO-96/39119 | 12/1996 |
| WO | WO-9703638 | 2/1997 |
| WO | WO-97/39745 | 10/1997 |
| WO | WO-9817282 | 4/1998 |
| WO | WO-98/18472 | 5/1998 |
| WO | WO-98/19654 | 5/1998 |
| WO | WO-98/21955 | 5/1998 |
| WO | WO-98/23291 | 6/1998 |
| WO | WO-98/36733 | 8/1998 |
| WO | 98/52536 | 11/1998 |
| WO | WO-99/08649 | 2/1999 |
| WO | WO-99/20250 | 4/1999 |
| WO | WO-99/37282 | 7/1999 |
| WO | WO-9953923 | 10/1999 |
| WO | WO-9953923 A1 | 10/1999 |
| WO | WO-00/09082 | 2/2000 |
| WO | WO-00/15193 | 3/2000 |
| WO | WO 00/62776 | 4/2000 |
| WO | WO-0023051 | 4/2000 |
| WO | WO-0033825 | 6/2000 |
| WO | WO-0038731 | 7/2000 |
| WO | WO-00/61076 | 10/2000 |
| WO | 00/072805 | 12/2000 |
| WO | WO-00/76461 | 12/2000 |
| WO | 01/05366 | 1/2001 |
| WO | WO-01/08681 | 2/2001 |
| WO | WO-0110961 A1 | 2/2001 |
| WO | 01/53198 | 7/2001 |
| WO | 01/54212 | 7/2001 |
| WO | WO-01/54679 | 8/2001 |
| WO | WO-0162209 A2 | 8/2001 |
| WO | WO-01/70242 A2 | 9/2001 |
| WO | 01/82890 | 11/2001 |
| WO | WO-01/82880 | 11/2001 |
| WO | WO-0185102 A2 | 11/2001 |
| WO | WO-0185128 | 11/2001 |
| WO | WO-0195728 A1 | 12/2001 |
| WO | WO-02/00820 | 1/2002 |
| WO | WO 02/07685 | 1/2002 |
| WO | WO-0215860 | 2/2002 |
| WO | WO-0215873 | 2/2002 |
| WO | WO-02/28435 | 4/2002 |
| WO | WO-02/41847 | 5/2002 |
| WO | 02/43490 | 6/2002 |
| WO | WO-02/43490 | 6/2002 |
| WO | WO-02/062324 | 8/2002 |
| WO | WO-02078667 A1 | 10/2002 |
| WO | WO-02/087519 | 11/2002 |
| WO | WO-03/000223 A1 | 1/2003 |
| WO | WO-03/002082 | 1/2003 |
| WO | 03/013984 | 2/2003 |
| WO | WO-03/051294 A2 | 6/2003 |
| WO | WO-03/055445 | 7/2003 |
| WO | WO-03/053292 A1 | 7/2003 |
| WO | WO-03/055454 | 7/2003 |
| WO | 03/070301 | 8/2003 |
| WO | 03/071995 | 9/2003 |
| WO | WO-03/075851 A2 | 9/2003 |
| WO | 03/097002 | 11/2003 |
| WO | WO-03/092641 A1 | 11/2003 |
| WO | WO-2004017962 | 3/2004 |

(56) References Cited

FOREIGN PATENT DOCUMENTS

| WO | WO-2004037197 | 5/2004 |
|---|---|---|
| WO | WO-2004037225 A2 | 5/2004 |
| WO | 2004/003284 | 8/2004 |
| WO | WO-2004064769 | 8/2004 |
| WO | WO-2004064833 A1 | 8/2004 |
| WO | WO-2004071479 A1 | 8/2004 |
| WO | WO-2004078158 | 9/2004 |
| WO | WO-2004078896 A1 | 9/2004 |
| WO | WO-2004093895 | 11/2004 |
| WO | WO-2004112780 A1 | 12/2004 |
| WO | WO-2005011567 A2 | 2/2005 |
| WO | WO-2005018530 A2 | 3/2005 |
| WO | WO-2005032522 A1 | 4/2005 |
| WO | WO-2005044219 A1 | 5/2005 |
| WO | WO-2005063224 | 7/2005 |
| WO | WO-2005065652 A1 | 7/2005 |
| WO | WO-2005076697 A2 | 8/2005 |
| WO | WO-2005097068 A1 | 10/2005 |
| WO | WO-2005102282 A1 | 11/2005 |
| WO | WO-2005102539 A1 | 11/2005 |
| WO | WO-2005117813 A1 | 12/2005 |
| WO | WO-2006003481 A2 | 1/2006 |
| WO | WO-2006010589 A2 | 2/2006 |
| WO | WO-2006011046 | 2/2006 |
| WO | WO-2006020682 A1 | 2/2006 |
| WO | WO-2006028339 A1 | 3/2006 |
| WO | WO-2006031271 A2 | 3/2006 |
| WO | WO-2006045170 A2 | 5/2006 |
| WO | WO-2006079632 A1 | 8/2006 |
| WO | WO-2006081327 | 8/2006 |
| WO | WO-2006091229 A2 | 8/2006 |
| WO | WO-2006100485 A1 | 9/2006 |
| WO | WO-2006120682 A2 | 11/2006 |
| WO | WO-2006121610 A2 | 11/2006 |
| WO | WO-2006122158 | 11/2006 |
| WO | WO-2006129161 A2 | 12/2006 |
| WO | WO-2006131784 A1 | 12/2006 |
| WO | 2007/010494 | 1/2007 |
| WO | WO-2007007208 A2 | 1/2007 |
| WO | WO-2007012977 A2 | 2/2007 |
| WO | WO-2007023396 A2 | 3/2007 |
| WO | WO-2007031621 A2 | 3/2007 |
| WO | WO-2007039825 A2 | 4/2007 |
| WO | WO-2007050543 A2 | 5/2007 |
| WO | WO-2007054818 A2 | 5/2007 |
| WO | WO-2007072216 A2 | 6/2007 |
| WO | 2007/082698 | 7/2007 |
| WO | WO-2007085899 A2 | 8/2007 |
| WO | WO-2007085902 A2 | 8/2007 |
| WO | WO-2007099396 A2 | 9/2007 |
| WO | WO-2007111962 A2 | 10/2007 |
| WO | WO-2008008397 A2 | 1/2008 |
| WO | WO-2008010963 | 1/2008 |
| WO | 2008/041045 | 4/2008 |
| WO | WO-2008038147 A2 | 4/2008 |
| WO | WO-2008075207 A2 | 6/2008 |
| WO | WO-2008087148 A2 | 7/2008 |
| WO | WO-2008110872 A2 | 9/2008 |
| WO | 2008/152444 | 12/2008 |
| WO | WO-2009007785 A2 | 1/2009 |
| WO | WO-2009069006 A2 | 6/2009 |
| WO | WO-2009072007 A2 | 6/2009 |
| WO | WO-2009087578 A2 | 7/2009 |
| WO | WO-2009090495 A2 | 7/2009 |
| WO | WO-2009090558 A2 | 7/2009 |
| WO | WO-2009098595 A2 | 8/2009 |
| WO | WO-2011039637 | 4/2011 |
| WO | WO-2011039638 | 4/2011 |
| WO | 2011/138678 | 11/2011 |
| WO | WO 2013/136192 | 9/2013 |

OTHER PUBLICATIONS

Arct, et al., "Common Cosmetic Hydrophilic Ingredients as Penetration Modifiers of Flavonoids", International Journal of Cosmetic Science, 24(6):357-366 (2002)—Abstract, 1 page.

Arisan, http://www.arisankimya.com/kozmetik.htm Accessed Dec. 10, 2008, 8 pages.

Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Barry, B.W. et al, Comparative bio-availability and activity of proprietary topical corticosteroid preparations: vasoconstrictor assays on thirty-one ointments, British Journal of Dermatology, 93, 563-571, 1975.

Benet, et al., Application of NMR for the Determination of HLB Values of Nonionic Surfactants, Journal of the American Oil Chemists Society, vol. 49, 1972, 499-500.

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfactants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstract, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (3 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carbowax 1000MSDS; http://www.sciencelab.com/xMSDS-Polyethylene.sub.--glycol.sub.--1000-9926- 622. Accessed Dec. 13, 2008, 6 pages.

Carelli, et al., "Effect of Vehicles on Yohimbine Permeation Across Excised Hairless Mouse Skin", Pharm Acta Hely, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Cheshire, et al., Disorders of Sweating, www.medscape.com, Semin Neurol 23(4):399-406, 2003.

Chevrant-Breton, et al., "Etude du Traitement Capillaire <<Bioscalin>> dans les Alopecies Diffuses de la Femme", Gazette Medicale, 93(17):75-79 (1986).

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.

(56) References Cited

OTHER PUBLICATIONS

Colloidal Silica. Retrieved online on Jun. 4, 2011. <URL:http://www.grace.com/engineeredmaterials/materialsciences/colloidalsilica/default.aspx >. Copyright 2011. 2 pages.
Croda 2. Croda Cetomacrogol 1000 Product Information Sheet. 2011 (no month given). 1 page.
Croda. Aracel 165 Product Summary. 2011 (no month given). 1 page.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Dawber, et al., "Hypertrichosis in Females Applying Minoxidil Topical Solution and in Normal Controls", JEADV, 17:271-275 (2003).
Denatonium Benzoate http://www.newdruginfo.com/pharmaceopeia/usp28/v28230/usp28nf23s0.sub.--m- 22790.htm Accessed Dec. 9, 2008, 2 pages.
Dentinger, et al., "Stability of Nifedipine in an Extemporaneously Compounded Oral Solution", American Journal of Health-System Pharmacy, 60(10):1019-1022 (2003)—Abstract, 1 page.
disorder. (2007). In the American Heritage Dictionary of the English Language. Retrieved from http://www.credoreference.com/entry/hmdictenglang/disorder. 1 page.
Draelos, Z. D. "Antiperspirants and the Hyperhidrosis Patients." Dermatologic Therapy. 2001. vol. 14. pp. 220-224.
Edens, et al., "Storage Stability and Safey of Active Vitamin C in a New Dual-Chamber Dispenser", Journal of Applied Cosmetology, 17(4):136-143 (1999)—Abstract, 1 page.
Edirisinghe, et al., "Effect of fatty acids on endothelium-dependent relaxation in the rabbit aorta", Clin Sci (Lond). Aug. 2006; 111(2): 145-51.
Edwards, "Imiquimod in Clinical Practice", J. Am Acad Dermatol., 43(1, Pt 2):S12-S17 (2000)—Abstract, 1 page.
Emulsifiers with HLB values. http://www.theherbarie.com/files/resources-center/formulating/Emulsifiers- .sub.--HLB.sub.--Values.pdf accessed Aug. 5, 2009 (3 pps).
Encyclopedia of Pharmaceutical Technology, Second Edition, vol. 3, Copyright 2002, 4 pages.
English machine translation of JP-08165218 (1996) 9 pages.
English translation of abstract for Japanese Patent Publication No. 4892282 (1992) 1 page.
Esposito, E. et al. "Nanosystems for Skin Hydration: A Comparative Study." International Journal of Cosmetic Science. 29. 2007. pp. 39-47.
Ethanol, Accessed http://www.sigmaaldrich.com/catalog/ProductDetail.do?N4=E7023SIAL&N5=SEAR- CH.sub.--CONCAT.sub.--PNOBRAND.sub.--KEY&F=SPEC Dec. 9, 2008, 2 pages.
Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.
European Official Action, European Patent Application No. 06831721.3, Feb. 3, 2009, 9 pages.
Farahmand, et al., "Formulation and Evaluation of a Vitamin C Multiple Emulsion", Pharmaceutical Development and Technology, 11(2):255-261 (2006)—Abstract, 1 page.
Final Office Action for U.S. Appl. No. 11/430,437, Tamarkin et al., Dec. 16, 2008, 24 pages.
Flick, Cosmetic and Toiletry Formulations, vol. 5, 2nd Edition, Copyright 1996, 63 pages. Relevant pp. 251-309.
Fonatana, Anthony J., "Water Activity: Why It is Important for Food Safety," International Conference on Food Safety, Nov. 16-18, 1998, pp. 177-185.
Gallarate, et al., "On the Stability of Ascorbic Acid in Emulsified Systems for Topical and Cosmetic Use", International Journal of Pharmaceutics, 188:233-241 (1999).
Galligan, John et al., "Adhesive Polyurethane Liners for Anterior Restorations," J. Dent. Res., Jul.-Aug. 1968, pp. 629-632.
Gelbard et al. "Primary Pediatric Hyperhidrosis: A Review of Current Treatment Options." Pediatric Dermatology. 2008. 25 (6). pp. 591-598.
Graves, S. et al. "Structure of Concentrated Nanoemulsions." The Journal of Chemical Physics.. 122 America Institute of Physics. Published Apr. 1, 2005. 6 pages.
Gschnait, F., et al., "Topical Indomethacin Protects from UVB and UVA Irradiation," Arch. Dermatol. Res. 276:131-132, 1984.
Hall, Karla, "Diaper Area Hemangiomas: A Unique Set of Concerns," http://members.tripod.com/.about.Michelle.sub.--G/diaper.html, Dec. 1, 2008, 8 pages.
Hallstar. Retrieved online on Jun. 4, 2011. <URL:http://www.hallstar.com/pis.php?product=1H022>. 1 page.
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Imiquimod 5% Cream in the Treatment of Actinic Keratoses of the Face, Scalp, or Hands and Arms", Arch. Dermatol. Res., 296(1):6-11 (2004)—Abstract, 1 page.
Hashim, et al. "Tinea versicolor and visceral leishmaniasis," Int J Dermatol., Apr. 1994; 33(4), pp. 258-259 (abstract only). 2 pages.
Heart Failure, The Merck Manual, 2008 <<http://www.merck.com/mmhe/sec03/ch025/ch025a.html>> 12 pages.
Hepburn, NC., "Cutaneous leishmaniasis," Clin Exp Dermatol, Jul. 2000; 25(5), pp. 363-370 (abstract only), 2 pages.
Hill, Randall M. (Ed.) Silicone Surfactants, Table of Contents and Chapter 7, "Silicone Surfactants: Applicants in the Personal Care Industry," by David T. Floyd, 1999 (30 Pages).
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop. 1 page. Accessed Jan. 31, 2010.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.
ICI Americas Inc. "The HLB System: A Time-Saving Guide to Emulsifier Selection." Mar. 1980. pp. 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Innocenzi, Daniele et al., "An Open-Label Tolerability and Efficacy Study of an Aluminum Sesquichlorhydrate Topical Foam in Axillary and Palmar Primary Hyperhidrosis," Dermatologic Therapy, vol. 21, S27-S30, 2008.
International Search Report and Written Opinion for International Application No. PCT/IB10/02241 mailed Feb. 10, 2011. 9 pages.
International Search Report and Written Opinion for International Application No. PCT/IB10/02613 mailed Mar. 16, 2011. 9 pages.
International Search Report and Written Opinion for International Application No. PCT/IB10/02617 mailed Mar. 15, 2011. 10 pages.
International Search Report and Written Opinion, International Application No. PCT/IB2006/003628, Foamix Ltd., Dec. 7, 2007, 15 pages.
International Search Report and Written Opinion, International Application No. PCT/US2007/004459, Foamix Ltd., Dec. 9, 2008, 15 pages.
International Search Report and Written Opinion, International Patent Application No. PCT/IB2006/004026, Foamix, Ltd., May 20, 2008, 17 pages.
International Search Report for International Application No. PCT/IB2006/003974, Feb. 25, 2008 (7 pages).
International Search Report from PCT/IB2006/003519 , Mailed Dec. 3, 2007. 1 page.
International Search Report, International Patent Application No. PCT/IB2007/003463, Foamix, Ltd., Jul. 18, 2008, 6 pages.

(56) References Cited

OTHER PUBLICATIONS

International Search Report, International Patent Application No. PCT/IB2007/003759, Foamix Ltd., Jul. 8, 2008 (7 pages).
Invitation to Pay Additional Fees for International Application No. PCT/IB2009/005012 mailed Jul. 27, 2010. 13 pages.
Izquierdo, P. et al. "Formation and Stability of Nano-Emulsions Prepared Using the Phase Inversion Temperature Method." University of Barcelona. Sep. 17, 2001. 3 page.
Kalkan, et al., The Measurement of Sweat Intensity Using a New Technique, Tr. J. of Medical Sciences 28, 515-517 (1998).
Kanamoto, et al., "Pharmacokinetics of two rectal dosage forms of ketoprofen in patients after anal surgery," J Pharmacobiodyn., Mar. 1988; 11(3):141-5, Abstract, 1 page.
Kang,et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," pp. 1-78, 2000.
Kathon.TM. CG (product information sheet by Rohm and Haas, Jun. 2006). 9 pages.
Kim, "Stability of Minoxidil in Aqueous Solution", Yakhak Hoechi, 30(5):228-231 (1986)—Abstract, 2 pages.
Kinnunen, Contact Dermatitis Sep. 1989; 21(3): 154-8, Abstract, 2 pages.
Kleber, M.D., H.D. et al., "Treatment of Patients with Substance Use Disorders, Second Edition," pp. 1-276, 2006.
Koerber, S., "Humectants and Water Activity," Water Activity News, 2000, ISSN No. 1083-3943. 8 pages.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." J. Am. Acad. Dermatol. 45:487-498. Oct. 2001.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery" in *Water-Soluble Polymers*, American Chemical Society, Chapter 23, 1991, pp. 350-366.
Licking Vaginal Dryness without a Prescription. Accessed http://www.estronaut.com/a/vag.sub.--dryness.htm on Dec. 14, 2008, 3 pages.
Lippacher, A. et al. " Liquid and Semisolid SLN Dispersions for Topical Application Rheological Characterization." European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale, The extra pharmacopoeia [28th] edition, Eds.: Reynolds, J.E.F. and Prasad, A.B., The Pharmaceutical Press, London, pp. 862-864, 1982.
Material Safety Data Sheet, Science Lab.com, Polyethylene Glycol 1000, MSDS, Nov. 6, 2008, 6 pages.
Merck Index, An Encyclopedia of Chemicals, Drugs, and Biologicals. 13$^{th}$ Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Messenger, et al., "Minoxidil: Mechanisms of Action on Hair Growth", British Journal of Dermatology, 150:186-194 (2004).
Metronidazole. www.usp.org/pdf/EN/veterinary/metronidazole.pdf. accessed Sep. 10, 2009, 4 pages.

Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
No Author Listed. "Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Paula. http://ww.cosmeticscop.com/cosmetic-ingredient-dictionary/definition/259/c12-15-alkyl-benzoate.aspx. Printed Oct. 24, 2010. 1 page.
PCT Search Report and Written Opinion for International Application No. PCT/IB2010/001126 mailed Apr. 20, 2011, 12 pages.
Pendergrass, Gynecol Obstet. Invest. 1996:42(3):178-82, Abstract, 2 pages.
Prescription Information for Aldara, Mar. 2007 (29 pages).
Prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Savin, et al., "Tinea versicolor treated with terbinafine 1% solution," Int J. Dermatol, Nov. 1999; 38(11), pp. 863-865.
Schmidt A., "*Malassezia furfur*: a fungus belonging to the physiological skin flora and its relevance in skin disorders," Curtis., Jan. 1997; 59(1), pp. 21-4 (abstract), 2 pages.
Schutze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-s/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only). 2 pages.
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Sigma Aldrich, "HLB-Numbers in Lithography Nanopatterning," http://www.sigmaaldrich.com/materials-science/micro-and-nanoelectronics/I- ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Silicone. Definition. Retrieved Apr. 19, 2011 from http://www.oxforddictionaries.com/definition/silicone?view=uk. 1 page.

(56) References Cited

OTHER PUBLICATIONS

Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, http://web.archive.org/web/20030810230608/http://www.skinbio.com/cpserum.-html, Dec. 1, 2008, 21 pages.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. Accessed May 19, 2010, 3 pages.
Sonneville-Aubrun, O. et al. "Nanoemulsions: A New Vehicle for Skincare Products." Advances in Colloid and Interface Science. 108-109.. 2004. pp. 145-149.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only). 1 page.
Sreenivasa, et al., "Preparation and Evaluation of Minoxidil Gels for Topical Application in Alopecia", Indian Journal of Pharmaceutical Sciences, 68(4):432-436 (2006), 11 pages.
Sugisaka, et al., the Physiochemical Properties of Imiquimod, the First Imidazoquinoline Immune Response Modifier, Abstract 3030, Pharmaceutical Research, vol. 14, No. 11 Supplemental (November), p. S475 (1997), 2 pages.
Surfactant. Wikipedia—http://en.wikipedia.org/wiki/surfactant. Printed Oct. 24, 2010. 7 pages.
Sweetman, Sean C. Martindale: The Complete Drug Reference. 33rd Edition. London. Pharmaceutical Press. Jun. 21, 2002. pags. 1073 and 1473. 5 pages.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate -1. Accute toxicity of hydrocortisone 17-butyrate 21-propionate and its analogues in mice, rats and dogs (author's trans), J Toxicol Sci., Jul. 1981; 6 Suppl: 1-16, Abstract, 1 page.
Tata, et al., "Penetration of Minoxidil from Ethanol Propylene Glycol Solutions: Effect of Application Volumne on Occlusion", Journal of Pharmaceutical Sciences, 84(6):688-691 (1995).
Torres-Rodriguez, JM., "New topical antifungal drugs," Arch Med Res. 1993 Winter; 24(4), pp. 371-375 (abstract), 2 pages.
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of in Vitro Mass Balance Technique with Minosidil Solutions", J. Pharm. Sci., 81(8):736-743 (1992)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Journal of Cell Biology, 117(2):327-335, Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, "Scale up of an olive/water cream containing 40% diethylene glycol momoethyl ether", Dev. Ind. Pharm., 26(1):71-77 (2000).
Wormser et al., Protective effect of povidone-iodine ointment against skin lesions induced by sulphur and nitrogen mustards and by non-mustard vesicants, Arch. Toxicol., 1997, 71, 165-170.
Wormser, Early topical treatment with providone-iodine ointment reduces, and sometimes prevents, skin damage following heat stimulus, Letter to the Editor, Burns 24, pp. 383, 1998.
U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
Raschke, et al., "Topical Activity of Ascorbic Acid: From in Vitro Optimization to in Vivo Efficacy", Skin Pharmacology and Physiology, 17(4):200-206 (2004)—Abstract, 1 page.
Merck index, 10th edition, Merck & Co., Inc.: Rahway, NJ, 1983, pp. 39 (entry 242 for allantoin).
Padhi et al., "Phospho-olicines as positive-electrode materials for rechargeable lithium batteries," J. Electrochemical Soc., 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Gill, A.M, et al., "Adverse Drug Reactions in a Paediatric Intensive Care Unit," Acta Paediatr 84:438-441, 1995.
Gladkikh, "Ascorbic Acid and Methods of Increasing its Stability in Drugs", Translated from Khimiko-Farmatsevticheskii Zhurnal, 4(12):37-42 (1970)—1 page.
Glaser, et al., Hyperhidrosis: A Comprehensive and Practical Approach to Patient Management, Expert Rev. Dermatol. 1(6), 773-775 (2006).
Groveman, et al., "Lack of Efficacy of Polysorbate 60 in the Treatment of Male Pattern Baldness", Arch Intern Med, 145:1454-1458 (1985).
Gschnait, F., et al., "Topical Indomethacin Protects from UVB and UVA Irriadiation," Arch. Dermatol. Res. 276:131-132, 1984.
Hakan, et al., "The protective effect of fish oil enema in acetic acid and ethanol induced colitis," The Turkish Journal of Gasroenterology, 2000, vol. 11, No. 2, pp. 155-161.
Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).
Li, et al., "Solubility Behavior of Imiquimod in Alkanoic Acids", Abstract 3029, Pharmaceutical Research, vol. 14, No. 11 Supplemental (November), p. S475 (1997), 2 pages.
Material Safety Data Sheet, Progesterone, Apr. 26, 2006, 5 pages.
Merriam Webster Online Dictionary [online] retrieved from http://www.merriam-webster.com/cgi-bin/dictionary?book=dictionary&va=derivative on Jul. 5, 2008; 1 page.
Merriam-Webster Online Dictionaary, 2008, "Mousse," Merriam-Webster Online, Dec. 8, 2008 http://www.merriam-webster.com/dictionary/mousse, 2 pages.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate. http://www.makingcosmetics.com/sunscreens/OM-Cinnamate-p102.html accessed Sep. 26, 2009, 1 page.
Ravet et al., "Electroactivity of natural 503-507 and synthetic triphylite," J. of Power Sources, 2001, 97-98: 503-507.
Raymond, Iodine as an Aerial Disinfectant, Journal of Hygiene, vol. 44, No. 5 (May 1946), pp. 359-361.

(56) References Cited

OTHER PUBLICATIONS

Rosacea, http://clinuvel.com/skin-conditions/common-skin-conditions/rosacea#h0-6-prevention. Accessed Sep. 9, 2010, 5 pages.
Schmidt A., "*Malassezia furfur*: a fungus belonging to the physiological skin flora and its relevance in skin disorders," Curtis., Jan. 1997; 59(1), pp. 21-4 (abstract).
Shrestha et al., Forming properties of monoglycerol fatty acid esters in nonpolar oil systems, *Langmuir*, 2006, 22: 8337-8345.
Stehle et al., Uptake of minoxidil from a new foam formulation devoid of propylene glycol to hamster ear hair follicles, *J. Invest. Dermatol.*, 2005, 124(4), A101.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tata, et al., "Relative Influence of Ethanol and Propylene Glycol Cosolvents on Deposition of Minoxidil into the Skin", Journal of Pharmaceutical Sciences, 83(10):1508-1510 (1994).
Tsai, et al., "Effect of Minoxidil Concentration on the Deposition of Drug and Vehicle into the Skin", International Journal of Pharmaceutics, 96(1-3):111-117 (1993)—Abstract, 1 page.
"Coal tars and coal-tar pitches," *Report on Carcinogens, Twelfth Edition*, 2011, 3 pages.
Adisen et al. "Topical tetracycline in the treatment of acne vulgaris," *J Drugs Dermatol.*, 2008, 7:953-5.
Baskaran et al., "Poloxamer-188 improves capillary blood flow and tissue viability in a cutaneous burn wound," *J. Surg. Res.*, 2001, 101(1):56-61.
Bell-Syer et al. "A systematic review of oral treatments for fungal infections of the skin of the feet," *J. Dermatolog. Treat.*, 2001, 12:69-74.
Boehm et al. 1994, "Synthesis of high specific activity [.sup.3 H]-9-cis-retinoic acid and its application for identifying retinoids with unusual binding properties," *J. Med. Chem.*, 37:408-414.
Carapeti et al., "Topical diltiazem and bethanechol decrease anal sphincter pressure and heal anal fissures without side effects," *Dis Colon Rectum*, 2000, 43(10):1359-62.
Cook and Mortensen, "Nifedipine for treatment of anal fissures," *Dis Colon Rectum*, 2000, 43(3):430-1.
Dumortier et al., "A review of poloxamer 407 pharmaceutical and pharmacological characteristics," *Pharmaceutical Res.*, 2006, 23(12):2709-2728.
Ebadi et al., "Healing effect of topical nifedipine on skin wounds of diabetic rats," *DARU*, 2003, 11(1):19-22.
Effendy and Maibach. "Surfactants and Experimental Irritant Contact Dermatitis." *Contact Dermatol.*, 1995, 33:217-225.
Elias and Ghadially, "The aged epidermal permeability barrier," *Clinical Geriatric Medicine*, Feb. 2002, pp. 103-120.
Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.
Fluhr et al., "Glycerol accelerates recovery of barrier function in vivo," *Acta Derm. Venereol,*. 1999, 79:418-21.
Garti et al. "Sucrose Esters microemulsions," *J. Molec. Liquids*, 1999, 80:253-296.
Hammer et al. "Anti-Microbial Activity of Essential Oils and other Plant extracts," *J. Applied Microbiology*, 1999, 86:985-990.
Hwang et al. "Isolation and identification of mosquito repellents in *Artemisia vulgaris*," *J. Chem. Ecol.*, 11: 1297-1306, 1985.
Knight et al., "Topical diltiazem ointment in the treatment of chronic anal fissure," *Br. J. Surg.*, 2001, 88(4):553-6.
Leive et al, "Tetracyclines of various hydrophobicities as a probe for permeability of *Escherichia coli* outer membrane," *Antimicrobial Agents and Chemotherapy*, 1984, 25:539-544.
Luepke and Kemper, "The HET-CAM Test: An Alternative to the Draize Eye Test," *FD Chem. Toxic.*, 1986, 24:495-196.
Osborne and Henke, "Skin Penetration Enhancers Cited in the Technical Literature," *Pharm. Technology*, Nov. 1997, pp. 58-86.

Padi. "Minocycline prevents the development of neuropathic pain, but not acute pain: possible anti-inflammatory and antioxidant mechanisms," *Eur J. Pharmacol*, 2008, 601:79-87.
Palamaras and Kyriakis, "Calcium antagonists in dermatology: a review of the evidence and research-based studies," *Derm. Online Journal*, 2005, 11(2):8.
Passi et al., Lipophilic antioxidants in human sebum and aging, *Free Radical Research*, 2002, pp. 471-477.
Perrotti et al., "Topical Nifedipine With Lidocaine Ointment vs. Active Control for Treatment of Chronic Anal Fissure," *Dis Colon Rectum*, 2002, 45(11):1468-1475.
Repa et al. "All-trans-retinol is a ligand for the retinoic acid receptors," *Proc. Natl. Acad Sci, USA*, 90: 7293-7297, 1993.
Ruledge, "Some corrections to the record on insect repellents and attractants," *J. Am. Mosquito Control Assoc*, 1988, 4(4): 414-425.
Sakai et al., "Characterization of the physical properties of the stratum corneum by a new tactile sensor," *Skin Research and Technology*, Aug. 2000, pp. 128-134.
Schaefer, "Silicone Surfactants," *Tenside, Surfactants, Deterg.*, 1990, 27(3): 154-158.
Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.
Smith, "Hydroxy acids and skin again," *Soap Cosmetics Chemical Specialties*, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," *European J. Pharm. Biopharm.*, 1998, 46(3):265-71.
Todd et al. "Volatile Silicone Fluids for Cosmetics," *91 Cosmetics and Toiletries*, 1976, 27-32.
Torma et al., "Biologic activities of retinoic acid and 3,4-dehydroretinoic acid in human keratinoacytes are similar and correlate with receptor affinities and transactivation properties," *J. Invest. Dermatology*, 1994, 102: 49-54.
USP23/NF 18 the United States Pharmacopeia: The National Formulary, US Pharmacopoeia, 1995, p. 10-14.
Van Slyke, "On the measurement of buffer values and on the relationship dissociation constant of the buffer and the concentration and reaction of buffer value to the of the buffer solution," *J. Biol. Chem.*, 1922, 52:525-570.
Van Cutsem et al., "The antiinflammatory efects of ketoconazole,". *Am. Acad. Dermatol.*,1991 25(2 pt 1):257-261.
Wang and Chen, "Preparation and surface active properties of biodegradable dextrin derivative surfactants," *Colloids and Surfaces A: Physicochemical and Engineering Aspects*, 2006, 281(1-3): 190-193.
Weindl et al., "Hyaluronic acid in the treatment and prevention of skin diseases: molecular biological, pharmaceutical and clinical aspects," *Skin Pharmacology and Physiology*, 2004, 17: 207-213.
Xynos et al., "Effect of nifedipine on rectoanal motility," *Dis Colon Rectum*, 1996, 39(2):212-216.
Yamada et al., "Candesartan, an angiotensin II receptor antagonist, suppresses pancreatic inflammation and fibrosis in rats," *J. Pharmacol. Exp. Ther.*, 2003, 307(1)17-23.
Paragraph E.3.1 of regulation (EC) No. 2003 (See Directive 67/548/EEC OJ 196, 16.8, 1967, p. 1.
Tzen et al., Lipids, proteins and structure of seed oil bodies from diverse species; *Plant Physiol.*, 1993, 101:267-276.
Brown et al. "Structural dependence of flavonoid interactions with $Cu^{2+}$ inos: implications for their antioxidant properties," *Biochem. J.*, 1998, 330:1173-1178.
Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.
"Mineral oil USP," Chemical Abstracts Service Registry No. 8012-95-1, 2011, 7 pages.
"Tea tree oil," Chemical Abstract No. 68647-73-4, 2012, 2 pages.

(56) References Cited

OTHER PUBLICATIONS

Lin et al., "Ferulic acid stabilizes a solution of vitamins c and e and doubles its protoprotection of skin," *J Invest Dermatol*, 2005, 125:826-32.
International Preliminary Report on Patentability from PCT/IB2008/003939, dated Jun. 10, 2008, 7 pages; International Search Report, dated Sep. 25, 2009, 3 pages.
"Burn patients need vitamin D supplements." Decision News Media, Jan. 23, 2004, http://www.nutraingredients.com/Research/Burn-patients-need-vitamin-D-supplements, Accessed: May 5, 2010.
"Minocycline" accessed on Ocotober 21, 2011 at en.wikipedia.org/wiki/Minocycline, 7 pages.
"Reaction Rate" Accessed at en.wikipedia.org/wild/Reaction_rate on Dec. 18, 2011, 6 pages.
'Niram Chemicals' [online]. Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.
Anton, N. et al. "Water-in-Oil Nano-Emulsion Formation by the phase inversion Temperature Method: A Novel and General Concept, a New Template for Nanoencapsulation," Proceedings of the 33rd Annual Meeting and Exposition of the Controlled Release Society, Jul. 2006, Vienna, Austria, 2 pages.
Bally and Badal, "Stability of minocycline, doxycycline, and tetracycline stored in agar plates and microdilution trays," Current Microbiology, 1978, 1:33-36.
Cetearyl Alcohol, Natural Wellbeing, Copyrigh 2001-2012, retrieved on Apr. 10, 2014, http://www.naturalwellbeing.com/learning-center/Cetearyl_Alcohol, 3 pages.
Hargreaves, "Chemical Formulation, An Overview of Surfactant-Based Preparations Used in Everyday Life", The Royal Society of Chemistry, pp. 114-115 (2003).
Hormones. Http://www.greenwillowtree.com/Page.bok?file=libido.html. Jan. 2001.
hydroxyethylcellulose. Http: //terpconnect.umd.edu/-choi/MSDS/Sigma-Aldrich/HYDROXYETHYL%2OCELLULOSE, 5 pages, Jan. 14, 2004.
Jan. "Troubled Times: Detergent Foam." http://zetatalk.com/health/theal17c.htm. Accessed Feb. 9, 2012. 2 pages.
Joseph, "Understanding foams & foaming," University of Minnesota (1997), at http://www.aem.umn.edu/people/faculty/joseph/archive/docs/understandingfoams.pdf, pp. 1-8.
Kucharekova et al., "Effect of a lipid-rich emollient containing ceramide 3 in experimentally induced skin barrier dysfunction," Contact Dermatitis, Jun. 2002, pp. 331-338.
Lebwohl et al., "A randomized, double-blind, placebo-controlled study of clobestasol propionate 0.05% foam in the treatment of nonscalp psoriasis," International Journal of Dermatology, 2002, 41(5): 269-274.
Leung, et al., "Bioadhesive Drug Delivery in Water-Soluble Polymers," American Chemical Society, Chapter 23, 1991, pp. 350-366.
Martindale. 33 ed. London, Bath Press, 2002. pp. 1073 and 1473.
Merck index, 14th edition, O'Neill, ed., 2006, entry for p-amino benzoic acid.
Merck index, 14th edition, O'Neill, ed., 2006, entry for zinc oxide.
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.
Neves et al., "Rheological Properties of Vaginal Hydrophilic Polymer Gels," *Current Drug Delivery*, 2009, 6:83-92.
Nietz, "Molecular orientation at surfaces of solids," *J. Phys. Chem.*, 1928, 32(2): 255-269.
Oil. Dictionary of Chemistry. Editor: DWA Sharp. Copyright 1990.
Sciarra, "Aerosol Technology," Kirk-Othmer Encyclopedia of Chemical Technology, Jul. 2012, 20 pages.

Sehgal, " Ciclopirox: a new topical pyrodonium antimycotic agent: A double-blind study in superficial dermatomycoses," British Journal of Dermatology, 1976, 95:83-88.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Softemul-165: Product Data Sheet, Mohini Organics PVT LTD, retrieved Apr. 10, 2014, http://www.mohiniorganics.com/Softemul165.html#, 1 page.
Tayss et al., "Anionic detergent-induced skin irritation and anionic detergent-induced pH rise of bovine serum albumin," *J. Soc. Cosmet. Chem.*, Jul./Aug. 1988, 39:267-272.
Third Party Submission for U.S. Appl. No. 12/014,088, Feb. 4, 2009, 4 pages, cited by other.
Tirmula et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Yamada and Chung, "Crystal Chemistry of the Olivine-Type Li(MnyFe1-y)PO4 and (MnyFe1-y)PO4 as Possible 4 V Cathode Materials for Lithium Batteries," J. Electrochemical Soc., 2001, 148(8): A960-967.
"New Nanomaterials to deliver anticancer drugs to cells developed," *Science Daily*, Jun. 2007, retrieved on Oct. 14, 2013, <URL: http://www.sciencedaily.com/releases/2007/06/070607112931.htm>, 3 pages.
"Drug Index (Professional)—Dacarbazine," *BC Cancer Agency*, Jun. 2004, retrieved on Oct. 18, 2013, <URL:http://www.bccancer.bc.ca/HPI/DrugDatabase/DrugIndexPro/Dacarbazine.htm>, 6 pages.
"Dacarbazine," *Chemical Book*, 2010, retrieved on Oct. 18, 2013, <URL: http://www.chemicalbook.com/ChemicalProductProperty_EN_CB7710656.htm>, 2 pages.
Chuna, "Minocycline versus Doxycycline in the treatment of Lyme Neuroborreliosis," *Clin. Infect. Diseases*, 2000, 30: 237-238.
"Product Data Sheet for Meclocycline," *bioaustralis fine chemicals*, Jun. 28, 2013, 1 page.
"Minocycline (DB01017)," *DrugBank*, Feb. 8, 2013, retrieved on Aug. 15, 2013, <http://www.drugbank.ca/drugs/DB01017>, 10 pages.
Google search strategy for minocycline solubility, retrieved on Aug. 15, 2013, <http://www.googl.com/search?rls=com.microsoft%3Aen-us%3AIE-SearchBox&q-melocycline+solubility>, 1 page.
"Fully refined paraffin waxes (FRP Wax)," *Industrial Raw Materials LLC*, Feb. 21, 2008, retrieved on Aug. 22, 2013, <http://irmwax.com/Wax/Paraffin/fully_refined.asp> 1 page.
Harry, "Skin Penetration," *The British Journal of Dermatology and Syphillis*, 1941, 53:65-82.
Abrams et al., "Ciclopirox gel treatment of scalp seborrheic dermatitis," *Hydroxy-Piridones as Antifungal Agents with Special Emphasis on Onychomycosis*, 1999, Chapter 8, 45-50.
Purdy et al., "Transfusion-transmitted malaria: unpreventable by current donor exclusion guidelines?" *Transfusion*, Mar. 2004, 44:464.
*Reregistration Eligibility Decision for Pyrethrins*, EPA, Jun. 7, 2006, 108 pages.
"Arquad HTL8-MS," *AkzoNobel Functional Applications*, retrieved on Mar. 18, 2013, Retrieved from the Internet: <URL: http://sc.akzonobel.com/en/fa/Pages/product-detail.aspx?prodID=8764>, 1 page.
Blaney and Cook, "Topical use of tetracycline in the treatment of acne," *Arch Dermatol*, Jul. 1976, 112:971-973.
"View of NCT01362010 on Jun. 9, 2011," ClinicalTrials.gov_archive, Jun. 9, 2011, retrieved on Sep. 9, 2013, <http://clinicaltrials.gov/archive/NCT01362010/2011_06_09>, 3 pages.
"View of NCT01171326 on Dec. 7, 2010," ClinicalTrials.gov archive, Dec. 7, 2010, retrieved on Sep. 9, 2013, <http://clinicaltrials.gov/archive/NCT01171326/2010_12_07>, 4 pages.
Durian et al., "Scaling behavior in shaving cream," *The Americal Physical Society*, Dec. 1991, 44(12):R7902-7905.
Livingstone and Hubel, "Segregation of form, color, movement, and depth: Anatomy, physiology, and perception," *Science*, May 1988, 240:740-749.

(56) References Cited

OTHER PUBLICATIONS

Lee et al., "Historical review of melanoma treatment and outcomes," *Clinics in Dermatology*, 2013, 31: 141-147.

Scully et al., "Cancers of the oral mucosa treatment and management," *Medscape Drugs, Diseases and Procedures*, Apr. 20, 2012, retrieved on Oct. 12, 2013, <http://emedicine.medscape.com/article/1075729-treatment>, 10 pages.

"What is TSC?," *Tuberous Sclerosis Alliance*, Jan. 1, 2005, retrieved on Feb. 6, 2014, <URL: http://www.tsalliance.org.pages.aspx?content=2>, 3 pages.

"Can tuberous sclerosis be prevented?," *Sharecare*, 2002, retrieved on Aug. 29, 2013, <URL: http://www.sharecare.com/health/autosomal-dominant-generic-disorders/can-tuberous-sclerosis-be-prevented;jsessionid=850579B60520A907DE75930E061E60E6>, 2 pages.

Prud'homme et al., *Foams: theory, measurements and applications*, Marcel Dekker, Inc., 1996, 327-328.

Schmolka, "A review of block polymer surfactants," *Journal of the American Oil Chemists Society*, Mar. 1977, 54: 110-116.

"Shear," Vocabulary.com, retrieved on Aug. 23, 2013, <URL: https://www.vocabulary.com/dictionary/shear>, 3 pages.

"Sheer," Vocabulary.com, retrieved on Aug. 23, 2013, <URL: https://www.vocabulary.com/dictionary/sheer>, 3 pages.

*Sun Pharmaceutical Industried Ltd.* v. *Eli Lilly and Co.*, 611 F.3d 1381, 95 USPQ2d 1797 (Fed. Cir. 2010),7 pages.

*Molins PLC* v. *Textron Inc.*, 48 F.3d 1172, 33 USPQ2d 1823 (Fed. Cir. 1995), 19 pages.

"Crohn's Disease," *Merch Manual Home Edition*, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.

"Gas Gangrene," Merch Manual Home Edition, 2008, retrieved on Jan. 16, 2013, <http://www.merckmanuals.com/home/infections/bacterial_infections/gas_gangrene.html?qt=gas gangrene&alt=sh>1 page.

"Human Immunodeficiency Virus Infection," Merch Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh>, 11 pages.

Schott, "Rheology," *Remington's Pharmaceutical Sciences*, 17th Edition, 1985, 330-345.

\* cited by examiner

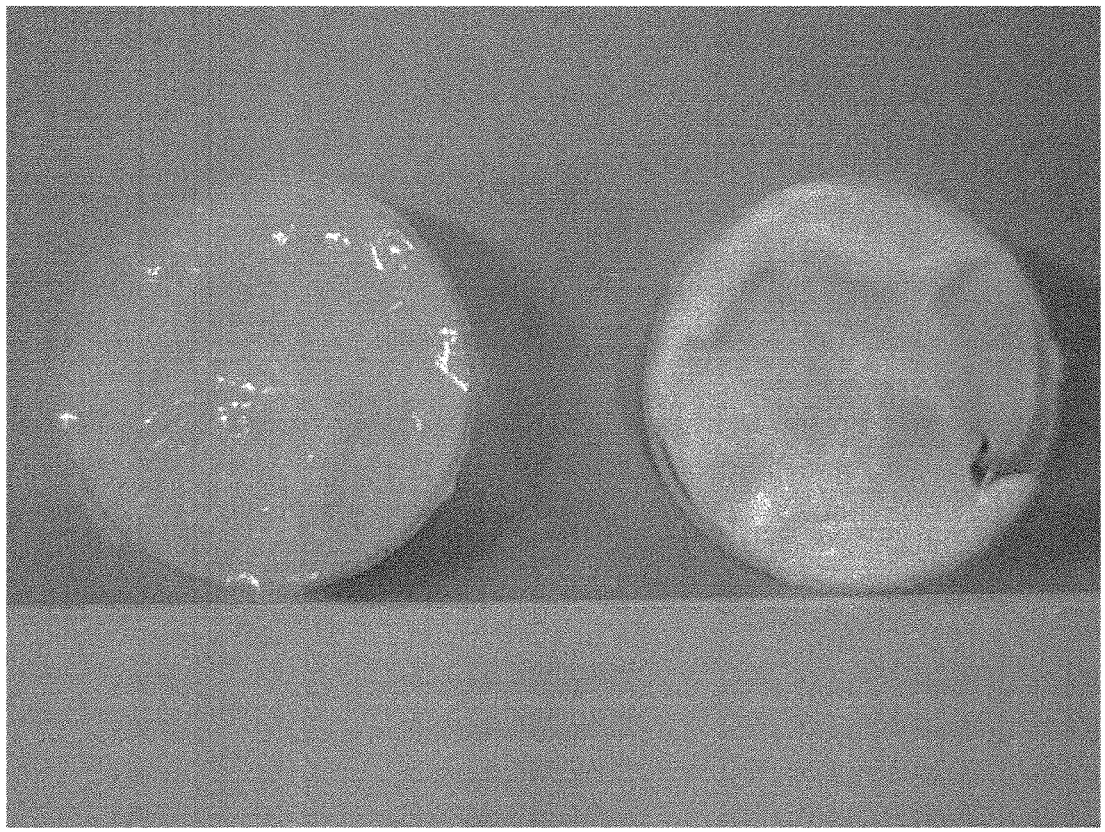
Fast Cooling　　　Slow Cooling

OIL AND LIQUID SILICONE FOAMABLE CARRIERS AND FORMULATIONS

CROSS REFERENCE TO RELATED APPLICATIONS

This application is a continuation under 35 U.S.C. §120 of PCT/IB2008/03939, filed on Dec. 8, 2008, which claims priority under 35 U.S.C. §119(e) of U.S. Provisional Patent Application No. 61/012,414, filed on Dec. 7, 2007, entitled "Carriers, Formulations, Methods For Formulating Unstable Active Agents For External Application And Uses Thereof," and U.S. Provisional Patent Application No. 61/103,500, filed on Oct. 7, 2008 entitled "Oil and Liquid Silicone Carriers and Formulations for External and Body Cavity Application of Active Agents and Uses Thereof."

FIELD

This invention relates to waterless foam formulations, specifically single phase foamable composition including silicone. The invention further relates to methods for formulating stable and unstable active agents in topical compositions, which are suitable, inter alia, for applying to the skin or to mucosal surfaces and can be used for treating topical, mucosal and/or systemic disorders in mammals. The invention further relates to vehicles which are suitable, inter alia, for delivery for a wide range of active pharmaceutical and cosmetic agents and methods for their use.

BACKGROUND

External topical administration is an important route for the administration of drugs in both systemic and topical disease treatment. For example, diseases of the skin, such as inflammatory diseases (e.g., acne), rashes, infection (e.g., microbial infection and parasitic infestation), and immune system reactions leading to rashes and/or infection, are typically treated via topical administration of a pharmaceutical active agent. Many drugs that may be useful for topical administration (e.g., antibiotics, anti-fungal agents, anti-inflammatory agents, anesthetics, analgesics, anti-allergic agents, corticosteroids, retinoids and anti-proliferative medications) are preferably administered in hydrophobic media, such as a petrolatum-based ointment or a cream, due to their increased stability in hydrophobic solvents. While the use of stabilizers, anti oxidants antimicrobial preservatives, buffers and the like in aqueous compositions to protect active or cosmetic agents is known, there are still disadvantages to formulating certain active agents in aqueous compositions, or even in compositions containing low amounts of polar solvents such as water (e.g., water in oil emulsions). For example, some active agents are known to be generally unstable or susceptible to isomerisation or to breakdown in the presence of water, resulting in loss of activity. Thus, in several cases, many drugs are more soluble or more stable in hydrophobic solvents; and therefore, the development of simple and elegant formulations to accommodate and stabilize active ingredients in a hydrophobic waterless or substantially waterless environment is desirable.

However, hydrophobic formulations, in particular ointments, also pose disadvantages to topical administration. For example, ointments often form an impermeable barrier. In the treatment of a topical wound, such a barrier would prevent the removal or draining of metabolic products and excreta from these wounds. Moreover, the efficacy of drugs formulated in ointments is compromised because of the difficulty for an active drug dissolved in an ointment-based carrier to pass through the barrier layer into the wound tissue. In addition, ointments and creams often do not create an environment for promoting respiration of wound tissue or normal respiration of the skin. An additional disadvantage of ointment formulations is the greasy feeling left following their topical application onto the skin, mucosal membranes and wounds.

Formulations based on hydrophobic media also include those based on oils or hydrophobic emollient vehicles. These formulations have a number of useful attributes making them suitable candidates for topical pharmaceutical and cosmetic compositions, including foamable compositions. They are inherently stable and inert which are clearly desirable characteristics. They are able to condition the skin and in appropriate amounts can form a barrier to skin moisture loss. By appropriate formulation they can act to improve drug delivery to the skin and yet remain resistant to being washed off. On the other hand, they are by their nature greasy materials and can be difficult to formulate particularly into a topical foamable composition that can deliver a substantially uniform and stable composition or foam that ameliorates or overcomes the look and feel of a greasy material, especially where that composition is waterless or substantially so. It is further a problem to incorporate into such a vehicle pharmaceutically effective amounts of one or more active pharmaceutical ingredients such that they are uniformly present throughout the formulation and are effectively delivered without the use of an alcohol in the formulation.

Foamable compositions offer advantages over ointments and creams for topical administration of pharmaceuticals. While hydrophobic foamable compositions are known, it is far from simple or obvious to produce hydrophobic waterless foamable compositions that when released produce foams of quality suitable for pharmaceutical or cosmetic application. On a further level, having realized a carrier that will produce a hydrophobic waterless foam of quality there is an additional difficulty to be overcome, namely how to adapt the formula and achieve a uniform formulation, which can accept a range of various active pharmaceutical and cosmetic agents such that the composition and active agent are stable and the foam produced remains of quality. Specifically, one of the challenges in preparing such waterless or substantially waterless foamable compositions is ensuring that the active pharmaceutical or therapeutic agent does not react, isomerize or otherwise break down to any significant extent during is storage and use. Particularly, there remains an unmet need for improved, easy to use, stable and non-irritating foam formulations, with unique therapeutic or beneficial properties containing a stable or stabilized active pharmaceutical or cosmetic agent.

Silicones are hydrophobic substances that offer unique cosmetic properties. They are tasteless, essentially odorless, non-greasy and non-stinging; they are used as a base fluid in many personal care products, with excellent spreading and easy rubout and lubrication properties. Volatile silicone compounds are a specific class of silicones, used in dermal formulations to condition the skin, while reducing the greasy feel of other oils in the formulation. However, one of the principal hindrances to the use of silicones in foam formulations is their known antifoaming effect, especially when included in the formulation in substantial quantities. More specifically, silicones are known for being efficient foam control agents and can prevent foam formation or cause foam to collapse rapidly. Silicone fluids can, for example, enter into the foam lamella and displace the foam stabilizing surfactants from the interphase. The foam lamellas are therefore destabilized and burst resulting in foam collapse. Thus, silicones are essentially contra-indicated for the preparation of foamable carriers and compositions. Nevertheless, because of the favorable properties of silicones, there is still an unmet need to develop foamable formulations incorporating silicone that can produce easy to use good quality foam, especially in substantial quantities.

In general terms foam formed from hydrophobic waterless or substantially waterless compositions may by their inherent nature be less firm or inherently weaker than water based emulsion compositions. Thus, not only are silicones inherently unsuitable for forming foamable compositions but it may additionally go against the grain to try and use them in waterless compositions.

US Patent Publication No. 2008/0031908 describes an aerosol product containing an oily composition containing at least one oil, and at least one hydrocarbon compound (notably, a paraffin or a fatty acid amide) having a melting point greater than or equal to 30° C. (i.e., a solid at room temperature), the compound being in the form of solid particles and one or more propellants. Hydrocarbon solid particles were required to provide a fine bubble, stable foam.

US Patent Publication No. 2005/0287081 (corresponding to International Patent Publication No. WO 2006/031271) describes a topical pharmaceutical aerosol foam containing high levels of liquid silicones to enhance cosmetic elegance, containing five essential ingredients: (1) a lipophilic compound or combinations of lipophilic compounds; (2) a liquid silicone or a combination of liquid silicones; (3) a foaming agent, which is selected from the group consisting of mono, di, tri esters of sorbitol and fatty acids; (4) an active agent; and (5) a propellant. The formulations described in the publication contain less than 60% liquid oil and significant levels of liquid silicone, indicating that foamable compositions containing very high levels of liquid oil were not achieved. Notably, the foam product of the formulations described in US 2005/0287081 is prone to collapse quickly as illustrated below in the Examples, which is also undesirable for a topical foam formulation.

U.S. Pat. No. 3,770,648 teaches that solid silicone resin must be present in quantities to produce a quick breaking anhydrous foam.

Foams are complex dispersion systems which do not form under all circumstances. Slight shifts in foam composition, such as by the addition of active ingredients, may destabilize the foam. Foams are very complex and sensitive systems and are not formed at will. Mere addition of basic ingredients like oil, surfactant and propellant is far from sufficient to produce foams of quality that are homogenous, stable, breakable upon mechanical force and can be used to provide a shelf stable pharmaceutical or cosmetic composition. Small deviations may lead to foam collapse. Much consideration needs to be given to facilitate the introduction of an active agent, such as examining compatibility and non reactivity with the various excipients and container and determining shelf life chemical stability.

Neubourg (US 2006/0099151), for example, notes that the stability of foam is strongly dependent on the specific composition of the foam forming components, so that even small deviations in the composition may lead to a collapse of the foam. Gordon et al. (U.S. Pat. No. 3,456,052). also teaches that one cannot generate a good quality foam by simply adding a propellant to a mixture of components:

The term "foam" is a general term that encompasses a range of substances. Accordingly, the context in which "foam" is discussed must be examined carefully. The type and quality of the foam is of critical importance. There are many different types of foams and within each foam type there are many levels of qualities. For example, the froth on the head of beer, lather of shampoo, and lather of shaving cream have been loosely described as foam but all are different from one another. At one end of the cosmetic or pharmaceutical foam spectrum the foam can be long lasting and essentially not readily breakable like shaving foams. At the other end of the spectrum the foam can be quick breaking and collapses upon release.

Thermolabile foams are an example of type of quick breaking foam. They can contain significant amounts of thermolabile substances that aid their collapse upon being exposed to an increased temperature for example when applied to a body surface at 37 C. Upon being exposed to the higher temperature they collapse rapidly. Examples are foam formulations that comprise significant amounts of volatile solvents.

Breakable foam is a specialized type of foam. It is a low density foam that is stable on release at least in the short time span of several minutes, which facilitates application to a target area; but can break readily upon the application of shear force such as gentle rubbing to spread easily over a target surface. It is not thermolabile (and does not melt at skin temperature) and nor does it display late or long delayed expansion over minutes. In some embodiments, the compositions described herein produce breakable foams.

Some foams expand slowly whilst others do so quickly. Some foams foam immediately and some demonstrate delayed foaming. Some require mechanical lathering and some expulsion by propellant. Whilst they all fall under the so called term "foam" and may appear to have some common ingredients the results and properties of these products are different.

A suitable foamable formulation for a particular application may present challenges at several levels. For example, a foam formulation may require a stable pre foam formulation; a stable pre foam propellant formulation (e.g., a foamable carrier) and ultimately delivery an effective measured amount of active agent to a target. Each of these objectives poses its own unique challenges.

The pharmaceutical and cosmetic foams discussed herein are generated in general terms by manufacturing a suitable foamable carrier composition and loading the carrier in a pressurized valved canister with an appropriate propellant. Upon expelling the canister contents a foam can be released. The type, nature and quality of the foam depends inter alia on the carrier composition, the active agent, the propellant and the method of manufacture and storage. Making a stable (physically and chemically) formulation that can be stored in a canister with a propellant that remains stable and can produce a breakable foam of quality on release is far from trivial.

An additional difficulty frequently encountered with propellant foams is their inability to dispense a uniform application of the medically active ingredient throughout the use of the entire aerosol container. This is particularly due to the fact that the active material is not stably dispersed in the foamable composition so that it will have a tendency to settle to the bottom. Further, the dispersed material will sometimes clog the spray dispensing valve to further interfere with the uniform dispensing of the medicament.

SUMMARY

There remains an unmet need for improved, easy to use, stable and non-irritating oil based foam formulations, with unique physical, therapeutic or beneficial properties containing a stable or stabilized active pharmaceutical or cosmetic agent. Moreover, there is an unmet need for waterless and substantially oil based waterless carriers and foam formulations with liquid silicone, which have a good or special skin feeling and which provide many of the desirable attributes of water based emulsions and foams, such as pleasant feeling, absence of stickiness, good spreadability, relatively quick absorption, absence of shine and reduced oily sensation Compositions formulated using a base comprising an oil combined with liquid silicones to produce waterless formulations are investigated and developed herein as pharmaceutical and cosmetic waterless carriers suitable for delivery of a wide range of active agents despite the defoaming properties of silicones. In particular, such carriers that are substantially a single phase and, in some embodiments, are substantially free of particles. Moreover such carriers are ideal for oil soluble active agents and can nevertheless carry as a homogenous suspension substantial amounts of oil insoluble active agents.

In one aspect, a waterless foamable pharmaceutical composition including a foamable carrier and at least one liquefied or compressed gas propellant is disclosed. The foamable carrier includes: (i) about 60% to about 95% by weight of at least one liquid oil; (ii) a silicone; and (iii) at least one foam stabilizing agent. The foamable carrier is substantially a single phase. The foam stabilizing agent is selected from the group consisting of about 0.01% to about 25% by weight of at least one surface-active agent alone or in combination with a foam adjuvant; about 0% to about 5% by weight of at least one polymeric agent alone or in combination with a foam adjuvant and mixtures thereof. The ratio of the foamable carrier to the propellant is 100:03 to 100:35.

In some embodiments, the waterless foamable pharmaceutical composition includes, by weight: (i) about 60-90% mineral oil; (ii) about 1-15% of one or more of cyclomethicone; a mixture of cyclohexasiloxane and cyclopentasiloxane, cyclytetrasiloxane, dimethiconol, phenyl trimethicone, stearyl dimethicone or mixtures thereof; (iii) about 1-8% glycerol monostearate; and (iv) about 1-8% myristyl alcohol or cetostearyl alcohol; and the composition is essentially free of water.

In another aspect, a waterless foamable pharmaceutical composition is provided. The composition includes a foamable carrier and at least one liquefied or compressed gas propellant. The foamable carrier includes:
a) about 60% to about 95% by weight of at least one liquid oil;
b) a silicone; and
c) about 0.01% to about 25% by weight of a monoglyceride, diglyceride, or triglyceride, or a mixture thereof, wherein the side chain of the monoglyceride, diglyceride, or triglyceride is a saturated hydrocarbon.
The foamable carrier is substantially a single phase; and the ratio of the foamable carrier to the propellant is 100:03 to 100:35.

According to some embodiments, the fatty acid side chain of the monoglyceride, diglyceride, or triglyceride, or a mixture thereof, contains at least 8 carbon atoms. According to some embodiments, the monoglyceride, diglyceride, or triglyceride, or a mixture thereof, is a stearic-acid derived ester. According to some embodiments, the monoglyceride, diglyceride, or triglyceride, or a mixture thereof is glycerol monostearate or glycerol palmitostearate.

In some embodiments, the silicone used in the compositions described herein is a cyclic silicone, a branched silicone, a polar silicone or a mixture thereof. Exemplary cyclic silicones include, without limitation siloxane compounds having 4-6 Si—O groups in its backbone. In some embodiments, the cyclic silicone is a cyclomethicone. Exemplary branched silicones include, without limitation, phenyl trimethicone, stearyl methicone, cetyl dimethicone, caprylyl methicone, PEG/PPG 18/18 dimethicone, and mixtures thereof. Exemplary polar silicones include, without limitation dimethiconol or PEG/PPG 18/18 dimethicone In some embodiments, the at least one liquid oil used in the compositions described herein comprises mineral oil. Non-limiting examples of oils for use in the foamable carriers described herein include mineral oil, MCT oil, liquid paraffin, vegetable oil, essential oil, organic oil, lipid, or a mixture thereof. In some embodiments, the oil is a mixture of light mineral oil and heavy mineral oil. In some embodiments, the weight ratio of the heavy mineral oil to the light mineral oil ranges from about 1:5 to about 25:1.

In some embodiments, the foamable carriers described herein further comprise an emollient. Examples of emollients for use in the compositions described herein include, without limitation, coglycerides, PPG 15 stearyl alcohol, octyldodecanol, isopropyl myristate, diisopropyl adipate, cetearyl octanoate isohexadecanol, diisopropyl adipate and mixtures thereof.

In some embodiments, the foamable carriers described herein further comprise a solid wax or solid oil. Exemplary solid wax or oil include, without limitation solid paraffin, hydrogenated oil, hydrogenated emollient, palmitic acid, stearic acid, arachidic acid, behenic acid and mixtures thereof.

In some embodiments, the foam adjuvant used in the compositions described herein is a solid. Nonlimiting examples of solid foam adjuvants include a solid fatty alcohol selected from the group consisting of stearyl alcohol, cetyl alcohol, cetostearyl alcohol, myristyl alcohol, palmitoleyl alcohol, arachidyl alcohol, benzyl alcohol and mixtures thereof. In some embodiments, the foam adjuvant comprises oleyl alcohol.

In some embodiments, the surface active agent used in the compositions described herein is a stearic acid derived ester. In other embodiments, the surface active agent is monoglyceride, diglyceride, or triglyceride, wherein the side chain of the monoglyceride, diglyceride, or triglyceride is a C8-C24 saturated hydrocarbon. Exemplary surface active agents include, without limitation, glycerol monostearate, glycerol palmitostearate, PEG 100 Stearate, Montanov L, Montano 68, PPG 15 stearyl ether or a mixture thereof.

In some embodiments, the surface active agent used in the compositions described herein is a solid.

In some embodiments, the weight ratio of surface active agent to silicone in the compositions described herein ranges from about 1:1 to about 1:4.

In some of the compositions described herein, (i) the liquid oil consists essentially of mineral oil; (ii) the silicone is present in the foamable carrier in an amount of about 0.5% to about 15% by weight; and (iii) the at least one stabilizing agent is glycerol monostearate and is present in the foamable carrier in an amount of about 0.01% to 25% by weight.

In some embodiments the waterless foamable pharmaceutical compositions described above also include an active agent. In some embodiments, the active agent is soluble in the liquid oil, the silicone, the surfactant or the composition. In some embodiments, the foamable carrier including the active agent forms a substantially homogenous suspension.

Exemplary active agents include active herbal extracts, acaricides, age spot and keratose removing agents, allergen, analgesics, local anesthetics, antiacne agents, antiallergic agents, antiaging agents, antibacterials, antibiotic agents, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, antiwrinkle agents, antipruritics, antipsoriatic agents, antirosacea agents antiseborrheic agents, antiseptic, antiswelling agents, antiviral agents, anti-yeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins A, B, C, D, E and K and their derivatives, wound healing agents, wart removers and mixtures thereof.

In some embodiments, the active agent is a tetracycline antibiotic agent. Exemplary tetracycline antibiotic agents include, without limitation minocycline or doxycycline.

Nonlimiting examples of active agents include acyclovir, azaleic acid, clindamycin phosphate, pimicrolimus, diclofenac potassium; calcipotriol, calcitriol, vitamin A acetate, betamethasone 17-valerate, alpha tocopherol, imiquimod, ciclopiroxolamine, and mixtures thereof.

A method of delivering an active agent to a patient in need of treatment, the method including administering a foamable pharmaceutical composition described herein to a skin surface, a mucosal surface, or a body cavity is also disclosed.

A method for treating skin or a mucosal surface including administering to the skin or mucosal surface a pharmaceutically effective amount of a foamable pharmaceutical composition described herein is disclosed.

A method for treating, ameliorating or preventing a disorder including administering to a target site a pharmaceutically effective amount of a foamable pharmaceutical composition described herein is disclosed. In some embodiments, the methods for treatment described herein include a combination of at least two active agents. In some embodiments, the target site is selected from the group consisting of the skin, a body cavity, a mucosal surface, the nose, the mouth, the eye, the ear canal, the respiratory system, the vagina and the rectum.

In some embodiments, the waterless foamable pharmaceutical compositions described herein produce a resultant foam that displays all of the following characteristics
 a. at least of good quality;
 b. does not collapse immediately upon release;
 c. is breakable on mechanical shear;
 d. has a density below about 0.2 g/ml; and
 e. has a collapse time in excess of about 180 seconds.

In some embodiments, the waterless foamable pharmaceutical compositions described herein produce a resultant foam that displays all of the following characteristics:
 a. at least of good quality;
 b. does not collapse immediately upon release;
 c. is breakable on mechanical shear;
 d. has a viscosity below about 13,000 cps;
 e. has an average bubble size below 200 microns;
 f. has a hardness between about 5 to about 35 and
 e. has a collapse time in excess of about 180 seconds.

In another aspect, a method for preparing a substantially single phase, waterless foamable pharmaceutical composition is provided. The method includes the steps of:
 (a) combining about 60% to about 95% by weight of at least one liquid oil with at least one foam stabilizing agent at a temperature of at least about 50° C.;
 (b) rapidly cooling the combination of one liquid oil and at least one foam stabilizing agent to less than 40° C.;
 (c) adding a silicone to the cooled combination to make a prefoam formulation; and
 (d) combining the prefoam formulation with a compressed gas propellant in a weight ratio of 100:3 to 100:35.

In the method described above, the foam stabilizing agent is selected from the group consisting of about 0.01% to about 25% by weight of at least one surface-active agent alone or in combination with a foam adjuvant; about 0% to about 5% by weight of at least one polymeric agent alone or in combination with a foam adjuvant and mixtures thereof. The method for preparing a substantially single phase, waterless foamable pharmaceutical composition is useful for preparing the pharmaceutical compositions and foamable carriers described herein.

In another aspect, a method for preparing a substantially single phase, waterless foamable pharmaceutical composition is provided. The method includes the steps of:
 (a) preparing a prefoam formulation by combining at a temperature of at least about 50° C.:
 about 60% to about 95% by weight of at least one liquid oil; a silicone; and at least one foam stabilizing agent;
 (b) rapidly cooling the prefoam formulation to less than 40° C.; and
 (c) combining the prefoam formulation with a compressed gas propellant in a weight ratio of 100:3 to 100:35.

The foam stabilizing agent is selected from the group consisting of about 0.01% to about 25% by weight of at least one surface-active agent alone or in combination with a foam adjuvant; about 0% to about 5% by weight of at least one polymeric agent alone or in combination with a foam adjuvant and mixtures thereof.

In some embodiments of the preparation methods described herein, the cooling step is carried out by placing the combination of one liquid oil and at least one foam stabilizing agent in an ice bath, in an alcohol water bath or in a water bath or jacket.

In some embodiments of the preparation methods described herein, the combination of one liquid oil and at least one foam stabilizing agent is cooled at a rate of at least about 5 degrees/minute.

In some embodiments of the preparation methods described herein, the combination of one liquid oil and at least one foam stabilizing agent is cooled to a temperature of at least about 25° C.

BRIEF DESCRIPTION OF THE DRAWING

FIG. 1 is a color photograph of the foamable carrier prepared according to Example 22G.

DETAILED DESCRIPTION

Oil-based, foamable compositions containing silicone are described herein. Surprisingly, the silicone containing compositions are single-phase and exhibit good stability. While oil-based foams are known in the art, it is generally understood that these foams are highly unstable. For example, oil-based foams typically drain shortly after dispensing (e.g., 20-30 seconds following dispensing), leading to subsequent collapse of the foam. Accordingly, oil-based foams are considered to lack stability and are not considered suitable for many uses, including as pharmaceutical compositions for topical administration. In contrast, the oil based foamable compositions described herein generate foams that exhibit excellent stability, as demonstrated by prolonged time to collapse. For example, the foam generated from the compositions described herein is at least short term stable and can be resilient to collapse for at least 2-3 minutes and frequently for 5 minutes after dispensing, at 36° C.

Moreover, the oil-based foamable compositions described herein are single phase compositions. It is conventionally understood in the art that good quality foams require the use of an emulsion. Exemplary emulsions typically used to produce foams include oil-in-water and water-in-oil emulsions. The foamable compositions described herein, however, are single-phase compositions, exhibiting minimal or no partitioning between phases. As a result, the foamable compositions, as well as the resulting foams, are substantially uniform. Thus, active agents are suspended or dissolved uniformly in the foams produced from the compositions, and there is no concern that the active agent is concentrated in a particular phase.

It was unexpectedly observed that quality foams with an oil/silicone oil based single phase waterless formulation are produced when one or more of the following conditions are met:

I. Presence of three ingredients: oil, surfactant and silicone, as a single phase. In a particular embodiment the surfactant is glycerol monostearate, alone or glycerol palmitostearate alone or either one in combination with PEG 100 stearate.

II. A silicone which is capable of generating stearic hindrance or molecular repulsion between itself and the oil/surfactant structure. Unexpectedly, the structure of silicone appears to be highly significant to the creation of stable foams.

III. A ratio between surfactant and silicone ranging from about 1:1 to about 1:4, such as about 1:1; about 4:5; about 1:2; about 3:5; about 1:3; about 2:5 and about 1:4 and any ratio between any of the aforesaid ratios.

IV. In certain embodiments, rapid cooling of the compositions during their preparation is important improve foam quality. When rapid cooling is used, in contrast with slow cooling, it frequently results in a clear improvement of foam quality. In some highly complex formulations with many excipients the advantages of fast cooling are more subtle and can be reflected in parameters like viscosity, appearance and foam quality.

V. Preparing the foamable composition using both slow and rapid cooling procedures resulted in high quality foam.

In certain embodiments the concentration of the surfactant, the oil and the silicone and any other ingredients should be selected so that the composition, after filling into aerosol canisters, is flowable, and can be shaken in the canister. In one or more embodiments, the concentration of the surfactant, the oil and the silicone are selected such that the viscosity of the composition, prior to filling of the composition into aerosol canisters, is less than 13,000 CPs, and more preferably, less than 10,000 CPs, preferably below about 9000, more preferably below about 6000 cps. In one or more embodiments the concentration of the surfactant, the oil and the silicone and any other ingredients should be selected so that the composition produces a foam of quality preferably at least about of good quality. In one or more embodiments, the concentrations of the surfactant, the oil and the silicone are selected such that the average bubble size should be below about 200 microns, preferably below 150 and more preferably below 100 microns. In one or more embodiments, the concentrations of the surfactant, the oil and the silicone are selected such that the foam density is below about 0.2 and preferably below about 0.1 g/ml or in the range of about 0.07 to about 1.5 g/ml. In one or more embodiments, the concentrations of the surfactant, the oil and the silicone are selected such that the foam hardness in the range of about 5 to about 35. In one or more embodiments the foam is of at least about good quality, the bubble size is below 150 microns and the density is between 0.07 and 1.5.

In certain embodiments the concentration of the oil is mineral oil, In one or more embodiments the mineral oil is a mixture of mineral oils. In certain embodiments the mixture is a mixture of light and heavy mineral oils. In one or more embodiments the ratio of heavy to light mineral oil is from about 1:5; about 2:5, about; 5:11; about 1:2; about: 4:7; about 3:5; about 2:3; about 3:4; about; 5:6; about 1:1; about 6:5; about 4:3; about 3:2; about 5:3; about 7:4; about 2:1; about 11:5; about 5:2; about 5:1; about 10:1; about 15:1; about 20:1 and about 25:1 and any ratio between any of the aforesaid ratios. In one or more embodiments the ratio range of heavy to light mineral oil is from about 1:5 to about 25:1; and preferably in the range of about 2:5 to about 5:1.

Without wishing to be bound by a particular theory, it is believed that in certain embodiments oil-based foams are stabilized by the presence of a silicone in the foamable composition. In particular, the silicone is present in the composition in combination with a high concentration of liquid oil (greater than about 60%) and a stabilizing agent. In general terms in preparing the formulation the oil and surfactant are typically first combined and then the silicone is introduced. It is thought, without being bound by any theory, that silicones having the ability to generate stearic hindrance are less able to penetrate the already established surfactant/oil structure. Accordingly, it is thought that these types of silicones have a diminished destabilizing effect on the resulting foam composition than silicones that are able to penetrate the intermingled chains of the surfactant/oil structure. It follows that by selecting silicones that are better able to generate stearic hindrance such silicones are more likely to have a lesser destabilizing effect and vice versa. Thus, in one embodiment, the silicone is a cyclic silicone. In a further embodiment, the silicone includes hydrophobic side chains.

In a further aspect, it is thought that molecular repulsion plays a role in the stabilizing effect, either alternatively or in addition to the role of stearic hindrance. Silicones which are less likely to be repulsed by the surfactant oil/structure are more likely to destabilize the surfactant/oil structure and vice versa. So for example silicones with hydrophilic (e.g., polar) moieties are more likely to repulse hydrophobic oil and/or hydrophobic side chains of some surfactants, such as monoglycerides (e.g., glycerol monostearate). Accordingly, in one or more preferred embodiments the silicone is a branched chain silicone or a silicone having one or more hydrophilic or polar moieties.

In a particular embodiment, the silicone is cyclomethicone, cyclotetrasiloxane, cyclohexasiloxane, dimethiconol, phenyltrimethicone, or stearyl dimethicone.

Thus, the oil-based foams in certain embodiments are believed to be stabilized by the presence of a cyclic silicone and/or a linear highly substituted silicone in the foamable composition. The cyclic silicone is present in the composition in combination with a high concentration of liquid oil (e.g., greater than about 60%) and a stabilizing agent. In some embodiments, the cyclic silicone is of low viscosity. In some embodiments, the cyclic silicone is volatile. In one embodiment, the cyclic silicone is cyclomethicone.

In some embodiments, the foamable compositions described herein are free of linear (i.e., non-branched) silicones. In some embodiments, the foamable compositions described herein are free of hydrophilic silicones (i.e., containing hydrophilic or polar groups (e.g., dimethiconol). In other embodiments the foamable compositions include hydrophilic silicones, such as dimethiconol, which with glycerol monostearate and oil produced high quality foam.

Further, and again without wishing to be bound by a particular theory, the oil-based foams are believed to be stabilized by the presence of a cyclic volatile silicone in the foamable composition. The cyclic volatile silicone is present in the composition in combination with a high concentration of liquid oil (e.g., greater than about 60%) and a stabilizing agent. In an embodiment the volatile silicone is cyclomethicone. In some embodiments, the volatile cyclic silicone is used in combination with another silicone. In certain embodiments the second silicone is a cyclic silicone. For example, when cyclomethicone was used in combination with cyclohexasiloxane it produce a foam of quality. In further embodiments, the volatile silicone is cyclic. In further embodiments, the volatile silicone is non cyclic provided it provides steric or repulsive hinderance by having branched or polar groups.

In addition, without wishing to be bound by a particular theory, the oil-based foams are believed to be stabilized by the presence of a low viscosity silicone in the foamable composition. The low viscosity silicone is present in the composition in combination with a high concentration of liquid oil (e.g., greater than about 60%) and a stabilizing agent. In some embodiments, the low viscosity silicone is volatile. In further embodiments, the low viscosity silicone is cyclic. In an embodiment the lower viscosity silicone is cyclomethicone.

As shown in the Examples, using long, straight-chain dimethicone instead of cyclomethicone in the foamable compositions results in a lower quality foam. It is believed that dimethicone, which has a hydrophobic chain-like structure, may be located or trapped between the hydrophobic chains of the liquid oil, thereby destabilizing the hydrophobic-hydrophobic interactions between the chains of the oil. This destabilization—without being bound by any theory—is thought to decrease the formulation viscosity and result in a poorer quality foam, e.g., due to the quicker draining of the less viscous formulation.

In contrast, cyclomethicone, which has a cyclic structure, has a lower affinity for the long hydrophobic chains of the liquid oil. Thus, as described above with regard to stearically hindered silicones, it is thought that cyclomethicone does not destabilize the liquid oil structure and helps to maintain high formulation viscosity, thus providing improved foam qualities.

Also present in the composition and contributing to the foam stability is a surface active agent. In some embodiments, the surface active agent is an ester of a C8-C24 saturated hydrocarbon. In some embodiments, the surface active agent is a stearic acid derived ester. The surface active agent is situated at the gas/liquid interface of the foam, lowering the surface tension at the interface between the gas bubbles and the surrounding oil phase. This property is beneficial for foam formation and also for the prevention of bubble coalescence, thus further stabilizing the foam.

Similarly, the cyclic silicone is located at the gas/liquid interface. Its surface tension assists in stabilizing the foam by lowering surface tension at the interface. Moreover, with regard to volatile silicones, the volatility is thought to improve the liquid flow at the gas/oil interface and also enhance the bubble film elasticity. Both of these factors contribute to substantially reduce bubble coalescence and foam collapse.

In one or more embodiments there is provided a substantially waterless foamable composition suitable for external or body cavity administration of an active agent, comprising a foamable carrier and at least one liquefied or compressed gas propellant wherein the foamable carrier comprises:

about 60% to about 95% by weight of at least one liquid oil;
at least one liquid silicone;
at least one least one foam stabilizing agent;
wherein the foamable composition is substantially a single phase, in which the active agent is capable of being dissolved or suspended substantially uniformly;
wherein the foam stabilizing agent is selected from the group consisting of about 0.1% to about 25% by weight of at least one surface-active agent (which is not primarily a sorbitan ester of a fatty acid) alone or in combination with a foam adjuvant; about 0% to about 5% by weight of at least one polymeric agent alone or in combination with a foam adjuvant and mixtures of at least one surface-active agent and at least one polymeric agent with or without a foam adjuvant; and
wherein the ratio of the foamable carrier to the propellant is 100:03 to 100:35.

A method of making the foamable, single-phase, oil-based compositions described herein is further provided. As described herein, the compositions are generally prepared by first combining the liquid oil with the surface active agent at an elevated temperature, followed by cooling to room temperature. In one embodiment, the components are combined at a temperature of at least about 50° C., at least about 55° C., at least about 60° C. or at least about 65° C. In another embodiment, the components are combined at a temperature between about 50° C. to about 65° C.

In one embodiment, the oil/surface active agent combination is cooled rapidly, by exposing the combination to cold temperatures, e.g., less than about 40° C., less than about 30° C., less than 25° C., or less than about 20° C., or less than about 15° C., or less than about 10° C., or less than about 5° C., or less than about 0° C. or less than about minus 5° C. until it reaches the desired temperature. In one embodiment, rapid cooling is effectuated by placing the combination in an ice bath until it reaches the desired temperature. In another embodiment it is placed in an alcohol water bath. In another embodiment it is placed in a water bath. In a preferred embodiment the cold water bath is blow about 20° C. In a preferred embodiment the ice bath is blow about 4° C. In a preferred embodiment the alcohol water bath is blow about minus 5° C. Without wishing to be bound by a particular theory it is thought that rapid cooling helps to stabilize the formulation by "locking" the hydrophobic ingredients together and stabilizing the oil surfactant structure. The rate of cooling for the rapid cooling procedure ranges from about 2 degrees/minute to about 15 degrees/minute, from about 4 degrees/minute to about 15 degrees/minute or 4 degrees/minute to about 8 degrees/minute. In some embodiments, the rate of cooling is greater than about 2 degrees/minute, about 3 degrees/minute, about 4 degrees/minute, about 5 degrees/minute, about 10 degrees/minute, or about 15 degrees/minute. In an alternative embodiment, the oil/surface active agent combination is cooled slowly. In one embodiment, slow cooling is performed by keeping the mixture at room temperature until it reaches the desired temperature.

In another embodiment, the oil/surface active agent combination is cooled slowly. In one embodiment, rapid cooling is effectuated by holding the combination at room temperature until it reaches the desired temperature. The rate of cooling for the slow cooling procedure ranges from less than about 3 degrees/minute to less than about 0.4 degrees/minute, or from less than about 2 degrees/minute to less than about 1 degrees/minute. In some embodiments, the rate of cooling is less than about 5 degrees/minute, about 4 degrees/minute, about 3 degrees/minute, about 2 degrees/minute, or about 1 degrees/minute.

In formulations containing silicone, the silicone is added prior to cooling, during cooling, or at the end of the cooling step (when the combination is at or near its desired temperature). In one embodiment, the silicone is added after the combination has reached room temperature. In another embodiment, the silicone is added once the combination has reached a desired temperature. In another embodiment, the silicone is added when the combination is within 5° C. of the desired temperature. For example, in some embodiments, the silicone is added after the combination is cooled to a temperature of not more than 45° C., not more than 40° C., not more than 35° C., not more than 30° C., or not more than 25° C. In some embodiments, the silicone is added after the combination is cooled to a temperature between about 15° C. to about 25° C., between about 20° C. to about 25° C., between about 25° C. to about 45° C., between about 40° C. to about 45° C., between about 25° C. to about 35° C., or between about 25° C. to about 30° C. Following addition of the silicone, the formulation is further cooled or warmed, to room temperature, either by slow cooling (i.e., exposure to room temperature) or by rapid cooling, as described above. In some embodiments, the silicone is added in different portions at different temperatures during the process.

In some embodiments, formulations prepared by fast cooling result in improved foam quality, smaller bubble size, viscosity, and density.

Definitions

All % values are provided on a weight (w/w) basis.

The term "waterless", as used herein, means that the composition contains no or substantially no, free or unassociated or absorbed water. Similarly, "waterless" or "substantially waterless" compositions contain at most incidental and trace amounts of water.

The term "unstable active agent" as used herein, means an active agent which is oxidized and/or degraded within less than a day, and in some cases, in less than an hour upon exposure to air, light, skin or water under ambient conditions.

The identification of a "solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

The pharmaceutical carriers and compositions described herein are suitable for dermal or external application of an stable or unstable active agent. Typically, unstable agents break down upon exposure to air, water vapor or upon contact with the skin. The hydrophobic, oil-based carriers described herein provide stable formulations of unstable agents, which are active in situ and, and are stable over a time period of at least 1-5 minutes after application. The carriers and compositions are substantially non-aqueous, and provide not only a soothing effect to the skin, but also provide a therapeutic local and/or systemic effect from the active agent.

In one or more embodiments the composition comprises a pharmaceutical or cosmetic active agent. In certain embodiments, the active agent is unstable in the presence of water, and in such cases the presence of water in the composition is clearly not desirable.

The active agent may be insoluble or fully or partially soluble in the composition and to the extent it is insoluble it may be provided in a substantially homogenous insoluble suspension.

The at least one liquid oil may be selected from a mineral oil a vegetable oil, a MCT oil, an essential oil and organic oil, a hydrogenated castor oil and lipids and mixtures thereof.

The liquid oil may further contain an emollient or a hydrophobic solvent. In some embodiments the liquid oil may contain a solid oil or wax.

In an embodiment there is provided a waterless foamable pharmaceutical composition, wherein said at least one liquid oil is a mineral oil.

In an embodiment there is provided a waterless foamable pharmaceutical composition, wherein the liquid silicone is unmodified.

In an embodiment there is provided a waterless foamable pharmaceutical composition, wherein said oil is selected from mineral oil, hydrogenated castor oil and MCT oil.

In an embodiment there is provided a waterless foamable pharmaceutical composition, wherein the emollient is selected from isopropyl myristate, PPG-15 stearyl ether, octyldodecanol, Isohexadecanol, diisopropyl adipate, and Cetearyl Octanoate.

Some compositions comprise at least one hydrophobic solvent selected from the group consisting of mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; and essential oils.

The foamable carrier may further including a foam adjuvant selected from the group consisting of a fatty alcohol, a fatty acid and a hydroxyl fatty acid.

In one or more embodiments the liquid oil is substantially free of particles. In a preferred embodiment the liquid oil is free of particles as determined by normal microscopic examination. In other words the foamable carrier prior to addition of active agent is substantially a single phase, and preferably a single phase. In one or more embodiments the foamable composition after addition of active agent is substantially a single phase, preferably a single phase. In yet other embodiments the foamable composition after addition of active agent is substantially a homogenous suspension of active agent.

Preferably, the pharmaceutical composition has the following property: a foam quality of at least good up to excellent; and at least one other property selected from: specific gravity in the range of about 0.05 gr/mL to about 0.20 gr/mL; a foam texture of a very fine creamy foam consistency to a fine bubble structure consistency; a sustainability of more than 95% for at least one minute upon release thereof to a surface from an aerosol can; capable of withstanding at least one freeze thaw cycle without substantial change; having a mean bubble size of less than about 200 micron; and compatibility with the at least one active agent.

In some cases, the foamable pharmaceutical composition has at least four of the properties. In some other cases, the composition has all of the properties.

The target site for the composition includes the skin, a body cavity, a mucosal surface, the nose, the mouth, the eye, the ear canal, the respiratory system, the vagina and the rectum.

In one or more embodiment, the foregoing formulations including an liquid oil are used with a tetracycline antibiotic such as doxycycline or minocycline for the treatment of acne.

The use of an oil-based formulation for the treatment of acne runs counter to conventional approach, which avoid oily bases as exacerbating the underlying acne condition. In contrast, the current formulations moisturize and protect the skin. Initial investigations indicate that waterless hydrophobic preparations have a good "skin feel," are quickly absorbed and are not tacky.

The present invention relates to a foamable pharmaceutical carrier suitable for external administration of an active agent. In some embodiments, the active agent is unstable, particularly water unstable.

Silicone

A "Silicone" is a largely inert compound with a wide variety of forms and uses. Silicones (more accurately called polymerized siloxanes or polysiloxanes) are inorganic-organic polymers with the chemical formula $[R_2SiO]_n$, where R=organic groups such as $(C_1\text{-}C_6)$-alkyl or $(C_1\text{-}C_8)$-aryl groups (e.g., methyl, ethyl, propyl, and phenyl). These materials consist of an inorganic silicone-oxygen backbone ( . . . —Si—O—Si—O—Si—O— . . . ) with organic side groups (side chains) attached to the silicone atoms, which are four-coordinate. In some cases organic side groups can be used to link two or more of these —Si—O— backbones together. By varying the —Si—O— chain lengths, side groups, and crosslinking, silicones can be synthesized with a wide variety of properties and compositions. Their excellent biocompatibility is partly due to the low chemical reactivity displayed by silicones, their low surface energy and their hydrophobicity.

Silicones such as dimethicone, simethicone and simethicone emulsion have found wide application in the manufacture of pharmaceuticals due to their efficient antifoam properties. Dimethicones and simethicones are used as antifoams in anti-flatulent or anti-acid formulations. Silicones in these products help to suppress the formation of foam in the stomach without modifying the gastric pH. This is not surprising as silicones, with their low surface tension (and in particular when compounded with silicon dioxide) are known to destroy foams in many applications, e.g. in petrol, paper pulp or food processing. This makes them contraindicated for use in foamable carriers and compositions and especially in waterless or substantially waterless carriers, compositions and foams. The current application has identified silicones that surprisingly produce stable, fine bubble foams using having a high oil content.

Silicone compounds useful in the compositions described herein are selected for their ability to form a stable, waterless or substantially waterless, single phase foamable composition. Factors to consider in selecting the appropriate silicone compound include the shape and size of the compound, the hydrophilicity or polarity of the compound, viscosity, volatility, surface tension, and interactions with the oil and stabilizing agent (e.g., surface active agent) also present in the composition.

With regard to shape and size, as described previously, silicones that do not inhibit the hydrophobic-hydrophobic interactions of the oil are thought to produce more stable foams. Exemplary silicones of appropriate size and shape include, without limitation, cyclic silicones, such as those having 3 to 6, or 3 to 4 or 3 to 5, (or any of 3, 4, 5, or 6) Si—O groups in the cyclic backbone chain (e.g., siloxanes). In some embodiments, the cyclic silicone is a volatile silicone. In some embodiments, the cyclic silicone is a low viscosity silicone. Exemplary cyclic silicones include, without limitation, cyclomethicone, cyclotetrasiloxane, cyclopentasiloxane (e.g., Cyclomethicone 5-NF), cyclohexasiloxane and a mixture of cyclohexasiloxane and cyclopenasiloxane (e.g., DOW CORNING 246 Fluid (d6+d5)). Other non-limiting examples of silicones of appropriate size and shape are silicones having side groups or side chains. In some embodiments, the side groups are hydrophobic. In some embodiments, the side groups are straight chained, while in other embodiments the side groups are branched. Exemplary side chains include those having 1 to 6, or 2 to 6, or 3 to 6 or 3 to 6 or 5 to 6 carbons or heteroatoms (e.g., O, S, or N) (or any combination thereof). Exemplary linear side chains include, without limitation, methyl, ethyl, propyl, butyl, pentyl, and hexyl. Exemplary branched side chains include, without limitation, isopropyl, isobutyl, and tert-butyl. In one nonlimiting embodiment, the branched side chain is —O—Si$(CH_3)_3$. Nonlimiting examples of silicones having branched side chains are stearyl dimethicone and phenyltrimethicone, cetyl dimethicone, caprylyl methicone, PEG/PPG 18/18 dimethicone the structures of which are as follows:

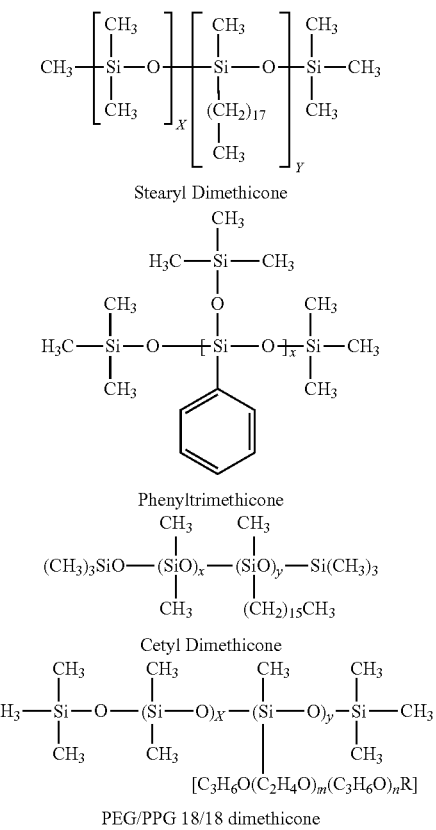

In further embodiments, the side chains are cyclic. Cyclic side chains include aliphatic side chains and aromatic side chains. A nonlimiting example of a cyclic side chain is phenyl.

With regard to silicones having hydrophilic or polar groups, as described previously, silicones that are repulsive with regard to the hydrophobic chains of the oil are thought to produce more stable foams because they do not inhibit the hydrophobic-hydrophobic interactions of the oil. Exemplary hydrophilic or polar groups include oxygen-containing groups, such as carbonyl groups, hydroxy groups, ether, ester, carboxylic groups, which replace one or more methyl groups. The hydrophilic/polar groups are present alternatively in the main chain of the silicone or in a side chain. Nonlimiting examples of a silicone having a hydrophilic group are PEG/PPG 18/18 dimethicone and dimethiconol, the structures of which are:

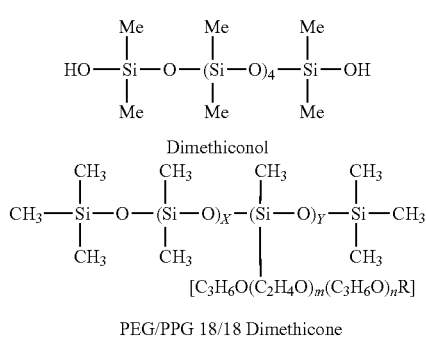

Dimethiconol

PEG/PPG 18/18 Dimethicone

Another type of specific non limiting volatile silicone in accordance with the present invention is a volatile short chain linear alkylmethylsilicone fluid. The volatile short chain linear alkylmethylsilicone fluid has the formula:

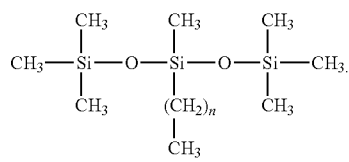

In the above formula, the integer represented by n has a value of five to twelve. Preferably, n has a value of five to eight. Compounds most preferred in terms of this invention are 3-hexyl-1,1,1,3,5,5,5,-heptamethyltrisiloxane and 3-octyl-1,1,1,3,5,5,5-heptamethyltrisiloxane. Measured at twenty-five degrees Centigrade, these two preferred compounds have a viscosity of two Centistokes and five Centistokes, respectively.

Yet another type of volatile silicone in accordance with the present invention is a volatile short chain linear phenylmethylsilicone fluid. The volatile short chain linear phenylmethylsilicone fluid has the formulan:

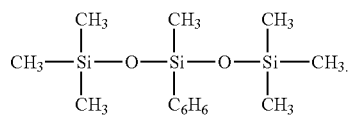

This compound is 3-phenyl-1,1,1,3,4,4,4-heptamethyltrisiloxane.

Further volatile silicone fluids useful in the compositions described herein include, without limitation, are decamethylcyclopentasiloxane (DMCPS) which has a molecular weight of about 370, a refractive index of 1.40, and the formula [(Me$_2$)SiO]$_5$; the compound 3-hexyl-1,1,1,3,5,5,5-heptamethyltrisiloxane (HHMTS) which has a molecular weight of about 306, and a refractive index of 1.41; and the compound 3-phenyl-1,1,1,3,5,5,5-heptamethyltrisiloxane (PH-MTS) which has a molecular weight of about 298 and a refractive index of 1.45. These compounds will be referred to in the examples and in the table below as DMCPS, HHMTS, and PHMTS, respectively, for the sake of convenience.

In an embodiment, the silicone component(s) is selected for particular volatility properties. In one embodiment the silicone is a liquid volatile silicone. By volatile is meant that the silicone or at least part will pass into vapour if left in an open container at normal levels of temperature and pressure.

In some embodiments, the volatile silicone is a cyclic silicone. In some embodiments, the volatile silicone is a siloxane having 3 to 6, or 4 or 5, Si—O groups in the cyclic backbone chain. In some embodiments, the volatile silicone is a low viscosity silicone.

With regard to viscosity and volatility, silicones that have lower viscosity are generally considered to be more volatile. Accordingly, in some embodiments, the silicone is a low viscosity silicone. In an embodiment, a liquid silicone is a low viscosity liquid silicone. Suitable volatile silicone fluids may be cyclic or linear. For example, volatile silicones include, without limitation, silicones having a viscosity of less than about 10, less than about 8, less than about 6, or less than about 5 centistokes at 25° C. In an embodiment the viscosity is between about 10 to about 0.5 cps. In certain embodiments the viscosity is less than about 5 cps. Linear volatile silicones generally have viscosities of less than about five centistokes at 25° C., whereas the cyclic silicones have viscosities of less than about 10 centistokes. Volatile dimethicones are fluids with viscosities of 0.65 to 2 mm$^2$/s of 5.0 mm$^2$/s. A comparison of the viscosity of a volatile silicone, cyclomethicone, with a nonvolatile silicone, dimethicone, is shown in Table 1.

TABLE 1

| INCI NAME | CAS No. | SCIENTIFIC NAME | VISCOSITY |
|---|---|---|---|
| Dimethicone | 9006-65-9 | polydimethylsiloxane | 350 CPS med. weight |
| Cyclomethicone | 541-02-06 | decamethylcyclopentasiloxane | 4 CPS (v. light) |

* to figure CPS by comparison: H$_2$O (water) has a viscosity of 1-5 CPS.

Accordingly, in some embodiments, the silicone is a volatile silicone including, but not limited to (i) a volatile short chain linear silicone fluid having in its molecule only methyl groups, (ii) a volatile cyclic silicone fluid having in its molecule only methyl groups, (iii) a volatile short chain linear silicone fluid having in its molecule both methyl groups and phenyl groups, or (iv) a volatile short chain linear silicone fluid having in its molecule both methyl groups and alkyl groups containing up to twelve carbon atoms, but preferably six, seven, or eight carbon atoms. All of these fluids have a vapor pressure which is less than 0.10 mm Hg, measured at twenty degrees Centigrade and 760 mm pressure.

One type of volatile silicone in accordance with the present invention is a low viscosity methylsilicone fluid. The volatile low viscosity methylsilicone fluid corresponds to the average unit formula $(CH_3)_a SiO_{(4-a/2)}$ wherein a is an integer having an average value of from two to three. For example, representative compounds are cyclopolysiloxane compounds of the general formula $[(CH_3)_2 SiO]_x$, and linear siloxane compounds of the general formula $(CH_3)_3 SiO[(CH_3)_2 SiO]_y Si(CH_3)_3$, in which x is an integer having a value of from three to ten, and y is an integer having a value of from zero to about four.

In some embodiments, the volatile low viscosity methylsilicone fluid contains dimethylsiloxane units and optionally trimethylsiloxane units. In some embodiments, the methylsilicone fluid has a viscosity of less than about ten centistokes.

In some embodiments, the volatile low viscosity methylsilicones have boiling points generally less than about two hundred-fifty degrees Centigrade, and possess viscosities preferably generally less than about ten centistokes measured at twenty-five degrees Centigrade. In some embodiments, the viscosity is 0.65 to 5.0 centistokes. Cyclomethicone has a vapor pressure of 0.015 kPa at 25 C. The cyclopolysiloxane compounds have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin and nail surfaces, and exhibit enhanced spreadability and ease of rub-out when applied. Once applied, the materials evaporate leaving behind no residue.

Methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical. In some embodiments, methylsilicone fluids include, without limitation, hexamethyldisiloxane which has a boiling point of 99.5 degrees Centigrade and the formula $Me_3SiOSiMe_3$; octamethyltrisiloxane which has a boiling point of 152 degrees Centigrade and the formula $Me_3SiOMe_2SiOSiMe_3$; hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $[(Me_2)SiO]_4$; and decamethylcyclopentasiloxane which has a boiling point of 205 degrees Centigrade and the formula $[(Me_2)SiO]_5$.

These methylsilicone fluids may be used alone, or as mixtures in combinations of two or more. Mixtures of the methylsilicone fluids will result in a volatile material having an evaporating behavior different from any one of the individual methylsilicone fluids.

The methylsilicone fluids and methods for their preparation are known in the art.

In addition, with regard to surface tension, silicones that have low surface tension are thought to contribute to the stability of the foams described herein. Similarly, with regard to interaction with the oil and stabilizing agent, silicones that can interact with these components to produce a more stable foam are desired.

In certain embodiments cyclomethicone is used in combination with other silicones. In some embodiments, a combination of silicones having different sizes and shapes, hydrophilicity, polarity, or volatility is selected. For example, in some embodiments, the volatile silicone is a combination of volatile, non-volatile, or partially non-volatile silicones, such that the viscosity of the combination is that is that of a volatile silicone. In certain embodiments, the foamable formulation includes at least a volatile element including at least one volatile or partially volatile silicone and a non-volatile element including at least one non-volatile oil and optionally a non-volatile silicone. Upon application to a surface, one or all of the silicones of the volatile element evaporates and the non-volatile element remains at the site of application.

A description of various volatile silicone oils is found in Todd, et al., "Volatile Silicone Fluids for Cosmetics", 91 Cosmetics and Toiletries, 27-32 (1976), incorporated by In some embodiments, the silicone is a low viscosity silicone. For example, in some embodiments, the silicone has a viscosity of less than about 10 centistokes at 25° C.

In some embodiments, the silicone is not a dimethicone.

In one embodiment the silicone is an unmodified silicone (i.e., not synthetically modified). Unmodified silicones stay on or near the surface of the skin. Not only are the molecules too big to physically enter past the upper living cells—they associate with the upper layer of drying skin—but they also cannot penetrate cell membranes due to their large size. They also dislike both the water and proteins inside cells. Silicones may be used in the foam compositions for topical and body cavity compositions. They evaporate after helping to carry oils into the top layer of epidermis. From there, they may be absorbed by the skin.

Lower molecular weight siloxanes are frequently used due their volatility and generally dry skin feel. The can be important in trying to overcome the particularly dry skin feeling associated with waterless foam compositions. These can include linear as well as cyclic siloxanes. A low molecular weight linear material is hexamethyldisiloxane, $(Me)_3SiOSi(Me)_3$ (HMDS), which is said to have a viscosity of about 0.48 mPa·s.

Inhalation of aerosols of oily or fatty-type materials, including silicones, into alveolar regions of the lung may result in physical disturbances of the lining of the lung with associated effects. This makes the selection of foams as a method of application of silicone containing substances desirable since it should avoid the risk of inhalation when compared to aerosol sprays.

Polysiloxanes have generally poor compatibility with oils, such that the compatibility (solubility) of the polysiloxanes with the oils decreases as the number of dimethylsiloxy units increases. Thus, it is far from straight forward to discover waterless and substantially waterless silicone carriers, compositions and foams which also contain hydrophobic solvents like oils or which also comprise other fatty or greasy substances. Nevertheless successful formulations producing a foam of quality can be achieved with polysiloxanes.

In an embodiment wax silicone or solid silicone is used in combination with liquid silicone. An example is stearyloxytrimethylsilane, $CH_3(CH_2)_{17}OSiMe_3$. The wax silicone will dissolve in the oil carrier and propellant.

Liquid Oil

In some embodiments, the liquid oil is a mineral oil. The mineral oil may be heavy or light or a combination thereof. Exemplary liquid oils also include, without limitation, one or more of a vegetable oil, MCT oil (i.e., medium chain triglycerides, such as caproic (C6), caprylic (C8), capric (C10) and lauric acid (C12)), an essential oil, an organic oil or a lipid. MCT oil may be obtained as a mixture of capric/caprylic triglycerides. In some embodiments, the liquid oil consists essentially of a mineral oil. In some embodiments, the liquid oil consists of a mineral oil. In an embodiment the liquid oil is essentially a mineral oil. In another embodiment it may comprise a majority of mineral oil combined with one or more other oils. In one or more embodiments the liquid oil may further comprise an emollient. In one or more embodiments the liquid oil may further comprise a hydrophobic solvent. In one or more embodiments the liquid oil may further comprise a polypropylene glycol (PPG) alkyl ether such as a PPG stearyl ether for example PPG-15.

In some embodiments, the liquid oil is one or more of mineral oil, MCT oil, liquid paraffin, vegetable oil, essential oil, organic oil, and lipids.

Polypropylene Glycol (PPG) Alkyl Ethers

In the context, a polypropylene glycol alkyl ether (PPG alkyl ether) is a liquid, water-insoluble propoxylated fatty alcohol, having the molecular formula of $RO(CH_2CHOCH_3)_n$; wherein "R" is a straight-chained or branched $C_4$ to $C_{22}$ alkyl group; and "n" is in the range between 4 and about 50.

(PPG alkyl ethers), are organic liquids that function as skin-conditioning agent in pharmaceutical and cosmetic formulations. They possess exceptional emollient effect, side by side with enhanced solvency properties, which facilitates solubilization of active agents in a composition comprising a PPG alkyl ether. PPG alkyl ethers offer the following advantages when used as a component in the foamable composition:

Due to the polypropylene glycol moiety, PPG alkyl ethers possess certain surface active properties and they assist in the coupling of polar and non-polar oils in an emulsion formulation;

PPG alkyl ethers are non-occlusive; offering a long-lasting and velvety feel;

They are chemically stable at extreme pH conditions;

Excellent solvency properties, particularly with difficult to formulate active agents; and When combined with certain surfactants, such as Brij 72 and Brij 721, PPG alkyl ethers form oleosomes and/or liquid crystal structures, which provide long lasting moisturization, excellent spreading as well as prolonged hydration properties.

Exemplary PPG alkyl ethers include PPG-2 butyl ether, PPG-4 butyl ether, PPG-5 butyl ether, PPG-9 butyl ether, PPG-12 butyl ether, PPG-14 butyl ether, PPG-15 butyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-50 oleyl ether, PPG-11 stearyl ether. Preferred PPG alkyl ethers according to the present invention include PPG-15 stearyl ether (also known as Earlamol E®, Unichema), PPG-2 butyl ether, PPG-9-13 butyl ether and PPG-40 butyl ether. PPG alkyl ethers can be incorporated in the foamable composition.

PPG Stearyl Ethers

PPG stearyl ethers function as skin-conditioning and penetration agents in cosmetic formulations.

Polypropylene glycol stearyl ether 15, also known as polyoxypropylene 15 stearyl ether or as "PPG-15", and having a CAS Registry No. of [25231-21-4], is a stearyl ether having about 15 propylene oxide units incorporated in its structure. PPG-15 stearyl ether is a clear liquid, soluble in mineral oil, isopropyl ethers, cottonseed oil, ethanol, isopropanol and hexadecyl alcohol, to name a few, and is particularly useful as a solvent of difficult to formulate ingredients, such as sunscreens, aluminum chlorhydrate salts and skin toners. It is insoluble in water, propylene glycol and glycerin. PPG-15 stearyl ether is an inert and highly stable compound.

PPG stearyl ether also functions as a coupling agent, allowing, for example, the compatibility of polar and non-polar oils with ethanol and perfumes in after shave lotions. It is chemically stable at extreme pH levels and at the same time saturated, providing excellent shelf life stability.

Polymeric Agent

In some embodiments, the composition contains a polymeric agent. The presence of a polymeric agent promotes the creation of a foam having fine bubble structure, which does not readily collapse upon release from the pressurized aerosol can. The polymeric agent serves to stabilize the foam composition and to control drug residence in the target organ. Preferably, the polymeric agent is soluble or readily dispersible in the polyol; or in the mixture of a polyol and an additional solvent.

Non-limiting examples of polymeric agents that are soluble or readily dispersible in propylene glycol are Hydroxypropylcellulose and carbomer (homopolymer of acrylic acid is crosslinked with an allyl ether pentaerythritol, an allyl ether of sucrose, or an allyl ether of propylene, such as Carbopol® 934, Carbopol® 940, Carbopol® 941, Carbopol® 980 and Carbopol® 981.

Other polymeric agents are suitable for use according to the present invention provided that they are soluble or readily dispersible in the polyol; or in the mixture of a polyol and an additional solvent, on a case by case basis.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses. Polyethylene glycol, having molecular weight of 1000 or more (e.g., PEG 1,000, PEG 4,000, PEG 6,000 and PEG 10,000) also have gelling capacity and while they are considered herein as "secondary solvents", as detailed herein, they are also considered polymeric agents.

Mixtures of the above polymeric agents are contemplated.

The concentration of the polymeric agent should be selected so that the composition, after filling into aerosol canisters, is flowable, and can be shaken in the canister. In one or more embodiments, the concentration of the polymeric agent is selected such that the viscosity of the composition, prior to filling of the composition into aerosol canisters, is less than 13,000 CPs, and more preferably, less than 10,000 CPs.

Surface-Active Agents

In the various embodiments, the compositions described herein comprise a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants can be significant in producing breakable forms of good quality. It has been further discovered that the generally thought considerations for HLB values for selecting a surfactant or surfactant combination are not always binding for emulsions and moreover for substantially non-aqueous carriers the usual guidelines are less applicable. For oil based waterless systems HLB values may have little significance other than to indicate the proportion of an amphiphilic molecule that is hydrophobic and therefore potentially more at home in an oil single phase environment. Surfactants can play a significant role in foam formation where the foamable formulation is a single phase composition.

In selecting a suitable surfactant or surfactant combination for use in the substantially single phase formulations described herein selection relates to a multiple of factors including but not limited to solubility and miscibility in the liquid oil and in the silicone to produce substantially a single phase; the ability to form foam of quality; the ability to stabilize the extruded foam; a HLB value which preferably suggests potential compatibility with the liquid oil and the silicone; and solubility of surfactant in the formulation.

In certain embodiments the surfactant can have thickening properties. In certain embodiments the surfactant can effect the viscosity of the pre foam formulation (PFF). In certain other embodiments the surfactant has little or no effect. The concentration of the surfactant agent in combination with the oil and silicone and other ingredients should be selected so that the composition, after filling into aerosol canisters, is flowable, and can be shaken in the canister. In one or more embodiments, the concentration of the surfactant agent is selected such that the viscosity of the composition, prior to filling of the composition into aerosol canisters, is less than 13,000 CPs, and more preferably, less than 10,000 CPs, preferably below about 9000, more preferably below about 6000 cps; In one or more embodiments average bubble size of the resultant foam should be below about 200 microns, preferably below 150 and more preferably below 100 microns; In one or more embodiments foam density is below about 0.2 preferably below about 0.1 g/ml. In one or more embodiments hardness of the resultant foam is in the range of about 5 to about 35.

According to one or more embodiments the composition contains a single surface active agent having an HLB value between about 2 and 9, or more than one surface active agent and the weighted average of their HLB values is between about 2 and about 9.

According to one or more embodiments the composition contains a single surface active agent having an HLB value between about 7 and 14, (preferably about 7 to about 12) or more than one surface active agent and the weighted average of their HLB values is between about 7 and about 14 (preferably about 7 to about 12).

According to one or more other embodiments the composition contains a single surface active agent having an HLB value between about 9 and about 19, or more than one surface active agent and the weighted average of their HLB values is between about 9 and about 19.

In a waterless or substantially waterless environment a wide range of HLB values may be suitable. In one or more embodiments the HLB may not play a role in a single phase system Preferably, the composition contains a non-ionic surfactant. Nonlimiting examples of possible non-ionic surfactants include a polysorbate, polyoxyethylene (20) sorbitan monostearate, polyoxyethylene (20) sorbitan monooleate, a polyoxyethylene fatty acid ester, polyoxyethylene (8) stearate (Myrj 45), polyoxyethylene (20) stearate (Myrj 49), polyoxyethylene (40) stearate (Myrj 52) and polyoxyethylene (100) stearate (Myrj 59); a polyoxyethylene alkyl ether, polyoxyethylene cetyl ether, steareths such as steareth 2, Steareth 21 (Brij 721), polyoxyethylene (23) cetyl ether (Brij38), polyoxyethylene (2) cetyl ether (Brij 52), polyoxyethylene (10) cetyl ether (Brij 56) a sucrose ester, a partial ester of sorbitol and its anhydrides, sorbitan monolaurate, sorbitan monolaurate, a monoglyceride, a fatty acid ester of glycerol, a diglyceride, isoceteth-20, a mono-ester of sucrose with fatty acids, a di-ester of sucrose with fatty acids, and a tri-ester of sucrose with fatty acids. In certain embodiments, suitable sucrose esters include those having high monoester content, which have higher HLB values. However, sorbitan esters are not used alone as primary surfactants. In an embodiment if present sorbitan esters are used in combination with one or more primary surfactants and functions as a secondary or co-surfactant.

In one or more embodiments the surfactant is selected to produce a foam of quality being of least of about good quality foam and preferably of excellent quality foam. In one or more embodiments the surfactant includes, a fatty acid ester of glycerol, such as a mono, di or tri fatty ester of stearic acid or palmitic acid or arachidic acid or behenic acid. In one or more embodiments the surfactant is used on its own with the oil. In certain other embodiments the surfactant is used in combination with one or more other surfactants, such as, those listed below. In an embodiment the combination is, for example, glycerol monostearate, glycerol palmitostearate, and PEG 100 stearate. Other similar combinations are readily envisaged.

TABLE 2

| | | Glycerol fatty acid esters | | |
|---|---|---|---|---|
| Ester | Function | Solubility | Fatty acid (main) | Comments |
| glyceryl behenate | Thickener, lubricant | Practically insoluble in oil and water | Beheneic (C22) | Not tested |
| glyceryl monooleate | Non ionic Sufactant | Soluble in oil and practically insoluble in water | Oleic (double bond in side chain (C18) | Fairly Good Foam with mineral oil and silicone |

TABLE 2-continued

Glycerol fatty acid esters

| Ester | Function | Solubility | Fatty acid (main) | Comments |
|---|---|---|---|---|
| glyceryl monostearate (GMS) | Non ionic emulsifying agent | Soluble in mineral oil and practically insoluble in water | Stearic (C18) | Good-Excellent Foam with mineral oil and silicone oil even though GMS and other fatty acid monoesters are not efficient emulsifiers. |
| glyceryl palmitostearate | Sustained release, lubricant | Practically insoluble in mineral oil and water | Mixture of mono (~<17%), di, and triglycerides of C16 and C18 fatty acids | Excellent foam with mineral oil and silicone |

In an embodiment the surfactant is an ether for example polyoxyethylene (26) glycerol ether.

In certain embodiments, surfactants are selected which can provide a close packed surfactant layer. To achieve such objectives combinations of at least two surfactants are selected. Preferably, they should be complex emulgators and more preferably they should both be of a similar molecular type; for example, a pair of ethers, like steareth 2 and steareth 21, or a pair of esters, for example, PEG-40 stearate and polysorbate 80. Ideally, the surfactants can be ethers. In certain circumstances POE esters cannot be used and a combination of sorbitan laurate and sorbitan stearate or a combination of sucrose stearic acid ester mixtures and sodium laurate may be used. All these combinations due to their versatility and strength may also be used satisfactorily and effectively with ether formulations, although the amounts and proportion may be varied according to the formulation and its objectives as will be appreciated by a man of the art.

It has been discovered also that by using a derivatized hydrophilic polymer with hydrophobic alkyl moieties as a polymeric emulsifier such as pemulen it is possible to stabilize the emulsion better about or at the region of phase reversal tension. Other types of derivatized polymers like silicone copolymers, derivatized starch [Aluminum Starch Octenylsuccinate (ASOS)]/[DRY-FLO AF Starch], and derivatized dextrin may also a similar stabilizing effect.

A series of dextrin derivative surfactants prepared by the reaction of the propylene glycol polyglucosides with a hydrophobic oxirane-containing material of the glycidyl ether are highly biodegradable. [Hong-Rong Wang and Keng-Ming Chen, Colloids and Surfaces A: Physicochemical and Engineering Aspects Volume 281, Issues 1-3, 15 Jun. 2006, Pages 190-193].

Non-limiting examples of non-ionic surfactants that have HLB of about 7 to about 12 include steareth 2 (HLB~4.9); glycerol monostearate/PEG 100 stearate (Av HLB~11.2); stearate laureth 4 (HLB~9.7) and cetomacrogol ether (e.g., polyethylene glycol 1000 monoacetyl ether).

Non-limiting examples of surfactants, which have a HLB of 4-19 are set out in the Table below:

| Surfactant | HLB |
|---|---|
| steareth 2 | ~4.9 |
| glycerol monostearate/PEG 100 stearate | Av ~11.2 |
| glyceryl stearate | ~4 |
| steareth-21 | ~15.5 |

-continued

| Surfactant | HLB |
|---|---|
| peg 40 stearate | ~16.9 |
| polysorbate 80 | ~15 |
| sorbitan stearate | ~4.7 |
| laureth 4 | ~9.7 |
| sorbitan monooleate (span 80) | ~4.3 |
| ceteareth 20 | ~15.7 |
| steareth 20 | ~15.3 |
| ceteth 20 | ~15.7 |
| macrogol cetostearyl ether | ~15.7 |
| ceteth 2 (Lipocol C-2) | ~5.3 |
| PEG-30 dipolyhydroxystearate | ~5.5 |
| sucrose distearate (Sisterna SP30) | ~6 |
| polyoxyethylene (100) stearate | ~18.8 |

In some embodiments, the compositions described herein include Sepigel 305. Sepigel 305 comprises polyacrylamide and C13-14 isoparaffin and laureth-7. It acts as a surfactant and as a thickening and emulsifying agent, and comes in a liquid, very easy to handle form. It requires neither premixing, nor high rate of shear nor neutralisation. Sepigel 305 can be used to emulsify all types of oil phase without heating, producing gel-cream with a rich, silky texture that are easy to apply and rapidly absorbed by the skin.

More exemplary stabilizing surfactants which may be suitable for use in the present invention are found below.

PEG-Fatty Acid Monoester Surfactants, such as:

| Chemical name | Product example name | HLB |
|---|---|---|
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants, such as:

| Chemical name | Product example name | HLB |
|---|---|---|
| PEG-4 dilaurate | Mapeg ™ 200 DL (PPG), Kessco ™ PEG 200 DL (Stepan), LIPOPEG 2-DL (Lipo Chem.) | 7 |
| PEG-4 | distearate Kessco ™ 200 DS (Stepan. sub) | 5 |

-continued

| Chemical name | Product example name | HLB |
|---|---|---|
| PEG-32 dioleate | Kessco ™ PEG 1540 DO (Stepan) | 15 |
| PEG-400 dioleate | Cithrol 4DO series (Croda) | >10 |
| PEG-400 disterate | Cithrol 4DS series (Croda) | >10 |
| PEG-20 glyceryl oleate | Tagat ™ O (Goldschmidt) | >10 |

Transesterification Products of Oils and Alcohols, such as:

| Chemical name | Product example name | HLB |
|---|---|---|
| PEG-30 castor oil | Emalex C-30 (Nihon Emulsion) | 11 |
| PEG-40 hydrogenated castor oil | Cremophor RH 40 (BASF), Croduret (Croda), Emulgin HRE 40 (Henkel) | 13 |

Polyglycerized Fatty Acids, such as:

| Chemical name | Product example name | LB |
|---|---|---|
| Polyglyceryl-6 dioleate | Caprol ™ 6G20 (ABITEC); PGO-62 (Calgene), PLUROL OLEIQUE CC 497 (Gattefosse)Hodag | 8.5 |

PEG-Sorbitan Fatty Acid Esters, such as:

| Chemical name | Product example name | HLB |
|---|---|---|
| PEG-20 sorbitan monolaurate | Tween-20 (Atlas/ICI), Crillet 1 (Croda), DACOL MLS 20 (Condea) | 17 |
| PEG-20 sorbitan Monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan monooleate | Tween-80 (Atlas/ICI), Crillet 4 (Croda) | 15 |

Polyethylene Glycol Alkyl Ethers, such as:

| Chemical name | Product example name | HLB |
|---|---|---|
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | laureth-4Brij 30 (Atlas/ICI) | 9.7 |
| PEG-23 lauryl ether | laureth-23Brij 35 (Atlas/ICI) | 17 |
| PEG-10 stearyl ether | Brij 76 (ICI) | 12 |
| PEG-2 cetyl ether | Brij 52 (ICI) | 5.3 |

Sugar Ester Surfactants, such as:

| Chemical name | Product example name | HLB |
|---|---|---|
| Sucrose disterate | Sisterna SP50, Surfope 1811 | 11 |

Sorbitan Fatty Acid Ester Surfactants, such as Span 40, 60 and 80 have not been found suitable on their own with the high oil silicone foamable formulations:

| Chemical name | Product example name | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a complex emulgator in which the combination of two or more surface active agents can be more effective than a single surfactant and provides a more stable formulation or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

Specific non-limiting examples of surfactant systems are, combinations of polyoxyethylene alkyl ethers, such as steareth 2 and steareth 20; steareth 2 and steareth 21 (Brij 72/Brij 721); combinations of polyoxyethylene stearates such as PEG 40 stearate and PEG 100 stearate (Myrj 52/Myrj 59); combinations of sucrose esters, such as sucrose stearate and sucrose distearate (Surphope 1816/Surphope 1807); combinations of sorbitan esters, such as sorbitan monolaurate and sorbitan monooleate (Span 20/Span 80); sorbitan monolaurate and sorbitan monostearate (Span 20/Span 60; combinations of sucrose esters and sorbitan esters, such as sucrose distearate and sorbitan monostearate (Surphope 1811 and Span 60); combinations of liquid polysorbate detergents and PEG compounds, such as PEG-20 sorbitan monooleate and PEG-40 stearate (Tween 80/Myrj 52 ); methyl glucose sesquistearate; polymeric emulsifiers, such as acrylates/C10-30 alkyl acrylate crosspolymers (Permulen TRI or TR2); liquid crystal systems, such as sorbitan stearate and sucrose cocoate (Arlatone 2121), sodium stearyl phthalamate (Stepan Mild RM1), polyglyceryl-10 pentastearate and behenyl alcohol and sodium stearoyl lactylate (Nikomulese 41) and cetearyl alcohol and cetearyl glucoside (Montanov 68) and the like.

In certain embodiments the surfactant is preferably one or more of the following: a combination of steareth-2 and steareth-21 on their own or in combination with glycerol monostearate (GMS); in certain other embodiments the surfactant is a combination of polysorbate 80 and PEG-40 stearate. In certain other embodiments the surfactant is a combination of glycerol monostearate and PEG 100 stearate. In certain other embodiments the surfactant is a combination of two or more of stearate 21, PEG 40 stearate, and polysorbate 80. In certain other embodiments the surfactant is a combination of two or more of laureth 4, sorbitan monooleate (Span80) and polysorbate 80. In certain other embodiments the surfactant is a combination of two or more of GMS and a ceteareth. In certain other embodiments the surfactant is a combination of two or more of steareth 21, ceteareth 20, ceteth 2 and laureth 4 . In certain other embodiments the surfactant is a combination of ceteareth 20 and polysorbate 40 stearate. In certain other embodiments the surfactant is a combination of sorbitan monostearate (Span 60 )and GMS. In certain other embodiments the surfactant is a combination of two or all of PEG 40 stearate, sorbitan stearate and polysorbate 60.

In certain other embodiments the surfactant is one or more of sucrose stearic acid esters, sorbitan laureth, and sorbitan stearate.

Without being bound by any particular theory or mode of operation, it is believed that the use of non-ionic surfactants with significant hydrophobic and hydrophilic components, increase the emulsifier or foam stabilization characteristics of the composition. Similarly, without being bound by any particular theory or mode of operation, using combinations of surfactants with high and low HLB's to provide a relatively close packed surfactant layer may strengthen the formulation.

In one or more embodiments the stability of the composition can be improved when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is preferably between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is preferably between about 5 and about 18.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect In one or more embodiments the surfactant is a surfactant or surfactant combination is capable of or which tends to form liquid crystals. Surfactants which tend to form liquid crystals may improve the quality of foams. Non-limiting examples of surfactants with postulated tendency to form interfacial liquid crystals are: phospholipids, alkyl glucosides, sucrose esters, sorbitan esters.

In one or more embodiments the at least one surface active agent is liquid. Moreover for the purposes of formulating with liquid ethers a liquid surfactant is preferred In one or more embodiments the liquid surfactant is a polysorbate, preferably polysorbate 80 or 60.

In one or more embodiments the at least one surface active agent is solid, semi solid or waxy. In a further embodiment they are soluble in oil and in another embodiment have a HLB of less than about 12.

It should be noted that HLB values may not be so applicable to non-ionic surfactants, for example, with liquid crystals or with silicones. Also HLB values may be of lesser significance in a waterless or substantially water-free environment.

In one or more embodiments the surfactant can be, a surfactant system comprising of a surfactant and a co surfactant, a waxy emulsifier, a liquid crystal emulsifier, an emulsifier which is solid or semi solid at room temperature and pressure, or combinations of two or more agents in an appropriate proportion as will be appreciated a person skilled in the art. Where a solid or semi solid emulsifier combination is used it can also comprise a solid or semi solid emulsifier and a liquid emulsifier. In a preferred embodiment at least one surfactant is a liquid.

In one or more embodiments, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. Non-ionic surfactants alone can provide formulations and foams of good or excellent quality in the carriers and compositions.

Thus, in a preferred embodiment, the surface active agent, the composition contains a non-ionic surfactant. In another preferred embodiment the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1

In one or more embodiments, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1; for example, about 1:1, about 4:1, about 8:1, about 12:1, about 16:1 and about 20:1 or at a ratio of 4:1 to 10:1, for example, about 4:1, about 6:1, about 8:1 and about 10:1.

For foams in selecting a suitable surfactant or combination thereof it should be borne in mind that the upper amount of surfactant that may be used may be limited by the shakability of the composition. If the surfactant is non-liquid, it can make the formulation to viscous or solid. Subject to its miscibility solid surfactants may be added first, and may require gentle warming and then cooling before being combined with the other ingredients. In general terms, as the amount of non-liquid surfactant is increased the shakability of the formulation reduces until a limitation point is reached where the formulation can become non-shakable and unsuitable. Thus in one embodiment, any effective amount of surfactant may be used provided the formulation remains shakable. In other certain limited embodiments the upper limit for foamable formulations may be determined by flowability such that any effective amount can be used provided the formulation is sufficiently flowable to be able to flow through an actuator valve and be released and still expand to form a good quality foam. This may be due without being bound by any theory to one or more of a number of factors such as the viscosity, the softness, the lack of crystals, the pseudoplastic or semi pseudo plastic nature of the composition and the dissolution of the propellant into the composition.

In certain embodiments the amount of surfactant or combination of surfactants is between about 0.05% to about 20%; between about 0.05% to about 15%. or between about 0.05% to about 10%. In a preferred embodiment the concentration of surface active agent is between about 0.2% and about 8%. In a more preferred embodiments the concentration of surface active agent is between about 1% and about 6% or between about 1% and about 4%.

In some embodiments, it is desirable that the surface active agent does not contain a polyoxyethylene (POE) moiety, such as polysorbate surfactants, POE fatty acid esters, and POE alkyl ethers, because the active agent is incompatible with such surface active agents. For example, the active agent pimecrolimus is not stable the presence of POE moieties, yet benefits greatly from the use of dicarboxylic esters as penetration enhancers. In such cases, alternative surface active agents are employed. In an exemplary manner, POE-free surfactants include non-ethoxylated sorbitan esters, such as sorbitan monopalmitate, sorbitan monostearate, sorbitan tristearate, sorbitan monooleate, sorbitan trioleate, sorbitan monolaurate and sorbitan sesquioleate; glycerol fatty acid esters, such as glycerol monostearate and glycerol monooleate; mono-, di- and tri-esters of sucrose with fatty acids (sucrose esters), sucrose stearate, sucrose distearate sucrose palmitate and sucrose laurate; and alkyl polyglycosides, such as lauryl diglucoside.

In one or more embodiments, the surface-active agent includes mono-, di- and tri-esters of sucrose with fatty acids (sucrose esters), prepared from sucrose and esters of fatty acids or by extraction from sucro-glycerides. Suitable sucrose esters include those having high monoester content, which have higher HLB values.

In one or more preferred embodiments the surfactant includes at least one surfactant selected from a polyoxyethylene fatty ether, a polyoxyethylene fatty ester, a carbohydrate ester and a sucrose ester.

In one or more embodiments non-limiting examples of non-ionic surfactants include steareth-2, steareth-20, steareth-21, ceteareth 2, PEG-100 stearyl ether, cetearyl glucoside, methyl glucose sesquistearate, sorbitan monostearate, GMS and sorbitan laurate (Span 20).

In one or more embodiments non-limiting other examples of surfactant combinations are glycerol stearate and PEG 100 stearate and laureth 4; steareth 2, PEG 100 stearate and laureth 4; and cetearyl glucoside and cetearyl alcohol.

In an embodiment the surfactant containing formulations are further boosted by a foam adjuvant for example stearyl alcohol.

A non-limiting example of a combination of surfactants having a weighted average of their HLB values of 11 is glycerol stearate and PEG-100 stearate (for example trade name "Simulsol 165" from Sepic).

In some embodiments, the surface active agent is one or more of: glycerol monostearate, polysorbate 80, polysorbate 60, sucrose distearate, polyoxyl 20 stearyl ether, PEG-2 stearyl ether, PEG 100 stearate, PEG 40 stearate (Myrj 52), surcorse stearic acid esters, (Sufhope SE D-1805), cocoglucoside and coconut alcohol (Montanov S), or polyacrylamide and C13-14 isoparaffin and laureth -7 (Sepigel 305).

Solid Matter Agents

According to an embodiment, the at least one active agent comprises solid matter or particulate matter i.e., material that is not soluble in the liquid carrier composition of the foamable composition. For definition purposes, solid matter shall mean material that is not soluble in the foamable composition more than 10% of the concentration intended to be included in said foamable composition. The concentration of the solid matter in the foamable composition is from about 0% to about 20% w/w. In one or more embodiments, the concentration of solid matter in the composition is from about 2% to about 16% w/w.

By way of non-limiting examples, the following classes of solid matter substances are presented:

Metallic oxides, such as titanium dioxide, zinc oxide, zirconium oxide, iron oxide. Preferably, as used in the present invention, titanium dioxide has an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. In one embodiment the metal oxides are present in the amount of from about 0.1% to about 20%, preferably from about 0.5% to about 16%, more preferably from about 1% to about 10%, of the composition. In yet another embodiment, such solids are micronized to form particles having primary size of less than 15 nm.

Carbon, for example in the form of amorphous carbon or graphite;

Oxidizing agents, such as benzoyl peroxide, calcium and magnesium hypochlorite;

Metallic Silver, in small particles, including nanocrystalline silver, which is used for antibacterial and wound healing purposes; other metal particles and mineral particles;

Cosmetic scrub materials, including, for example meals of strawberry seeds, raspberry seeds, apricot seeds, sweet almond, cranberry seeds; and pigments, which are insoluble in the foamable composition.

Hydrophobic Solvent

Optionally, the foamable carrier further contains at least one other hydrophobic solvent. In some embodiments, the liquid oil is a hydrophobic solvent. The identification of a "hydrophobic solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

A "hydrophobic solvent" as used herein refers to a material having solubility in distilled water at ambient temperature of less than about 1 gm per 100 mL, more preferable less than about 0.5 gm per 100 mL, and most preferably less than about 0.1 gm per 100 mL.

In one or more embodiments, the hydrophobic organic carrier is an oil, such as mineral oil, MCT oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers.

One class of hydrophobic solvents includes polyunsaturated oils, containing omega-3 and omega-6 fatty acids, which are know to possess therapeutic properties through different modes of action. Examples of such polyunsaturated fatty acids are linoleic and linolenic acid, gamma-linoleic acid (GLA), eicosapentaenoic acid (EPA) and docosahexaenoic acid (DHA). Thus, in one preferred embodiment the at least one hydrophobic solvent comprises at least 6% of an oil selected from omega-3 oil, omega-6 oil, and mixtures thereof.

Another preferred class of hydrophobic solvents comprises the essential oils, which are considered "therapeutic oils", which contain active biologically occurring molecules and, upon topical application, exert a therapeutic effect. Examples of such oils are rosehip oil, which contain retinoids and is known to reduce acne and post-acne scars, tea tree oil, which possesses anti-microbial activity including antibacterial, antifungal and antiviral properties. Other examples of essential oils are basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla, verbena, as well as any other therapeutically beneficial oil known in the art of herbal medication.

Emollients

A further class of solvents present in some embodiments are "emollients" that have a softening, refatting, or soothing effect, especially when applied to body areas, such as the skin and mucosal surfaces. Emollients are not necessarily hydrophobic. Without derogating the generality of this definition, examples of suitable emollients for use include but are not limited to mineral oil, lanolin oil, coconut oil, cocoa butter, cocoglycerides, olive oil, aloe vera extract, jojoba oil, castor oil, fatty acids, fatty alcohols, diisopropyl adipate, hydroxybenzoate esters, benzoic acid esters of C9 to C15 alcohols, isononyl iso-nonanoate, isopropyl myristate, silicone oils, polyethers, C12 to C15 alkyl benzoates, oleic acid, stearic fatty acid, cetyl alcohols, hexadecyl alcohol, dimethyl polysiloxane, polyoxypropylene cetyl ether, polyoxypropylene butyl ether, hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, sucrose esters of fatty acids, octyl hydroxystearate and, and derivatives, esters, salts and mixtures thereof. Examples of other suitable emollients may be found in the Cosmetic Bench Reference, pp. 1.19-1.22 (1996) and in similar publications. In an embodiment, the oily solvent component is an emollient.

Foam Adjuvant

Optionally, a foam adjuvant is included in the foamable carriers to increase the foaming capacity of surfactants and/or to stabilize the foam. In one or more embodiments, the foam adjuvant agent includes fatty alcohols having 14 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

In a preferred embodiment the foam adjuvant is a solid, wax or powder at room temperature. In certain embodiments where two or more foam adjuvants are used at least one should be a solid, wax or powder at room temperature. In some embodiments, the foam adjuvant is a solid fatty alcohol. Examples of solid fatty alcohols include, without limitation, stearyl alcohol, cetyl alcohol, cetostearyl alcohol, myristyl alcohol, palmitoleyl alcohol, arachidyl alcohol and behenyl alcohol In some embodiments, the foam adjuvant is oleyl alcohol.

Substantially Alcohol Free

Lower or short chain alcohols, having up to 5 carbon atoms in their carbon chain skeleton, such as ethanol, propanol, isopropanol, butanol, iso-butanol, t-butanol and pentanol are considered less desirable solvents or co-solvents due to their skin-irritating effect. Thus, according to some embodiments, the composition is substantially alcohol-free i.e., free of short chain alcohols. In other embodiments, the composition comprises less than about 5% final concentration of lower alcohols, preferably less than 2%, more preferably less than 1%.

Potent Solvent

In one or more embodiments, the foamable composition includes a potent solvent, in addition to the hydrophobic solvents, polar solvents or emollients of the composition. A potent solvent is a solvent other than mineral oil that solubilizes a specific active agent substantially better than a hydrocarbon solvent such as mineral oil or petrolatum. For example, a potent solvent solubilizes the active agent 5 fold better than a hydrocarbon solvent; or even solubilizes the active agent 10-fold better than a hydrocarbon solvent.

A non-limiting exemplary list of solvents that can be considered as potent solvents includes polyethylene glycol, propylene glycol, hexylene glycol, butanediols and isomers thereof, glycerol, benzyl alcohol, DMSO, ethyl oleate, ethyl caprylate, diisopropyl adipate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol) and laurocapram.

The use of a potent solvent in a foam composition provides an improved method of delivering poorly soluble therapeutic agents to a target area. It is known that low drug solubility results in poor bioavailability, leading to decreased effectiveness of treatment. Foam compositions, for which the solvent includes a potent solvent, increase the levels of the active agent in solution and thus, provide high delivery and improved therapy.

In one or more embodiments, the PPG alkyl ether may act as a potent solvent.

Modulating Agent

In one or more embodiments the modulating agent is used in a unique waterless liquid oil with silicone.

The term modulating agent is used to describe an agent which can improve the stability of or stabilize a carrier or a foamable composition and/or an active agent by modulating the effect of a substance or residue present in the carrier or composition. The substance or residue may for example be acidic or basic and potentially alter an artificial pH in a waterless or substantially non-aqueous environment or it may be one or more metal ions which may act as a potential catalyst in a waterless or substantially non-aqueous environment or it may be an ionisation agent or it may be an oxidizing agent.

In the embodiment modulating agent is used to describe an agent which can effect pH in an aqueous solution. the term modulating agent more particularly means an acid or base or buffer system or combinations thereof, which is introduced into or is present in and acts to modulate the ionic or polar characteristics and any acidity or basesity balance of a waterless or substantially non-aqueous carrier, composition, foamable carrier or foamable composition or resultant foam.

In an embodiment, the modulating or additional component is a pH adjusting agent or a buffering agent.

The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the waterless solvent to enable it to "mop up" or "lock" metal ions.

In one or more embodiments the chelating agent is selected from the group consisting of acetyl trihexyl citrate, aminotrimethylene phosphonic acid, beta-alanine diacetic acid, bismuth citrate, calcium disodium edta, citric acid, cyclohexanediamine tetraacetic acid, diammonium citrate, dibutyl oxalate, diethyl oxalate, diisobutyl oxalate, diisopropyl oxalate, dilithium oxalate, dimethyl oxalate, dipotassium edta, dipotassium oxalate, dipropyl oxalate, disodium edta, disodium edta-copper, disodium pyrophosphate, edta, etidronic acid, hedta, methyl cyclodextrin, oxalic acid, pentapotassium, triphosphate, pentasodium aminotrimethylene phosphonate, pentasodium pentetate, pentasodium triphosphate, pentetic acid, phytic acid, potassium citrate, sodium citrate, sodium dihydroxyethylglycinate, sodium gluceptate, sodium gluconate, sodium hexametaphosphate, sodium metaphosphate, sodium metasilicate, sodium oxalate, sodium trimetaphosphate, tea-edta, tetrahydroxypropyl ethylenediamine, tetrapotassium etidronate, tetrapotassium pyrophosphate, tetrasodium edta, tetrasodium etidronate, tetrasodium pyrophosphate, tripotassium edta, trisodium edta, trisodium hedta, trisodium nta, trisodium phosphate, malic acid, fumaric acid, maltol, succimer, penicillamine, dimercaprol, and desferrioxamine melate.

Modulating agents may be added to the compositions of the subject invention, preferably from about 0.1% to about 10%, more preferably from about 1% to about 5%, of the composition. Where the active agent itself is the modulating agent alone or in combination with another modulating agent it will be added at an effective dose which may be outside these ranges. For example azaleic acid may be at about 15% of the composition.

Further detail regarding modulating agents is found in co-pending Published U.S. Patent Application 2008/0206159, which is hereby incorporated in its entirety by reference.

The substance or residue can be introduced into the formulation from any one or more of the ingredients, some of which themselves may have acidic or basic properties. For example the polymer or solvent may contain basic residues in which case it may be desirable or beneficial to add an acid. Alternatively the surfactant may contain some acid residues in which case the addition of a base may be desirable and beneficial. In some cases more than one ingredient may contain residues which may ameliorate or compound their significance. For example if one ingredient provided weak acid residues and another stronger acid residues the artificial pH in a waterless environment should be lower. In contrast, if one residue was acid and the other basic the net effect in the formulation maybe significantly reduced. In some circumstances the active ingredient may favor an acidic pH or more significantly may need to be maintained at a certain acidic pH otherwise it may readily isomerize, chemically react or breakdown, in which case introducing acidic components might be of help. Likewise in some circumstances the active ingredient may favor a basic pH or more significantly may need to be maintained at a certain basic pH otherwise it may readily hydrolyse, undergo rearrangement, isomerize, chemically react or breakdown, in which case introducing basic components might be of help. In an embodiment sufficient modulating agent is added to achieve an artificial pH in which the active agent is preferably stable. Such artificial pH may be acidic, maybe basic or may be neutral.

The modulating agent to the foamable composition is useful for stabilizing pharmaceutical and cosmetic active agents which are unstable in certain pH conditions. It is known, for example, that active agents, which contain ester bond in their structure tend to undergo hydrolysis of the ester bond at basic pH levels. Therefore, the addition of an agent which avoids the formation of basic pH condition and thus, prevents degradation of such active agents. Many steroid compounds are known to undergo rearrangement at high pH, and again, adding an acidic modulating agent helps prevent such degradation. Another example of a pH-sensitive active agent is vitamin D, which degrades at low pH levels. In such a case, the addition of a basic modulating agent, such as triethanol amine is useful to maintain acceptable stability of this active agents.

It is important to maintain skin surface pH in order to prevent susceptibility to bacterial skin infections or skin damage and disease. Thus, adding a modulating agent, which contributes to the stabilization of skin pH at the desirable level, is advantageous.

In the same fashion, adding an acidic modulating agent to a foamable composition, which is intended for vaginal application is advantageous, since the best protection against vaginal infection is attained in pH lower than 4.

Anti-Oxidants/Radical Scavengers

In one or more embodiments, the modulating agent may also be a preservative or an antioxidant or an ionization agent. Any preservative, antioxidant or ionization agents suitable for pharmaceutical or cosmetic application may be used. Non-limiting examples of antioxidants are tocopherol succinate, propyl galate, butylated hydroxy toluene and butyl hydroxy anisol. Ionization agents may be positive or may be negative depending on the environment and the active agent or composition that is to be protected. Ionization agents may for example act to protect or reduce sensitivity of active agents. Non-limiting examples of positive ionization agents are benzyl conium chloride, and cetyl pyridium chloride. Non-limiting examples of negative ionization agents are sodium lauryl sulphate, sodium lauryl lactylate and phospholipids.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Rolex), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

In one or more embodiments the modulating agent is a flavonoid.

A non-limiting list of flavonoid compounds is: benzquercin, diosmin, ethoxazorutoside, flavodate, sodium hesperidin, leucocianido, monoxerutin, oxerutin, quercetin, rutoside, rosmarinic acid. The above information was noted from Dietary Supplements, Electronic Version, Pharmaceutical Press 2007. In an embodiment the flavanoid includes quercitin and/or rutin. In certain embodiments the flavonoids act synergistically with each other or with other actives.

Microsponges

Microsponges are rigid, porous and spongelike round microscopic particles of cross-linked polymer beads (e.g., polystyrene or copolymers thereof), each defining a substantially noncollapsible pore network. Microsponges can be loaded with an active ingredient and can provide a controlled time release of the active ingredient to skin or to a mucosal membrane upon application of the formulation. The slow release is intended to reduce irritation by the active. Microsponge® delivery technology was developed by Advanced Polymer Systems. In one or more embodiments the composition comprises one or more active agents loaded into Microsponges with a waterless carrier described herein which may comprise a modulating agent.

Humectant

A humectant, is a substance that helps retain moisture and also prevents rapid evaporation. Non-limiting examples of suitable humectants are propylene glycol, propylene glycol derivatives, and glycerin. Further humectants include but are not limited to guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, lactamide monoethanolamine, acetamide monoethanolamine and derivatives, esters, salts and mixtures thereof.

Other examples of humectants and moisturizers may be found in the Handbook of Pharmaceutical Additives published by Gower. Suitable ones for use with and soluble in the waterless compositions may be selected as will be appreciated by a person skilled in the art.

Moisturizers

A moisturizer, is a substance that helps retain moisture or add back moisture to the skin. Examples are allantoin, petrolatum, urea, lactic acid, sodium PCV, glycerin, shea butter, caprylic/capric/stearic triglyceride, candelilla wax, propylene glycol, lanolin, hydrogenated oils, squalene, sodium hyaluronate and lysine PCA. Glycerine and sodium pCA work in combination. Other examples may be found in the *Handbook of Pharmaceutical Additives* published by Gower.

Pharmaceutical compositions may in one or more embodiments usefully comprise in addition a humectant or a moisturizer or combinations thereof.

Additional Components

In an embodiment, a composition includes one or more additional components. Such additional components include but are not limited to anti perspirants, anti-static agents, buffering agents, anti-oxidants/free radical scavengers, bulking agents, chelating agents, cleansers, colorants, conditioners, deodorants, diluents, dyes, emollients, fragrances, hair conditioners, humectants, pearlescent aids, perfuming agents, permeation enhancers, pH-adjusting agents, occlusive agents, preservatives, protectants, skin penetration enhancers, softeners, solubilizers, sunscreens, sun blocking agents, sunless tanning agents, viscosity modifiers and vitamins. As is known to one skilled in the art, in some instances a specific additional component may have more than one activity, function or effect.

In an embodiment, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

In an embodiment, the additional component is a humectant.

In an embodiment no preservative is added because the formulation is a waterless oil-based formulation having an Aw (Water Activity) value of less than 0.5 which is below the level of microbial proliferation. In certain limited embodiments, the additional component is an oil soluble preservative. Suitable preservatives include but are not limited to C12 to C15 alkyl benzoates, alkyl p-hydroxybenzoates, castor oil, cetyl alcohols, chlorocresol, cocoa butter, coconut oil, diisopropyl adipate, dimethyl polysiloxane, fatty acids, fatty alcohols, hexadecyl alcohol, jojoba oil, lanolin oil, mineral oil, oleic acid, olive oil, polyoxypropylene butyl ether, polyoxypropylene cetyl ether, silicone oils, stearic fatty acid, vitamin E, vitamin E acetate and derivatives, esters, salts and mixtures thereof.

In an embodiment, the additional component is a skin penetration enhancer.

Propellants

Examples of suitable propellants include volatile hydrocarbons such as butane, propane, isobutane and fluorocarbon gases, or mixtures thereof.

In an embodiment the propellant is 1681, which is a mixture of propane, isobutene and butane. In another embodiment it is AP 70, which is a mixture of propane, isobutene and butane with a higher pressure.

The propellant makes up about 3-25 wt % of the foamable composition. In some circumstances the propellant may be up to 35%. Thus, in some embodiments, the ratio of the liquefied or compressed gas propellant to the other components of the formulation ranges from about 3:100 to about 25:100 by weight, from about 3:100 to about 35:100, or from about 3:100 to about 45:100. In some embodiments, the ratio of the liquefied or compressed gas propellant to the other components of the formulation is at least about 3:100, at least about 10:100, at least about 15:100, at least about 20:100, or at least about 25:100. The propellants are used to generate and administer the foamable composition as a foam. The total composition including propellant, foamable compositions and optional ingredients is referred to as the foamable composition.

Alcohol and organic solvents render foams inflammable. It has been surprisingly discovered that fluorohydrocarbon propellants, other than chloro-fluoro carbons (CMCs), which are non-ozone-depleting propellants, are particularly useful in the production of a non-flammable foamable composition. A test according to European Standard prEN 14851, titled "Aerosol containers—Aerosol foam flammability test" revealed that compositions containing an organic carrier that contains a hydrophobic organic carrier and/or a solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect include propellants made by DuPont under the registered trademark Dymel, such as 1,1,1,2 tetrafluorethane (Dymel 134), and 1,1,1,2,3,3,3 heptafluoropropane (Dymel 227) 1,1, difluoro ethane (Dymel 152) and 1,1,1,3,3,3 hexafluoropropane HFCs possess Ozone Depletion Potential of 0.00 and thus, they are allowed for use as propellant in aerosol products.

Notably, the stability of foamable emulsions including HFC as the propellant can be improved in comparison with the same composition made with a hydrocarbon propellant.

In one or more embodiments foamable compositions comprise a combination of a HFC and a hydrocarbon propellant such as n-butane or mixtures of hydrocarbon propellants such as propane, isobutane and butane. Where mixtures are used they can be selected to generate different levels of pressure. For example 1681 has a lower pressure than AP 40 which is lower than that provided by propane alone. The amount and pressure of the propellant is selected to provide foam release without powerful jets and without tailing such that the foam is released in ideally a substantially single unbroken pulse.

In one or more embodiments "liquification" occurs following adding the propellant, which in turn will affect the viscosity substantially or radically. Thus in one or more embodiments the oil with silicone compositions are liquefied or further liquefied by the propellant.

Composition and Foam Physical Characteristics and Advantages

A pharmaceutical or cosmetic composition manufactured using the foamable carrier is very easy to use. When applied onto the body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition is stable, having an acceptable shelf-life of at least one year, or preferably, at least two years at ambient temperature, as revealed in accelerated stability tests. Organic carriers and propellants tend to impair the stability of emulsions and to interfere with the formation of stable foam upon release from a pressurized container. It has been observed, however, that the foamable compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Quantitative and Qualitative

Foam Quality

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

Foam Physical Characteristics

In terms of foam consistency and texture an acceptable foam is one, that exhibits the following characteristics:

Upon release from an aerosol can, creates a foam mass, which is sustained on a surface for at least one minute, more preferably at least two minutes, and yet more preferably for at least 3 minutes or more, say even about 5 minutes.

Foam texture should vary from a very fine creamy foam to a fine bubble structure.

In terms of spreadability and absorption an acceptable foam is one, that does not readily collapse upon dispensing on the skin; spreads easily on a skin surface; at least partially absorbed following rubbing onto the skin, and more preferably, substantially absorbed following rubbing on the skin.

In terms of tactile properties an acceptable foam is one, that: creates a pleasant feeling after application; leaves minimal oily residue; and leaves minimal shiny residual look.

Foam Collapse

A further aspect of the foam is breakability. Thermally sensitive foams immediately collapse upon exposure to skin temperature and, therefore, cannot be applied on the hand and afterwards delivered to the afflicted area.

The foam has several notable advantages, when compared with hydroalcoholic foam compositions, such as (1) Breakability. The foam is thermally stable and breakable under sheer force but is not "quick breaking which allows comfortable application and well directed administration to the target area;

(2) Skin drying and skin barrier function. Short chain alcohols are known to dry the skin and impair the integrity of the skin barrier. By contrast, having an liquid oil in the composition protects and improves moisturization and does not cause unwanted skin barrier damage.

(3) Irritability. Due to the lack of lower alcohols (C1-C5) and improvement in skin barrier function, the use of non-ionic surfactants, the presence of silicone and improvement in skin barrier function, skin irritability is eliminated.

(4) Dry feeling. The presence of silicone can significantly reduce alleviate or overcome the dry (no water) feeling of waterless formulations possibly due to its lubricating property and it may also ameliorate the oily feeling of the carrier. Moreover, the change in nature from an oily fluid to a relatively low density foam also can have a positive effect on skin or body cavity feeling.

Another property of the foam is specific gravity, as measured upon release from the aerosol can. Typically, oily foams have specific gravity of less than 0.20 g/mL; or less than 0.15 g/mL; or less than 0.12 g/mL, depending on their composition and on the propellant concentration. Preferably, specific gravity is in the range of about 0.05 gr/mL to about 0.20 gr/mL, more preferably between about 0.07 gr/mL and about 0.15 gr/mL.

Pharmaceutical Composition

The foamable composition is an ideal vehicle for active pharmaceutical ingredients and/or active cosmetic ingredients. In the context, active pharmaceutical ingredients and active cosmetic ingredients are collectively termed "active agent" or "active agents". The silicone and oil waterless formulations optionally coupled with the use of modulating agents can uniquely be adapted to protect and preserve active agents when stored in compatible sealed canisters with propellant A foamable composition, comprising an active agent has the following advantages:

1. The foamable composition provides a preferred solvent for active agents, particularly for poorly soluble or water-insoluble agents.
2. The provision of an essentially single phase foamable composition facilitates a co-solvent effect, resulting increased concentrations of soluble active agent in the dosage form, thus facilitating enhanced skin penetration of the active agent. In many cases, increased penetration is positively correlated with improved clinical outcome. In certain case, attaining an increased drug penetration into the target site of action enables a decrease of treatment frequency, for example, from twice or three times daily to once daily. Oils with a secondary solvent can act as skin penetration enhancers, thus, increasing drug residence time in the target area and increasing clinical efficacy, as detailed above.
3. The fact that the composition contains no or little water, minimizes the probability of degradation of water-sensitive active agents. Furthermore, as exemplified herein, a foam containing an oil and a silicone with no water at all can be formed in accordance with the composition and process. Such compositions ensure high stability of water sensitive active agents.
4. The foamable silicone and oil composition is contained in an impermeable pressurized packaging presentation is impermeable and thus, the active agent is not exposed to environmental degradation factors, such as light and oxidating agent during storage.

Thus, in one or more embodiments, the foamable composition includes at least one therapeutic agent, in a therapeutically effective concentration. Therapeutic agents are described herein. In addition, compounds disclosed in International Patent Publication No. WO 2004/03284, which is incorporated by reference in its entirety are suitable for use in the pharmaceutical compositions described herein.

In an embodiment the therapeutic agent is soluble in the foamable composition. In alternative embodiments the therapeutic agent is partially soluble and in further embodiments the therapeutic agent is insoluble in the formulation. Where the agent is insoluble or partially soluble it is provided as a homogenous suspension. In certain embodiments the homogeneous suspension remains homogenous over a substantial period of time suitable for pharmaceutical use. In other embodiments the agent may cram or separate out but homogeneity is fully reversible on shaking.

Oil soluble active agents may be readily used in the oil/silicone surfactant compositions described herein. A short list of non limiting examples of oil soluble active agents include calcipotriol, calcitriol, ciclopiroxolamine, benzocaine. Other examples are terbinofine, diclofenac, tacrolimus and pimecrolimus and also oil soluble vitamins. Estradiol, progesterone are non limiting examples of sparingly oil soluble agents.

Because the prefoam formulations can provide a substantially waterless, high oil content environment, particular classes of active pharmaceutical ingredients (APIs) will benefit from their inclusion in the composition. For example, active agents that are water sensitive, such as minocycline, doxycycline and other tetracycline drugs, vitamin D (e.g., calcipotriol and calcitriol), can have improved stability in the waterless composition. API's that are esters or amides are generally prone to hydrolysis by water and would benefit from a water free oil environment. API's that are sensitive to free radical attack or oxidation also would benefit from a water free oil environment. Similarly, active agents that are sensitive to specific pH level (which prevails in the presence of water) will also benefit. Exemplary APIs that would benefit from the silicone waterless compositions according to one or more embodiments include Vitamin D analogs and derivatives that degrade at low pH and corticosteroids that degrade at high pH. Oil soluble drugs can also be included in the compositions, such as corticosteroids, immunomodulators, such as tacrolimus and pimecrolimus, oil-soluble vitamins, e.g., vitamin A and derivatives thereof, other retinoids, vitamin E. Certain APIs may possess more than one of the above features, and thereby benefit even further from the silicone waterless compositions.

In one or more embodiments, the at least one therapeutic agent is selected from the group consisting of a steroidal antiinflammatory agent, a nonsteroidal anti-inflammatory drug, an immunosuppressive agent, an immunomodulator, an immunoregulating agent, a hormonal agent, an antibiotic agent, an antifungal agent, an antiviral agent, an antiparasitic agent, a vasoactive agent, a vasoconstrictor, a vasodilator, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, an antibiotic agent, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and mixtures thereof.

In certain cases, the disorder to be treated involves unaesthetic lesions that need to be masked. For example, rosacea involves papules and pustules, which can be treated with an antibiotic agent, as well as erythema, telangiectasia and redness, which partially respond to treatment with an antibiotic agent. Thus, in one or more embodiments, the additional active agent is a masking agent, i.e., a pigment. Non-limiting examples of suitable pigments include brown, yellow or red iron oxide or hydroxides, chromium oxides or hydroxides, titanium oxides or hydroxides, zinc oxide, FD&C Blue No. 1 aluminum lake, FD&C Blue No. 2 aluminum lake and FD&C Yellow No. 6 aluminum lake.

Suitable active agents include but are not limited to active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins, vitamin D derivatives, wound healing agents and wart removers. As is known to one skilled in the art, in some instances a specific active agent may have more than one activity, function or effect.

In an embodiment, the active agent is an active herbal extract. Suitable active herbal extracts include but are not limited to angelica, anise oil, *astragali radix*, azalea, benzyl acetate, birch tar oil, bornyl acetate, *cacumen biotae*, camphor, cantharidin, capsicum, cineole, cinnamon bark, cinnamon leaf, citronella, citroneliol, citronellyl acetate, citronellyl formate, eucalyptus, eugenyl acetate, flos carthami, *fructus mori*, garlic, geraniol, geranium, geranyl acetate, habanera, isobutyl angelicate, lavender, *ledum latifolium, ledum palustre*, lemongrass, limonene, linalool, linalyl acetate, methyl anthranilate, methyl cinnamate, mezereum, neem, nerol, neryl acetate, nettle root extract, oleum ricini, oregano, pinenes, .alpha.-pinene, .beta.-pinene, *radix angelicae sinesis, radix paenoiae rubra, radix polygoni multiflori, radix rehmanniae, rhizoma pinelliae, rhizoma zingiberis recens*, sabadilla, sage, sandalwood oil, saw palmetto extract, semen *sesami nigrum*, staphysagria, tea tree oil, terpene alcohols, terpene hydrocarbons, terpene esters, terpinene, terpineol, terpinyl acetate and derivatives, esters, salts and mixtures thereof. In an embodiment, the active agent is an acaricide. Suitable acaricides include but are not limited to amitraz, flumethrin, fluvalinate and derivatives, esters, salts and mixtures thereof.

In an embodiment, the active agent is an age spot and keratoses removing agent. Suitable age spot and keratoses removing agent include but are not limited to hydroxy acids, azelaic acid and other related dicarboxylic acids, retinoids, kojic acid, arbutin, nicotinic, ascorbic acid, hydroquinone and derivatives, esters, salts and mixtures thereof. Certain nonsteroidal anti-inflammatory agents, such as diclofenac are also useful for the treatment of keratoses.

In an embodiment, the active agent is an analgesic. Suitable analgesics include but are not limited to benzocaine, butamben picrate, dibucaine, dimethisoquin, dyclonine, lidocaine, pramoxine, tetracaine, salicylates and derivatives, esters, salts and mixtures thereof.

In an embodiment, the active agent is a local anesthetic. Suitable local anesthetics include but are not limited to benzocaine, benzyl alcohol, bupivacaine, butamben picrate, chloroprocaine, cocaine, dibucaine, dimethisoquin, dyclonine, etidocaine, hexylcaine, ketamine, lidocaine, mepivacaine, phenol, pramoxine, procaine, tetracaine, salicylates and derivatives, esters, salts and mixtures thereof.

In an embodiment, the active agent is an antiacne agent. Suitable antiacne agents include but are not limited to N-acetylcysteine, adapalene, azelaic acid, benzoyl peroxide, cholate, clindamycin, deoxycholate, erythromycin, flavinoids, glycolic acid, meclocycline, metronidazol, mupirocin, octopirox, phenoxy ethanol, phenoxy propanol, pyruvic acid, resorcinol, retinoic acid, salicylic acid, scymnol sulfate, sulfacetamide-sulfur, sulfur, tazarotene, tetracycline, tretinoin triclosan and derivatives, esters, salts and mixtures thereof.

In an embodiment, the active agent is an antiaging agent. Suitable antiaging agents include but are not limited to sulfur-containing D and L amino acids, alpha-hydroxy acids, beta-hydroxy acids (e.g. salicylic acid), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate) skin barrier forming agents, melatonin and derivatives, esters, salts and mixtures thereof.

In an embodiment, the active agent is an antidandruff agent. Suitable antidandruff agents include but are not limited to aminexil, benzalkonium chloride, benzethonium chloride, 3-bromo-1-chloro-5,5-dimethyl-hydantoin, chloramine B, chloramine T, chlorhexidine, N-chlorosuccinimide, climbazole-, 1,3-dibromo-5,5-dimethylhydantoin, 1,3-dichloro-5, 5-dimethyl-hydantoin, betulinic acid, betulonic acid, celastrol, crataegolic acid, cromakalin, cyproterone acetate, dutasteride, finesteride, ibuprofen, ketoconazole, oleanolic acid, phenyloin, picrotone olamine, salicylic acid, selenium sulphides, triclosan, triiodothyronine, ursolic acid, zinc gluconate, zinc omadine, zinc pyrithione and derivatives, esters, salts and mixtures thereof.

In an embodiment, the active agent is an antihistamine. Suitable antihistamines include but are not limited to chlorcyclizine, diphenhydramine, mepyramine, methapyrilene, tripelennamine and derivatives, esters, salts and mixtures thereof.

In the context, an antibiotic agent is a substance, that has the capacity to inhibit the growth of or to destroy bacteria and other microorganisms. In one or more embodiments, the antibiotic agent is selected from the classes consisting beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals including antibiotic metal ions, oxidizing agents, a periodate, a hypochlorite, a permanganate, substances that release free radicals and/or active oxygen, cationic antimicrobial agents, quaternary ammonium compounds, biguanides, triguanides, bisbiguanides and analogs and polymers thereof, naturally occurring antibiotic compounds, including antibiotic plant oils and antibiotic plant extracts, non-classified antibiotic compounds and antibiotic analogs, derivatives, salts, ions, complexes and mixtures thereof.

In an embodiment, the active agent is an antimycotic Also termed antifungal agent. The terms "antimycotic" and "antifungal" as used herein include, but is not limited to, any substance being destructive to or inhibiting the growth of fungi and yeast or any substance having the capacity to inhibit the growth of or to destroy fungi and/or yeast.

In one or more embodiments, the antifungal agent is an agent that is useful in the treatment of a superficial fungal infection of the skin, dermatophytosis, microsporum, *trichophyton* and *epidermophyton* infections, candidiasis, oral candidiasis (thrush), candidiasis of the skin and genital mucous membrane, candida paronychia, which inflicts the nail and nail bed and genital and vaginal candida, which inflict genitalia and the vagina.

Suitable antimycotics include but are not limited to allylamines, amorolfine, amphotericin B, azole compounds, bifonazole, butoconazole, chloroxine, clotrimazole, ciclopirox olamine, clotrimazole, econazole, elubiol, fenticonazole, fluconazole, flucytosine (5FC), griseofulvin, itraconazole, ketoconazole, mafenide acetate, miconazole, naftifine, natamycin, tolnaftate, nystatin, polyenes, oxiconazole, sulbentine, sulconazole, terbinafine, terconazole, tioconazole, undecylenic acid and derivatives, esters, salts and mixtures thereof.

In an embodiment, the active agent is an antipruritic. Suitable antipruritics include but are not limited to menthol, methdilazine, trimeprazine, urea and derivatives, esters, salts and mixtures thereof.

In an embodiment, the active agent is an additional antipsoriatic agent. Suitable additional antipsoriatic agents include but are not limited to 6-aminonicotinamide, 6-aminonicotinic acid, 2-aminopyrazinamide, anthralin, 6-carbamoylnicotinamide, 6-chloronicotinamide, 2-carbamoylpyrazinamide, corticosteroids, 6-dimethylaminonicotinamide, dithranol, 6-formylaminonicotinamide, 6-hydroxy nicotinic acid, 6-substituted nicotinamides, 6-substituted nicotinic acid, 2-substituted pyrazinamide, tazarotene, thionicotinamide, trichothecene mycotoxins and derivatives, esters, salts and mixtures thereof.

In an embodiment, the active agent is an antirosacea agent. Suitable antirosacea agents include but are not limited to azelaic acid, metronidazole, sulfacetamide and derivatives, esters, salts and mixtures thereof. Certain nonsteroidal anti-inflammatory agents, such as salicylic acid, salicylates, piroxicam and diclofenac are also useful for the treatment of Rosacea.

In an embodiment, the active agent is an antiseborrheic agent. Suitable antiseborrheic agents include but are not limited to glycolic acid, salicylic acid, selenium sulfide, zinc pyrithione, a dicarboxylic acid, such as azelaic acid and derivatives, esters, salts and mixtures thereof.

In an embodiment, the active agent is an antiviral agent. Suitable antiviral agents include but are not limited to acyclovir, gancyclovir, ribavirin, amantadine, rimantadine nucleoside-analog reverse transcriptase inhibitors, such as zidovudine, didanosine, zalcitabine, tavudine, lamivudine and vidarabine, non-nucleoside reverse transcriptase inhibitors, such as nevirapine and delavirdine, protease inhibitors, such as saquinavir, ritonavir, indinavir and nelfinavir, and interferons and derivatives, esters, salts and mixtures thereof.

In an embodiment, the active agent is a chemotherapeutic agent. Suitable chemotherapeutic agents include but are not limited to daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, XR9576 and derivatives, esters, salts and mixtures thereof.

In an embodiment, the active agent is a corticosteroid. Suitable corticosteroids include but are not limited to alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, difluorosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, .alpha.-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters, salts and mixtures thereof.

In an embodiment, the active agent is a hair growth regulator. Suitable hair growth regulators include but are not limited to N-acetylgalactosamine, N-acetylglucosamine, N-acetylmannosamine, acitretin, aminexil, ascomycin, asiatic acid, azelaic acid, benzalkonium chloride, benzethonium chloride, benzydamine, benzyl nicotinate, benzoyl peroxide, benzyl peroxide, betulinic acid, betulonic acid, calcium pantothenate, celastrol, cepharanthine, chlorpheniramine maleate, clindamycin hydrochloride, crataegolic acid, cromakalin, cyproterone acetate, diazoxide, diphenhydramine hydrochloride, dutasteride, estradiol, ethyl-2-hydroxypropanoate, finasteride, D-fucono-1,5-lactone, furoate, L-galactono-1,4-lactone, D-galactosamine, D-glucaro-1,4-lactone, D-glucosamine-3-sulphate, hinokitiol, hydrocortisone, 2-hydroxypropionic acid, isotretinoin, itraconazole, ketoconazole, latanoprost, 2-methyl propan-2-ol, minocyclin, minoxidil, mipirocin, mometasone, oleanolic acid, panthenol, 1,10-phenanthroline, phenyloin, prednisolone, progesterone, propan-2-ol, pseudoterins, resorcinol, selenium sulfide, tazarotene, triclocarbon, triclosan, triiodothyronine, ursolic acid, zinc pyrithione and derivatives, esters, salts and mixtures thereof.

In an embodiment, the active agent is a hormone. Suitable hormones include but are not limited to methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5a-dihydrotestosterone, testolactone, 17a-methyl-19-nortestosterone, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5a-pregnan-3b,20a-diol sulfate, 5a-pregnan-3b,20b-diol sulfate, 5a-pregnan-3b-ol-20-one, 16,5a-pregnen-3b-ol-20-one, 4-pregnen-20b-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone, progestins and derivatives, esters, salts and mixtures thereof.

In an embodiment, the active agent is a hydroxy acid. Suitable hydroxy acids include but are not limited to agaricic acid, aleuritic acid, allaric acid, altraric acid, arabiraric acid, ascorbic acid, atrolactic acid, benzilic acid, citramalic acid, citric acid, dihydroxytartaric acid, erythraric acid, galactaric acid, galacturonic acid, glucaric acid, glucuronic acid, glyceric acid, glycolic acid, gularic acid, gulonic acid, hydroxypyruvic acid, idaric acid, isocitric acid, lactic acid, lyxaric acid, malic acid, mandelic acid, mannaric acid, methyllactic acid, mucic acid, phenylacetic acid, pyruvic acid, quinic acid, ribaric acid, ribonic acid, saccharic acid, talaric acid, tartaric acid, tartronic acid, threaric acid, tropic acid, uronic acids, xylaric acid and derivatives, esters, salts and mixtures thereof.

In an embodiment, the active agent is a keratolytic agent. The term "keratolytic agent" is used herein to mean a compound which loosens and removes the stratum corneum of the skin, or alters the structure of the keratin layers of skin. Keratolytic agents are used in the treatment of many dermatological disorders, which involve dry skin, hyperkeratinization (such as psoriasis), skin itching (such as xerosis), acne and rosacea. Suitable keratolytic agents include but are not limited to N-acetylcysteine, azelaic acid, cresols, dihydroxy benzene compounds, such as resorcinol and hydroquinone, alpha-hydroxy acids, such as lactic acid and glycolic acid, phenol, pyruvic acid, resorcinol, sulfur, salicylic acid, retinoic acid, isoretinoic acid, retinol, retinal, urea and derivatives, esters, salts and mixtures thereof.

In an embodiment, the active agent is a lactam. Suitable lactams include but are not limited to L-galactono-1,4-lactam, L-arabino-1,5-lactam, D-fucono-1,5-lactam, D-glucaro-1,4-lactam, D-glucurono-6,3-lactam, 2,5-tri-O-acetyl-D-glucurono-6,3-lactam, 2-acetamido-2-deoxyglucono-1,5-lactam, 2-acetamido-2-deoxygalactono-1,5-lactam, D-glucaro-1,4:6,3-dilactam-, L-idaro-1,5-lactam, 2,3,5,tri-O-acetyl-D-glucaro-1,4-lactam, 2,5-di-O-acetyl-D-glucaro-1,4:6,3-dilactam, D-glucaro-1,5-lactam methyl ester, 2-propionoamide-2-deoxyglucaro-1,5-lactam and derivatives, esters, salts and mixtures thereof.

In an embodiment, the active agent is a non-steroidal anti-inflammatory agent. Suitable non-steroidal anti-inflammatory agent include but are not limited to azelaic acid, oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof.

In an embodiment, the active agent is insecticide. The term "insecticide, is used herein to mean a compound which kills, inhibits the growth of, impeded the proliferation of or repels insects. Insecticides include, for example, agents that can kill lice, flees, ticks, mites, scabies and mosquitoes, as well as agents that repel such insects. Suitable insecticides include but are not limited to DDT, lindane, malathion, permethrin, allethrin, biopermethrin, transpermethrin, phenothrin, diethyl-m-toluamide, dimethyl phthalate, piperonyl butoxide, pyrethroids and derivatives, esters, salts and mixtures thereof.

In an embodiment, the active agent is a vasodilator. Suitable vasodilators include but are not limited to agents that modulate the activity of the enzyme nitric oxide synthase, nicotinic acid, ethyl nicotinate, amyl nitrite, amyl nitrate, ethyl nitrite, butyl nitrite, isobutyl nitrite, glyceryl trinitrate, octyl nitrite, sodium nitrite, sodium nitroprusside, clonitrate, erythrityl tetranitrate, isosorbide mononitrate, isosorbide dinitrate, mannitol hexanitrate, pentaerythritol tetranitrate, penetrinitol, triethanolamine trinitrate, troInitrate phosphate (triethanolamine trinitrate diphosphate), propatylnitrate, nitrite esters of sugars, nitrite esters of polyols, nitrate esters of sugars, nitrate esters of polyols, nicorandil, apresoline, diazoxide, hydralazine, hydrochlorothiazide, minoxidil, pentaerythritol, tolazoline, scoparone, a beta-adrenergic blocker, an alpha-adrenoreceptor blocker, a prostaglandin, sildenafil, dipyridamole, catecholamine, isoproternol, furosemide, prostaglandin, prostacyclin, enalaprilat, morphine, acepromazine, prazosin (α-blocker), enalapril, Captopril, amlodipine, minoxidil, tadalafil, vardenafil, phenylephrin, etilefein, caffeine, capsaicin, an extract *capsicum, achillea millefolium* (Yarrow), *allium sativum* (garlic), *amoracia rusticana* (horseradish), *berberis vulgaris* (barberry), *cimicifuga racemosa* (black cohosh), *coleus forskholii* (coleus), *coptis* (goldenthread), *crataegus* (hawthorn), *eleutherococcus senticosus* (siberian ginseng), *ginkgo biloba* (ginkgo), *melissa officinalis* (lemon balm), *olea europaea* (olive leaf), *panax ginseng* (Chinese ginseng), *petroselinum crispum* (parsley), *scutellaria baicalensis* (baical skullcap), *tilia europaea* (linden flower), *trigonella foenum-graecum* (fenugreek), *urtica dioica* (nettles), *valeriana officinalis* (valerian), *viburnum* (cramp, bark, black haw), *veratrum viride* (American hellebore), *verbena officinalis* (vervain), *xanthoxylum americanum* (prickly ash), *zingiber officinale* (ginger), rauwolfia serpentina (Indian snakeroot), *viscum album*, wild yam, sasparilla, licorice, damiana, yucca, saw palmetto, gotu kola (*centella asiatica*), yohimbine and salts, hazelnut, brazil nut and walnut, and derivatives, esters, salts and mixtures thereof.

In an embodiment, the active agent is a vasoconstrictor. Suitable vasodilators include but are not limited to ephedrine, epinephrine, phenylephrine, angiotensin, vasopressin; an extract *ephedra sinica* (ma huang), *polygonum bistorta* (bistort root), *hamamelis virginiana* (witch hazel), *hydrastis canadensis* (goldenseal), *lycopus virginicus* (bugleweed), *aspidosperma quebracho* (quebracho blanco), *cytisus scoparius* (scotch broom) and cypress and derivatives, esters, salts and mixtures thereof.

In an embodiment, the active agent is a retinoid. Suitable retinoids include but are not limited to retinol, retinal, retinoic acid, all-trans retinoic acid, isotretinoin, tazarotene, adapalene, 13-cis-retinoic acid, acitretin all-trans beta carotene, alpha carotene, lycopene, 9-cis-beta-carotene, lutein and zeaxanthin.

In an embodiment, the active agent is a vitamin D analog. Suitable retinoids include but are not limited to calcipotriene, cholecalciferol, 25-hydroxycholecalciferol, 1α,25-dihydroxycholecalciferol, ergocalciferol, 1α,25-dihydroxyergocalciferol, 22,23-dihydroergocalciferol, 1,24,25-trihydroxycholecalciferol, previtamin $D_3$, tachysterol$_3$ (also termed tacalciol), isovitamin $D_3$, dihydrotachysterol$_3$, (1S)-hydroxycalciol, (24R)-hydroxycalcidiol, 25-fluorocalciol, ercalcidiol, ertacalciol, (5E)-isocalciol, 22,23-dihydroercalciol, (24S)-methylcalciol, (5E)-(10S)-10,19-dihydroercalciol, (24S)-ethylcalciol and (22E)-(24R)-ethyl-22,23-didehydrocalciol. In a preferred embodiment, the vitamin D analog is calcipotriene, which is useful in the treatment of psoriasis.

In an embodiment, the active agent is selected from the group consisting of an immunosuppressants and immunoregulating agents. Suitable immunosuppressants and immunoregulating agents include but are not limited to cyclic peptides, such as cyclosporine, tacrolimus, tresperimus, pimecrolimus, sirolimus (rapamycin), verolimus, laflunimus, laquinimod, imiquimod derivatives, esters, salts and mixtures thereof. In one or more embodiments, the immunomodulator is a calcineurin Inhibitor.

In an embodiment, the active agent is a wart remover. Suitable wart removers include but are not limited to imiquimod, podophyllotoxin and derivatives, esters, salts and mixtures thereof.

In an embodiment, the active agent is a photodynamic therapy (PDT) agent. Suitable PDT agents include but are not limited to modified porphyrins, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives, as well as photosensitiser precursors, such as aminolevulinic acid and derivatives, esters, salts and mixtures thereof.

In an embodiment, the active agent is an antioxidant or a radical scavenger. Suitable antioxidants and radical scavengers agents include but are not limited to ascorbic acid, ascorbyl esters of fatty acids, magnesium ascorbyl phosphate, sodium ascorbyl phosphate, ascorbyl sorbate, tocopherol, tocopheryl sorbate, tocopheryl acetate, butylated hydroxy benzoic acid, 6-hydroxy-2,5,7,8-tetramethylchroman-2-carboxylic acid, gallic acid, propyl gallate, uric acid, sorbic acid, lipoic acid, diethylhydroxylamine, amino-guanidine, glutathione, dihydroxy fumaric acid, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and polyunsaturated oils, containing omega-3 and omega-6 fatty acids (e.g., linoleic and linolenic acid, gamma-linoleic acid, eicosapentaenoic acid and docosahexaenoic acid and derivatives, esters, salts and mixtures thereof.

In an embodiment, the active agent is a self-tanning agent, such as dihydroxyacetone.

In an embodiment, the active agent is an agent, capable of treating hyperhydrosis. Suitable hyperhydrosis agents include but are not limited to anticholinergic drugs, boric acid, tannic acid, resorcinol, potassium permanganate, formaldehyde, glutaraldehyde, methenamine, a Lewis acid, aluminum chloride, aluminum chlorohydrates, zirconium chlorohydrates, aluminum-zirconium-Glycine (AZG) complex, aluminum hydroxybromide, a glycopyrrolate compound, a 5-alpha-reductase inhibitor, finasteride, epristeride, flutamide, spironolactone, saw palmetto extract, cholestan-3-one, a mono- and dicarboxylic acid having 4 to 18 carbon atoms, botulinum toxin, a 5-HT2C receptor antagonist, a 5-HT2C receptor antagonist, ketanserin, ritanserin, mianserin, mesulergine, cyproheptadine, fluoxetine, mirtazapine, olanzapine and ziprasidone.

In an embodiment, the active agent is a sunscreen agent. Suitable sunscreen agents include but are not limited to titanium dioxide, zinc oxide, zirconium oxide, iron oxide, p-aminobenzoic acid and its derivatives (ethyl, isobutyl, glyceryl esters; p-dimethylaminobenzoic acid); anthranilic acid derivatives (i.e., o-amino-benzoates, methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid, o- and p-hydroxybiphenyldisulfonates, coumarin derivatives (7-hydroxy, 7-methyl, 3-phenyl), diazoles (2-acetyl-3-bromoindazole, phenyl benzoxazole, methyl naphthoxazole, quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane.

In an embodiment, the active agent is a figure-forming agent and an agent, capable of treating cellulite. Suitable such agents include but are not limited to baldderwack extract, butcher's, broom, cayenne, dandelion, red clover, *ginkgo biloba*, horse chestnut, witch hazel and borage oil, caffeic acid, nicotinic acid, theophiline and pentoxyphilline and salts and derivatives thereof.

Several disorders of the skin, body cavity or mucosal surface (e.g., the mucosa or the cavity of the nose, mouth, eye, ear, vagina or rectum) involve a combination of etiological factors. For example, fungal and bacterial infections and that are inflamed and have symptoms of redness and/or itching warrant therapy that combines an anti-infective agent and an anti-inflammatory agent. Thus, in several cases, combining at least two active agents that treat different etiological factors results in a synergistic effect and consequently higher success rate of the treatment.

In certain cases, the composition contains two active agents, where each of the active agents require a different pH environment in order to remain stable. For example, corticosteroids are typically stable at acidic pH values (they have a maximum stability at a pH of about 4-6) and of vitamin D analogues are typically stable at basic pH values (they have a maximum stability at pH values above about 8). In order to circumvent the problem of instability it is preferred that the composition is substantially water-free. The term "substantially water-free" is intended to indicate that the composition has a water content below about 5%, preferably below about 2%, such as below about 1.5%.

Fields of Applications

The foamable carrier is suitable for treating any infected surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site").

By selecting a suitable active agent, or a combination of at least two active agents, the foamable composition is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition is suitable for treating a disorder of a body cavity or mucosal surface, e.g., the mucosa of the nose, mouth, eye, ear, respiratory system, vagina or rectum. Non-limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment, the composition is useful for the treatment of wound, ulcer and burn. This use is particularly important since the composition creates a thin, semi-occlusive layer, which coats the damaged tissue, while allowing exudates to be released from the tissue.

The composition is also suitable for administering a hormone to the skin or to a mucosal membrane or to a body cavity, in order to deliver the hormone into the tissue of the target organ, in any disorder that responds to treatment with a hormone.

In some embodiments, the target site for administration or delivery of the compositions described herein includes, without limitation, the skin, a body cavity, a mucosal surface, the nose, the mouth, the eye, the ear canal, the respiratory system, the vagina and the rectum.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

The compositions may be used as a substitute for ointment-based formulations when petrolatum is not desirable because it causes disturbance: too greasy, too occlusive, does not allow exudates to be released (like in wound & burn). It can also be used for treatment of disorders wherein the cosmetic elegance is an issue, like acne, rosacea (where the active agent requires water free environment, as specified above).

Shakability

'Shakability' means that the composition contains some or sufficient flow to allow the composition to be mixed or remixed on shaking. That is, it has fluid or semi fluid properties. In some very limited cases it may still be possible to have a foamable composition which is flowable but not apparently shakable.

Breakability

A breakable foam is thermally stable or substantially so, yet breaks under sheer force. The breakable foam is not "quick breaking", i.e., it does not readily collapse upon exposure to body temperature environment. Sheer-force breakability of the foam is clearly advantageous over thermally induced breakability, (due to, for example, the presence of alcohol) since it allows comfortable application and well directed administration to the target area.

Chemical Instability and Stability

By chemical instability of one or more active agents is meant that at least one of the one or more active agents is susceptible to one or more of inter alia reaction, breakdown, ionization or oxidation or the rate thereof is increased when incorporated into a pharmaceutical or cosmetic carrier that is non-aqueous or substantially non-aqueous.

Conversely by chemical stability of one or more active agents is meant that at least one of the one or more active agents is less susceptible to one or more of inter alia reaction, breakdown, ionization or oxidation or the rate thereof is impeded when incorporated into a pharmaceutical or cosmetic carrier that is non-aqueous or substantially non-aqueous.

Other foamable compositions are described in: U.S. Publication No. 05-0232869, published on Oct. 20, 2005, entitled NONSTEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No. 06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. Publication No. 2007-0292355 published on Dec. 20, 2007 and entitled ANTI-INFECTION AUGMENTATION OF FOAMABLE COMPOSITIONS AND KIT AND USES THEREOF; U.S. Publication No. 2008-0069779 and entitled DICARBOXYLIC ACID FOAMABLE VEHICLE AND PHARMACEUTICAL COMPOSITIONS THEREOF; U.S. Publication 20080206159, published on Aug. 28, 2008 and entitled COMPOSITIONS WITH MODULATING AGENTS; U.S. patent application Ser. No. 11/767,442, filed on Jun. 22, 2007, entitled FOAMABLE COMPOSITIONS AND KITS COMPRISING ONE OR MORE OF A CHANNEL AGENT, A CHOLINERGIC AGENT, A NITRIC OXIDE DONOR, AND RELATED AGENTS AND THEIR USES; U.S. Publication 2008-0069779, published on Mar. 20, 2008 and entitled FOAMABLE VEHICLE AND VITAMIN AND FLAVONOID PHARMACEUTICAL COMPOSITIONS THEREOF, all of which are incorporated herein by reference in their entirety. More particularly any of the active ingredients; the solvents; the surfactants; foam adjuvants; polymeric agents, penetration enhancers; preservatives, humectants; moisturizers; and other excipients as well as the propellants listed therein can be applied herein and are incorporated by reference.

The invention is described with reference to the following examples. This invention is not limited to these examples and experiments. Many variations will suggest themselves and are within the full intended scope of the appended claims.

Methodology

The formulations may be made in the following general way with appropriate adjustments for each formulation as will be appreciated by someone skilled in the art. Polymers, if any, are mixed, swelled and solubilized in the waterless medium, when necessary, with appropriate heat until it forms a clear solution. Stabilizing surfactants added usually with heat, until a homogeneous mixture is obtained, the mixture is then allowed to cool. The remainder of the ingredients, are then added with mixing until they have dissolved in the medium. The active agent is usually added at the end once the modulating agent, if present, has been incorporated. For foam the canisters are then filled with the above waterless formula, sealed and crimped with a valve and pressurized with the propellant.

A general procedure for preparing foamable compositions is set out in WO 2004/037225, which is incorporated herein in its entirety by reference.

Oily Waterless Foam 1. a) Heat oil to about 65° C. to about 70° C. mixing with a homogenizer; b) add surfactant(s) under mixing with a homogenizer until any solids are completely liquefied; c) where applicable, make a premix of heat sensitive ingredients with about a quarter part of silicone at room temperature and set aside; d) Mix b. well and cool rapidly to about below about 35° C. by plunging the container into an ice bath while stirring; e) Add the remaining silicone under mixing to the product of d. to obtain a homogenous mixture. f) Add polymers, if any, and add c) the premix of sensitive ingredients with moderate mixing at about below 30° C.; g) Cool to room temperature quickly.

2. Alternatively, cooling may be carried out slowly with stirring by simply leaving the container with the contents stirring in a room, which is at room temperature. Note that whilst cooling at stage f. is preferred to about below 30° C. before adding sensitive ingredients, such as tetracycline antibiotics, for formulations with less (or no sensitive) ingredients cooling may optionally be to about below 35° C. (or about below 40° C.).

In some cases the API's may be added at step 3 with moderate mixing.

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Canisters Filling and Crimping

Each aerosol canister is filled with the pre-foam formulation ("PFF") and crimped with valve using vacuum crimping machine. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing

Propellant Filling

Pressurizing is carried out using a hydrocarbon gas or gas mixture. Canisters are filled and then warmed for 30 seconds in a warm bath at 50° C. and well shaken immediately thereafter.

Closure Integrity Test.

Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.

Tests

By way of non-limiting example the objectives of hardness, collapse time and freeze-thaw cycle ("FTC") stability tests are briefly set out below as would be appreciated by a person of the art.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can affect the degree of dermal penetration, efficacy, spreadability and acceptability to the user. The results can also be looked at as an indicator of softness. Note: the foam sample is dispensed into an aluminum sample holder and filled to the top of the holder.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 minute. Foams which are structurally stable on the skin for at least one minute are termed "short term stable" compositions or foams.

Density

In this procedure, the foam product is dispensed into vessels (including dishes or tubes) of a known volume and weight. Replicate measurements of the mass of foam filling the vessels are made and the density is calculated. The canister and contents are allowed to reach room temperature. Shake the canister to mix the contents and dispense and discard 5-10 mL. Then dispense foam into a preweighed tube, filling it until excess is extruded. Immediately remove (level off) excess foam at both ends and weigh the filled tube on the weighing balance.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000CP, the viscosity at 1 RPM may be measured, although the figures are of a higher magnitude.

FTC (Freeze Thaw Cycles)

Foam appearance under extreme conditions of repeated heating and cooling is evaluated by cycling through cooling, heating, (first cycle) cooling, heating (second cycle) etc., conditions, commencing with −10° C. (24 hours) followed by +40° C. (24 hours) and measuring the appearance following each cycle. The cycle is repeated for up to three times.

Chemical Stability

The amount of active agent present is analyzed in foam expelled from various pressurized canisters containing foam formulations using HPLC. Analysis is carried out at zero time and at appropriate time intervals thereafter. The canisters are stored in controlled temperature incubators at one or more of 5 C, at 25 C, at, 40 C and at 50 C. At appropriate time intervals canisters are removed and the amount of active agent in the foam sample is measured.

Visual Stability Tests

Spillability

An objective in designing formulations it to formulate so the composition does not lose fluidity, and stays spillable after the incorporation of active agent. Spillability means free moving or rotating of formulation inside the glass bottle upon inversion.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels.

Microscope Size:

The light microscope enables observing and measuring particles from few millimeters down to one micron. Light microscope is limited by the visible light wavelength and therefore is useful to measuring size of particles above 800 nanometers and practically from 1 micron (1,000 nanometers).

Shakability

Shakability represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non-shakable. This property may be of particular importance in cases where shaking is required for affecting proper dispersion of the contents.

Shakability Scoring:

| Shakability | |
|---|---|
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

Uniformity

Intra-Canister Uniformity

1. Representative product containers are collected, sample test solutions are prepared and the content of the analyte is determined according to standard methods in the art. Variability of content is characterized as percent difference or relative standard deviation, as appropriate, according to the number of samples evaluated.

2. The results ascertain variability or uniformity within a given container in content of analytes (primarily active pharmaceutical ingredients, but also preservatives) taken from different parts of a pressurized canister drug products 3. Two full canisters were shaken according to product instructions. About 1-3 g of Foam was dispensed from each canister and discarded. Foam sufficient for two replicate sample solution preparations was then dispensed into a glass beaker. This represents the initial sample. A middle portion is then dispensed from each canister being about half the canister contents. This middle dispensed portion may be discarded or collected for testing purposes, as necessary. Foam sufficient for two replicate sample solution preparations was then dispensed into a glass beaker. This represents the final sample. A small amount of formulation remains in the canister. The foam samples were stirred to remove gas/air bubbles. From both the initial and final foam portions from each canister 4 separate sample solutions are prepared and analyzed, 2 from the initial portion and 2 from the final portion. The percent difference is calculated as follows:

$$\frac{\text{Difference between content determined in initial \& final portions}}{\text{Mean of content of initial \& final portions}} \times 100$$

and the intra canister uniformity evaluated from the results.

Stock Compositions

Non-limiting examples of how stock solutions are made up with and without API are illustrated. Other stock solutions may be made using the same methodology by simply varying adding or omitting ingredients as would be appreciated by one of the ordinary skills in the art.

EXAMPLES

The invention is described with reference to the following examples. For the purpose of the Examples below it was sufficient to apply a vacuum only at the crimping stage although for long term stability preferably any vacuum should be applied during manufacture as well at a sufficient pressure so that any oxygen remaining in the formulation is virtually negligible. This invention is not limited to these examples and experiments. Many variations will suggest themselves and are within the full intended scope of the appended claims.

A list of the chemical constituents of the Brand names of some of the ingredients, used in some of the formulations appears in below in Table 3.

TABLE 3

Ingredient List

| Ingredients | brand name | category | HLB | RHLB |
|---|---|---|---|---|
| heavy mineral oil | Paraffin oil liquid heavy | Emollient | | 10.5 |
| light mineral oil | Pionier 2076P | Emollient | | 10.5 |
| capric/caprylic triglyceride | Myritol 318 | Emollient | | 5 |
| cyclomethicone | Dow Corning ® 345 Fluid | Emollient | | 7.75 |
| dimethicone | Dow Corning 200 ® Fluid, 350 cST | Emollient | | 5 |
| cyclohexasiloxane and cyclopentasiloxane | DOW Corning ® 246 Fluid | Emollient | | |
| phenyltrimethicone | DOW Corning ® 556 Fluid | Emollient | | |
| dimethiconol | ST - Dimethiconol 40 | Emollient | | |
| cyclotetrasiloxane | DOW Corning ® 244 Fluid | Emollient | | |
| stearyl dimethicone | DOW Corning ® 2503 WAX | Emollient | | |
| octyl dodecanol | eutanol | Emollient | | |
| stearyl alcohol | Speziol C18 Pharma | foam adjuvant | | 15.5 |
| cetostearyl alcohol | | foam adjuvant | | |
| cetearyl alcohol | | foam adjuvant | | |
| myristyl alcohol | | foam adjuvant | | |
| PPG 15 stearyl ether triethanolamine | | surfactant | | |
| cetearyl alcohol and cetearyl glucoside | Montanov 68 | surfactant | | |
| C14-C22 alkyl alcohol C12-C20 alkyl glucoside | Montanov L | surfactant | | |
| PEG 100 stearate | Polyoxyl 100 stearate Mirj 59 | surfactant | | |
| glycerol monostearate | Cutina GMS V PH | surfactant | | 3.8 |
| glycerol oleate | Monomuls 90-018 | surfactant | | |
| sorbitan oleate | Span 80 | | | 4.3 |
| steareth-2 | Brij 72 | surfactant | | 4.9 |
| sorbitan stearate | Span 60 | surfactant | | 4.7 |
| methyl glucose sesquistearate | TEGO Care PS | surfactant | | 6.6 |
| sucrose stearic acid esters D-1805 | sufhope SE D-1805 | surfactant | | 5 |
| sorbitan palmitate | Span 40 | surfactant | | 6.7 |
| butylated hydroxyl toluene α-tocopherol | | API and oil | | |
| calcipotriol hydrate | | API | | |
| clindamycin phosphate | | API | | |
| acyclovir | | API | | |
| azelaic acid | | API and modulating agent | | |
| calcitriol | | API | | |
| propane + butane + isobutene (A-46 or 1681) | | Propellant | | |

Section 1—Silicones

Section 1 Part A —Silicone Carriers without API's

Example 1

Slow vs. Rapid Cooling with Heavy Mineral Oil/Cyclomethicone/Glycerol Monostearate Formulation

| Ingredients | 01- A | 01- B | 04- C |
|---|---|---|---|
| Procedure | (I) Slow cooling to 40° C. (II) Slow to RT | (I) Rapid cooling to 40-45° C. (II) Slow to RT | (I) Rapid cooling to 30° C. (II) Slow to RT |
| Heavy mineral oil | 86.00 | 86.00 | 86.00 |
| Glycerol monostearate (GMS) | 4.00 | 4.00 | 4.00 |
| Cyclomethicone 5-NF | 10.00 | 10.00 | 10.00 |
| Total | 100.00 | 100.00 | 100.00 |
| Propellant | 8.00 | 8.00 | 8.00 |
| Results PFF | | | |
| Viscosity 10 RPM | 5678.79 (day 1), 7294.44 (day 6) | 7870.32 (day 1), 7246.46 (day 6) | 4958.94 (day 1) |
| Foam | | | |
| Quality | Good | Good | Excellent |
| Color | white | white | white |
| Odor | No odor | No odor | No odor |
| Shakability | good | Good | Good |
| Density | 0.118 | 0.105 | 0.150 |
| Hardness | 15.76 | 14.69 | ND |

Procedure A (01): Heavy mineral oil was heated to ~60 C, followed by the addition of glycerol monostearate until fully dissolved. The mixture was cooled slowly to 40-45° C. Cyclomethicone 5-NF was added with vigorous agitation at 40-45° C. The mixture was cooled to room temperature.

Procedure B (01): Heavy mineral oil was heated to ~60 C, followed by the addition of glycerol monostearate until fully dissolved. The mixture was cooled rapidly to 40-45° C. using an ice bath. Cyclomethicone 5-NF was added with vigorous agitation at 40-45° C. The mixture was cooled to room temperature.

Procedure C (04): Heavy mineral oil was heated to ~60 C, followed by the addition of glycerol stearate until fully dissolved. The mixture was cooled rapidly to 30° C. using an ice bath. Cyclomethicone 5-NF was added with vigorous agitation at 30° C. The mixture was cooled to room temperature.

Foam quality was good following procedures A and B. Foam quality of formulation prepared by procedure C (fast cooling to 30° C.) gave excellent quality. This finding confirms the importance of fast cooling procedure during the manufacturing. Unexpectedly the viscosity testing demonstrated large difference was demonstrated in PFF viscosity on day 1. The PFF produced by slow cooling demonstrated lower initial viscosity. Interestingly the viscosity difference was diminished following six days at room temperature. The color of the PFF was dull following the slow procedure and bright for the fast procedure. Density was slightly higher using the slow procedure. Although cyclomethicone 5-NF is considered volatile, its boiling point is 205° C. and no evaporation of cyclomethicone 5-NF was detected which emphasizes its role in foam quality.

The effect of cooling may vary depending on the formulation content and possibly the amount of cooling and that the effect of rapid cooling to below about 35° C. or perhaps preferably to below about 30° C. may be more significant than rapid cooling to about 40-45° C.

Accordingly, in some embodiments, the compositions described herein are prepared by a process that slowly cools the mixture, thereby improving the feel of the prefoam formulation. In some embodiments, the compositions described herein are prepared by a process that rapidly cools the mixture, thereby resulting in a prefoam formulation having a higher viscosity.

Example 2

Slow vs. Rapid with Light+Heavy Mineral Oil Mixture/Cyclomethicone 5-NF/Glycerol Monostearate Formulation Effect of Cooling on Manufacture

| Ingredients | 133--P(A) | 133--P(B) |
|---|---|---|
| Procedure | Rapid cooling to 30° C. | Slow cooling to RT |
| Heavy mineral oil | 25.00 | 25.00 |
| Light mineral oil | 61.00 | 61.00 |

-continued

| Ingredients | 133--P(A) | 133--P(B) |
|---|---|---|
| Glycerol monostearate | 4.00 | 4.00 |
| Cyclomethicone 5-NF | 10.00 | 10.00 |
| Total | 100.00 | 100.00 |
| Propellant | 8.00 | 8.00 |
| Results PFF | | |
| Viscosity (cPi) | 10765.7 | 1393.7 |
| Microscopic examination | Uniform preparation | Uniform preparation |
| Visual inspection | Homogeneous. | Non-homogeneous; phase separation 10/90 |
| Foam | | |
| Quality | Good | Fairly Good |
| Color | white | white |
| Odor | No odor | No odor |
| Shakability | good | good |
| Density (g/mL) | 0.098 | 0.089 |
| Microscopic observation | Uniform particles distribution | Uniform particles distribution; |
| Hardness (g) | 14.95 | 12.58 |
| Bubble size (μm) | 61 micron standard deviation = 34 | 135 Standard deviation = 113 |

A batch of formulation 133 was prepared in two different ways, part with slow cooling and part with fast cooling. The fast cooling was achieved by immersing the container into an ice bath with stirring to reach room temperature whilst the other part was merely left to cool to room temperature with stirring without any external bath.

Procedure A 133-P(A): Mineral oil was heated to ~60° C., followed by the addition of glycerol monostearate until full dissolution. The mixture was cooled rapidly to 30-33° C. using an ice bath, cyclomethicone 5-NF was added in one portion. The mixture was allowed to reach room temperature while stirring.

Procedure B 133-P (B): Mineral oil was heated to ~60° C., followed by addition of glycerol monostearate until fully dissolved. The mixture was cooled slowly to room temperature. Cyclomethicone 5-NF was added at 30-33° C. while stirring. The mixture was allowed to reach room temperature while stirring.

The data demonstrate that, surprisingly, foam quality appears to be better when the formulation is subjected to rapid cooling.

Surprisingly it has been observed that the appearance of the pre-foam formulation before addition of propellant is different depending on the rate of cooling applied to the formulation at the end of the manufacturing process.

Foam quality was designated as good following the fast cooling procedure in comparison to a fairly good foam following the slow cooling procedure. The foam was also more stable. Bubble size of foam prepared by fast cooling procedure was smaller in comparison to bubble size of the foam prepared by slow cooling procedure.

Example 3

Mode of Cyclomethicone 5-NF Addition to Formulation with Light+Heavy Mineral Oil Mixture/Cyclomethicone 5-NF/Glycerol Monostearate (GMS) Formulation.

| Composition | 133-P(A) | 133-P(C) | 133-P(D) | 133-P(E) |
|---|---|---|---|---|
| Procedure | (I) Instant cooling to 30° C. (II) to RT | (I) Instant cooling to 27-30° C. (II) to RT | (I) Instant cooling to 20-25° C. (II) to RT | (I) Instant cooling to 15-20° C. (II) to RT |
| Light Mineral Oil | 25.00 | 25.00 | 25.00 | 25.00 |
| Heavy Mineral Oil | 59.91 | 59.91 | 59.91 | 59.91 |
| GMS | 4.00 | 4.00 | 4.00 | 4.00 |
| Cyclomethicone 5-NF | 10.00 | 10.00 | 10.00 | 10.00 |
| PFF | | | | |
| Viscosity (cPi) | 10765.7 | 11581.53 | 8318.23 | 7966.3 |
| Microscopic observation | Uniform preparation | Uniform preparation | Uniform preparation | Uniform preparation |
| Visual inspection | Homogenous. | Homogenous. | Homogenous. | Homogenous. |

-continued

| Composition | 133-P(A) | 133-P(C) | 133-P(D) | 133-P(E) |
|---|---|---|---|---|
| Foam | | | | |
| Quality | Good | Excellent | Good to Excellent | Excellent |
| Color | White, | White, | White | White |
| Shakability | Good | Good | Good | Good |
| Density (g/mL) | 0.098 | 0.075 | 0.067 | 0.068 |
| Microscopic observation | Uniform particles distribution | Uniform particles distribution | Uniform particles distribution | Uniform particles distribution |
| Hardness (g) | 14.95 | 13.03 | 11.51 | 13.11 |
| bubble size(μm) | 61 micron standard deviation = 34 | 83 micron standard deviation = 43 | 161 micron standard deviation = 97 | 96 micron standard deviation = 60 |
| Uniformity of formulation in pressurized glass bottles | Homogenous | Non-homogenous; reversible | Non-homogenous; reversible | Non-homogen. reversible |

133-P(A): The mixture of light and heavy mineral oils was heated to 60° C., followed by addition of glycerol monostearate until full dissolution. The mixture was cooled rapidly to 30° C. using an ice bath. Cyclomethicone 5-NF was added in one portion at 30° C. while stirring. The mixture was allowed to reach room temperature while stirring.

133-P(C): The mixture of light and heavy mineral oils was heated to 60° C. ¾ of cyclomethicone 5-NF amount was added while stirring at 60° C., followed by addition of glycerol monostearate until full dissolution. The mixture was cooled rapidly to 27-30° C. using an ice bath. Quarter (¼) of total cyclomethicone 5-NF amount was added at 27-30° C. while stirring. The mixture was allowed to reach room temperature while stirring.

133-P(D): The mixture of light and heavy mineral oils was heated to 60° C., followed by addition of glycerol monostearate until full dissolution. The mixture was cooled rapidly to 20-25° C. using an ice bath. Cyclomethicone 5-NF was added in one portion at 23° C. while stirring. The mixture was allowed to reach room temperature while stirring.

133-P(E): The mixture of light and heavy mineral oils was heated to 60° C., followed by addition of glycerol monostearate until full dissolution. The mixture was cooled rapidly to 15-20° C. using an ice bath. Cyclomethicone 5-NF was added in one portion at 18° C. while stirring. The mixture was allowed to reach room temperature while stirring.

Addition of cyclomethicone 5-NF in two portions improved the foam quality from good to excellent. Fast cooling of mineral oils and glycerol monostearate mixture to lower temperature 15-20° C. compared to 30° C. improved foam quality. Addition of cyclomethicone 5-NF in one portion cause the formulation to be homogenous however, non-homogeneity that was observed in formulations 133-P(c), 133-P(D) and 133-P(E) was reversible by inversion of the bottle.

This data confirms the importance of fast cooling procedure and verifies that when cyclomethicone is added at lower temperature, the foam quality is higher.

Example 4

Various Concentrations of Cyclomethicone 5-NF with Heavy Mineral Oil Mixture/Cyclomethicone 5-NF/Glycerol Monostearate Formulation

| Ingredients | 014 | 06 | 07 |
|---|---|---|---|
| Procedure | (I) Instant cooling to 30° C. (II) to RT | | |
| Heavy mineral oil | 91.00 | 76.00 | 66.00 |
| Glycerol monostearate | 4.00 | 4.00 | 4.00 |
| Cyclomethicone 5-NF | 5.00 | 20.00 | 30.00 |
| Ratio GMS:CM | 4:5 | 1:5 | 2:14 |
| Total | 100.00 | 100.00 | 100.00 |
| Propellant | 8.00 | 8.00 | 8.00 |
| Results | PFF | | |
| Viscosity 10 RPM | 7022 | 5166 | 5342 |
| Foam | | | |
| Quality | Good | Fairly Good | Fairly Good |
| Color | White | White | White |
| Odor | No odor | No odor | No odor |
| Shakability | Good | Good | Good |
| Density | 0.157 | 0.136 | 0.115 |
| Hardness | 21.78 | 8.78 | 9.26 |

Heavy mineral oil was heated to —60° C., followed by the addition of glycerol monostearate until fully dissolved. The mixture was cooled rapidly to 30° C. using an ice bath. Cyclomethicone 5-NF was added with vigorous agitation at 30° C. The mixture was cooled to room temperature.

Foam quality was reduced from Good to fairly good by using higher concentration of cyclomethicone without changing the concentration of glycerol monostearate (see the formulations 014, 06 and 07). Foam quality of formulation 06 was significantly improved by addition of glycerol monostearate.

Hardness of the foam was reduced when higher percentage of cyclomethicone 5-NF was used.

In the above mentioned formulations, 014, 006, 007, high concentrations of cyclomethicone 5-NF result in low foam quality. Therefore the question posed was whether the GMS/CM ratio is of importance to the foam quality.

Example 5

Comparative Studies of Silicone Compounds Heavy Mineral Oil Mixture/Glycerol Monostearate Formulation

| Ingredients | 20 | 21 | 022 | 035- | 023 | 024 | 025 |
|---|---|---|---|---|---|---|---|
| Procedure | | | Instant cooling to 30° C. | | | | |
| Heavy mineral oil | 86.00 | 86.00 | 86.00 | 86.00 | 86.00 | 86.00 | 86.00 |
| Glycerol monostearate | 4.00 | 4.00 | 4.00 | 4.00 | 4.00 | 4.00 | 4.00 |
| Dow Corning 246 fluid (d5 + d6) | 10.00 | | | | | | |
| Dimethiconol | | 10.00 | | | | | |
| Dimethicone 1.5 | | | 10.00 | | | | |
| Dimethicone 350 | | | | 10.00 | | | |
| Phenyltrimethicone | | | | | 10.00 | | |
| Dow Corning 244 cyclotetrasiloxane | | | | | | 10.00 | |
| Stearyl dimethicone | | | | | | | 10.00 |
| Total | 100.00 | 100.00 | 100.00 | 100.00 | 100.00 | 100.00 | 100.00 |
| Propellant | 8.00 | 8.00 | 8.00 | 8.00 | 8.00 | 8.00 | 8.00 |
| Results PFF | | | | | | | |
| Viscosity 10 RPM | 8782 | 4191 | 1762 | 914.81 | 7390 | 2397.49 | 5118.91 |
| Foam | | | | | | | |
| Quality | Good | Good | Fairly Good | Fairly Good | Good | Good | Excellent |
| Color | White | White | White | White | White | White | White |
| Odor | No odor | No odor | No odor | No odor | No odor | No odor | No odor |
| Shakability | Good | Good | Good | Good | Good | Good | Good |
| Density | 0.158 | 0.175 | Not tested due to fairly good foam quality | Not tested due to fairly good foam quality | 0.202 | 0.198 | 0.214 |
| Hardness | 15.65 | 13.50 | Not tested due to fairly good foam quality | Not tested due to fairly good foam quality | 16.58 | 20.48 | 29.65 |

Heavy mineral oil was heated to ~60° C., followed by the addition of glycerol stearate until full dissolution. The mixture was cooled rapidly to 30° C. using an ice bath. Siloxane compounds were added with vigorous agitation at 30° C. The mixture was brought to room temperature while stirring.

TABLE 4

Comparison of different silicones (incorporated in the same base formulation in the same amount) and resultant foam properties

| Siloxane | Viscosity (cPi) | Structure | volatility | Foam Quality | See Example |
|---|---|---|---|---|---|
| Dow corning 246 Fluid (d6 + d5) (cyclohexasiloxane & cyclopentasiloxane) | 6.8 | cyclic | + | Good | 21 |
| Dimethiconol | 41 | linear | | Good | 21 |
| Dimethicone 1.5 | 1.5 | linear | + | Fairly Good | 21 |
| Dimethicone 350 | 350 | linear | | Fairly Good | 1 |
| Phenyltrimethicone | 22.5 | linear | | Good | 21 |
| Dow Corning 244 Fluid (cyclotetrasiloxane) | 2.4 | cyclic | + | Good | 21 |
| Stearyl dimethicone | 40 (at 40° C.) | linear | | Good | 21 |
| Cyclomethicone 5-NF | 4 | cyclic | + | Good - Excellent | 1 |

Without being bound to any theory, the quality of foam consisting of mineral oil, glycerol monostearate and silicones, relates to the spatial structure of silicones used. When cooled rapidly, Mineral oil and glycerol monostearate create a stable structure. Silicones such as Cyclomethicone 5-NF, Dow Corning 244 Fluid, and Dow corning 246 Fluid all posses a cyclic structure. This cyclic structure may deprive them from penetrating in between the mineral oil/GMS structure, therefore it is thought that perhaps they do not affect the stability of mineral oil/GMS structure in a substantial way. Using such cyclic silicones therefore results in a high quality foam.

Linear silicones such as Dimethicone 1.5 and Dimethicone 350 have a hydrophobic chain-like structure. Since they may be capable of forming Van Der Waals interactions with the Glycerol monostearate/oil, it is thought—without being bound by any theory—that they are trapped between the hydrophobic chains of mineral oil. This may cause destabilization of hydrophobic-hydrophobic interactions between mineral oil chains and Glycerol monostearate, and thus decreases formulation stability. The result is a reduced foam quality, such as fairly good.

However, other linear silicones such as Phenyltrimethicone, Dimethiconol and stearyl dimethicone which consist of large structural moieties, may cause stearic hindrance and therefore, may be unable to destabilize the mineral oil/glycerol monostearate structure. The following mechanisms—without being bound by any theory—are suggested to explain this phenomenon:

1. Phenyl trimethicone has a benzyl ring and three methyl groups that create a structure which may not be able to penetrate in between the mineral oil/GMS and may not cause substantial destabilization.

2. Dimethiconol which has OH groups may not interact with the mineral oil significantly since it would create a repelling effect. Due to this effect dimethiconol may not penetrate in between the mineral oil/glycerol monostearate structure and destabilize it.

3. Stearyl dimethicone acts in the similar way to phenyl trimethicone in formulation due to its long linear aliphatic chains.

Example 6

Impact of Ratios of Glycerol Monostearate and Cyclomethicone 5-NF on Formulation Properties

| Ingredients | 036 | 033 | 06 |
|---|---|---|---|
| Procedure | (I) Instant cooling to 30° C. (II) to RT | | |
| Heavy mineral oil | 79.00 | 71.00 | 76.00 |
| Glycerol monostearate | 6.00 | 9.00 | 4.00 |
| Cyclomethicone 5-NF | 15.00 | 20.00 | 20.00 |
| Ratio GMS:CM | 4:5 | 4:5 | 1:5 |
| Total | 100.00 | 100.00 | 100.00 |
| Propellant | 8.00 | 8.00 | 8.00 |
| Results | | | |
| PFF | | | |
| Viscosity 10 RPM | 4926.95 | 8762.8 | 5166 |
| Foam | | | |
| Quality | Good | Good | Fairly Good |
| Color | White | White | White |
| Odor | No odor | No odor | No odor |
| Shakability | Good | Good | Good |
| Density | 0.144 | 0.130 | 0.136 |
| Hardness | 11.09 | 10.77 | 8.78 |

Heavy mineral oil was heated to ~60 C, followed by the addition of glycerol monostearate until fully dissolved. The mixture was cooled rapidly to 30° C. using an ice bath. Cyclomethicone 5-NF was added with vigorous agitation at 30° C. The mixture was cooled to room temperature while stirring.

Foam Quality was good when Glycerol monostearate to Cyclomethicone 5-NF ratio was 2.5. Apparently the ratio between Glycerol monostearate and cyclomethicone 5-NF plays a role in the foam quality. When the ratio was higher than about 4:5 (e.g. 06 and 07) foam quality was reduced to fairly good. Therefore, in order to maintain good foam, the recommended ratio between Glycerol monostearate and cyclomethicone 5-NF should be preferably 1:1 to 1:4 by weight.

Section 1 PART B—Silicone Carriers with API's

Example 7

Heavy Mineral Oil, Glycerol Monostearate and Cyclomethicone 5-NF a Volatile Silicone with Various API's A) Soluble API's

| Ingredients | 18A | 18B |
|---|---|---|
| Procedure | (I) Rapid cooling to 40-45° C., (II) to RT | |
| Heavy Mineral Oil | 68.80 | 85.99 |
| Glycerol monostearate | 3.20 | 4.00 |
| Cyclomethicone 5-NF | 8.00 | 10.00 |
| α-Tocopherol | 20.00 | |
| Calcipotriol | | 0.01 |
| Total | 100.00 | 100.00 |
| Propellant (propane + butane + isobutene) A46 | 12.00 | 12.00 |
| RESULTS PFF[1] | | |
| Viscosity (10 RPM) | 2147.54 | 5006.93 |
| Microscope | No Crystals | No Crystals |
| FOAM | | |
| Foam Quality | Good | Good |
| Color | Off-White | White |
| Odor | No Odor | No Odor |
| Shakability | Good | Good |
| Density | 0.090 | 0.082 |
| Collapse Time (36° c.-Sec.) | >300/FG | >300/FG |
| Bubble Mean Size (Mm) | 82.00 | 118.00 |
| Bubbles Above 500 Mm (%) | 0.00 | 0.00 |
| Microscope | No Crystals | No Crystals |
| FTC | | |
| Foam Quality | Fairly Good | Good |
| Color | Off-White | White |
| Odor | No Odor | No Odor |
| Shakability | Good | Good |
| Microscope | No Crystals | No Crystals |

[1]Prefoam Formulation

Heavy mineral oil was heated to about 60° C. followed by the addition of glycerol stearate until fully dissolved. The mixture was cooled rapidly to about 40-45° C. Cyclomethicone 5-NF was added with vigorous agitation and cooled to room temperature. API was added with stirring.

The combination of heavy mineral oil, glycerol monostearate, cyclomethicone 5-NF, and a-tocopherol or calcipotriol produces a good stable foam. Formulation B, containing calcipotriol produces a slightly improved foam, particular following repeated freeze thaw cycling. This improved foam quality may be due in part to the higher viscosity of formulation B, as tocopherol is an oil.

B) Suspended API's

| Ingredients | 18C | 18D | 18E |
|---|---|---|---|
| Procedure | (I) Rapid cooling to 40-45° C., (II) RT | | |
| Heavy Mineral Oil | 84.28 | 81.70 | 73.10 |
| Glycerol monostearate (GM) | 3.92 | 3.80 | 3.40 |
| Cyclomethicone 5-NF | 9.80 | 9.50 | 8.50 |
| Clindamycin Phosphate | 2.00 | | |
| Acyclovir | | 5.00 | |
| Azelaic acid | | | 15.00 |
| Total | 100.00 | 100.00 | 100.00 |
| Propellant(propane + butane + isobutene) A46 | 12.00 | 12.00 | 12.00 |
| RESULTS PFF | | | |
| Viscosity (10 RPM) | 767.84 | 1069.77 | 12957.23 |
| Microscope | Crystals | Crystals | Crystals |
| FOAM | | | |
| Foam quality | Good | Good | Good |
| Color | White | White | White |
| Odor | No odor | No odor | No odor |
| Shakability | Good | Good | Moderate |
| Density | 0.103 | 0.097 | 0.108 |
| Collapse Time (36 C.-Sec.) | >300/FG | >300/FG | >300/FG |
| Bubble Mean Size (Mm) | 89.00 | 124.00 | 168.00 |
| Bubbles Above 500 Mm (%) | 0.00 | 0.00 | 0.00 |
| Microscope | Crystals, Uniform Dispersion | Crystals, Uniform Dispersion | Crystals, Uniform Dispersion |
| FTC | | | |
| Foam quality | Good | Good | Fairly Good |
| Color | White | White | White |
| Odor | No Odor | No Odor | No Odor |
| Shakability | Good | Good | Good |
| Microscope | Crystals, Uniform Dispersion | Crystals, Uniform Dispersion | Crystals, Uniform Dispersion |

The combination of mineral oil, glycerol monostearate and cyclomethicone 5-NF produces good stable foam that is not adversely effected by one or more of API, its concentration and its solubility in oil (for example, α-tocopherol is soluble in oil, whereas clindamycin phosphate is suspended).

Example 9

Heavy Mineral Oil, Glycerol Monostearate and Dimethicone 350 cst, a Non-Volatile Silicone with Various API's A) Soluble API's

| Ingredients | 19A | 19B |
|---|---|---|
| Procedure | (I) Rapid cooling to 35-40° C., (II) to RT | |
| Heavy Mineral Oil | 68.80 | 85.99 |
| Glycerol monostearate | 3.20 | 4.00 |
| Dimethicone (350 cst) | 8.00 | 9.99 |
| α-tocopherol | 20.00 | |
| Calcipotriol hydrate | | 0.01 |
| Total | 100.00 | 100.00 |
| Propellant(propane + butane + isobutene) A46 | 12.00 | 12.00 |

| Ingredients | 19A | 19B |
|---|---|---|
| RESULTS PFF | | |
| Viscosity (10 RPM) | 595.87 | 1302.72 |
| Foam | | |
| Foam Quality | Fair | Fair |
| Color | Off-White | White |
| Odor | No Odor | No Odor |
| Shakability | Good | Good |

Heavy mineral oil was heated to about 50-55° C. followed by the addition of glycerol stearate until fully dissolved. The mixture was cooled rapidly to about 35-40° C. Dimethicone 350 was added with vigorous agitation and cooled to room temperature. API was added with stirring.

Comparison of 19A with 18A of Example 1 and comparison of Example 19B with 18B of Example 1, discloses that unexpectedly the volatile silicone cyclomethicone 5-NF produces foam of a higher quality than similar amounts of its non-volatile counterpart dimethicone.

B) Suspended API's

| Ingredients | 19C | 19D | 19E |
|---|---|---|---|
| Procedure | (I) Rapid cooling to 35-40° C., (II) to RT | | |
| Heavy Mineral Oil | 84.28 | 81.70 | 73.10 |
| Glycerol monostearate | 3.92 | 3.80 | 3.40 |
| Dimethicone 350 | 9.80 | 9.50 | 8.50 |
| Clindamycin Phosphate | 2.00 | | |
| Acyclovir | | 5.00 | |
| Azelaic acid | | | 15.00 |
| Total | 100.00 | 100.00 | 100.00 |
| Propellant(propane + butane + isobutene) A46 | 12.00 | 12.00 | 12.00 |
| RESULTS PFF | | | |
| Viscosity (10 RPM) | 953.8 | 1312.72 | 11053.64 |
| Foam | | | |
| Foam Quality | Fair | Fairly Good | Fairly Good |
| Color | White | White | White |
| Odor | No Odor | No Odor | No Odor |
| Shakability | Good | Good | Good |

Parallel formulations to those seen in Example 1 were prepared with a non-volatile silicone. In all the examples in A and B the foam quality was substantially reduced. Likewise, comparison of 19C with 18C of Example 1 and comparison of Example 19D with 18D of Example 1, and comparison of Example 19E with 18E of Example 1, also discloses that unexpectedly the volatile silicone cyclomethicone 5-NF produces foam of a higher quality than similar amounts of its non-volatile counterpart dimethicone. Thus, dimethicone 350 (a non-volatile silicone) may be acting as a stronger defoamer.

Example 10

Comparison Between a Formulation with a Volatile Silicone and Partial Rapid Cooling to 40-45° C. and a Formulation with a Combination of 2 Silicones One of which is Volatile with Slow Cooling

| Ingredients | 23E | 18E |
| --- | --- | --- |
| Procedure | (I) Slow cooling to 30-35° C., (II) Slow to RT | (I) Rapid cooling to 40-45° C., (II) Slow to RT |
| Heavy Mineral Oil | 61.00 | 73.10 |
| Glycerol monostearate | 4.00 | 3.40 |
| Dimethicone (350 cst) | 10.00 | |
| Cyclomethicone 5-NF | 10.00 | 8.50 |
| Azelaic acid | 15.00 | 15.00 |
| Total | 100.00 | 100.00 |
| Propellant(propane + butane + isobutene) A46 | 12.00 | 12.00 |
| RESULTS PFF | | |
| Viscosity (10 RPM) | 8014.29 | 12957.23 |
| Foam | | |
| Foam Quality | Fair | Good |
| Color | White | White |
| Odor | No Odor | No Odor |
| Shakability | Good | Good |

Procedure for 18E—see Example 1

Procedure for 23E—Heavy mineral oil was heated to about 50-55° C. followed by the addition of glycerol monostearate until fully dissolved. The mixture was cooled to about 30-35° C. Cyclomethicone 5-NF was added with vigorous agitation and cooled to room temperature. Azelaic acid was added with stirring.

Adding a non-volatile silicone (dimethicone 350) to a volatile (cyclomethicone) silicone results in a significant reduction in foam quality, which in part may possibly be attributed to the slow cooling. Thus, the negative defoaming character of the non-volatile silicone dimethicone 350 overrides the positive unexpected foaming effect of the volatile cyclic silicone cyclomethicone.

Section 2—Surfactants

See above Example 6 for Study on Impact of Ratio of Glycerol Monostearate and Cyclomethicone 5-NF This study demonstrates the preferred ratio between Glycerol monostearate and cyclomethicone should be preferably 4:5 to 1:4 by weight.

Example 11

Comparison Between a Surfactant Glycerol Monostearate and a Foam Adjuvant Stearyl Alcohol with Heavy Mineral Oil in the Presence of Cyclomethicone 5-NF

| Ingredients | 21C | 18C |
| --- | --- | --- |
| Procedure | (I) Rapid cooling to 40- 45° C., (II) Rapid to RT | (I) Rapid cooling to 40-45° C., (II) RT |
| Heavy Mineral Oil | 84.28 | 84.28 |
| Glycerol monostearate | | 3.92 |
| Stearyl alcohol | 3.92 | |
| Cyclomethicone 5-NF | 9.80 | 9.80 |
| Clindamycin Phosphate | 2.00 | 2.00 |
| Total | 100.00 | 100.00 |
| Propellant(propane + butane + isobutene) A46 | 12.00 | 12.00 |
| RESULTS PFF | | |
| Viscosity (10 RPM) | 110.98 | 767.84 |
| Foam | | |
| Foam Quality | Fair | Good |
| Color | White | White |
| Odor | No Odor | No Odor |
| Shakability | Good | Good |
| Density | N/M | 0.103 |
| Collapse Time (36 C.-Sec.) | N/M | >300/FG |
| Bubble Mean Size (Mm) | N/M | 89.00 |
| Bubbles Above 500 Mm (%) | N/M | 0.00 |

N/M = Not measured

Replacing glycerol monostearate with stearyl alcohol (which is a wax, but not a surfactant) results in a significant reduction in foam quality. Thus foam adjuvant alone without surfactant is not able to produce quality foam form oil with silicone.

Procedure for 18C—see example 1

Procedure for 21 C: Heavy mineral oil was heated to about 50-55° C. followed by the addition of stearyl alcohol until fully dissolved. The mixture was cooled rapidly to about 40-45° C. Cyclomethicone was added with vigorous agitation and cooled rapidly to room temperature. Clindamycin Phosphate was added.

Example 12

Comparison Between Span 80 (a Sorbitan Ester, Liquid Surfactant) and Glycerol Monostearate (Solid Surfactant)

| Ingredients | 22B | 18B |
|---|---|---|
| Procedure | (I) Cooling to 40-45° C. (II) Rapid to RT | (I) Rapid cooling to 40-45° C. (II) RT |
| Heavy Mineral Oil | 85.99 | 85.99 |
| Span 80 (sorbitan ester) -liquid | 3.99 | |
| Glycerol monostearate -solid | | 3.99 |
| Cyclomethicone 5-NF | 10.00 | 10.00 |
| Calciporiol hydrate | 0.01 | 0.01 |
| Total | 100.00 | 100.00 |
| Propellant(propane + butane + isobutene) A46 | 12.00 | 12.00 |
| RESULTS PFF | | |
| viscosity (10 RPM) | 73.98 | 5006.93 |

| Ingredients | 22B | 18B |
|---|---|---|
| FOAM | | |
| Foam quality | Fair | Good |
| Color | White | White |
| Odor | No odor | No odor |
| Shakability | Good | Good |
| Density | N/M | 0.082 |
| Collapse time (36 C.-sec.) | N/M | >300/FG |
| Bubble mean size (μm) | N/M | 118.00 |
| Bubbles above 500 μm (%) | N/M | 0.00 |

N/M = Not measured

Procedure: for 18B—see Example 1

Procedure for 22B: Heavy mineral oil was heated to about 50-55° C. followed by the addition of Span80 until fully dissolved. The mixture was cooled to about 40-45° C. Cyclomethicone 5-NF was added with vigorous agitation and cooled rapidly to room temperature. Calcipotriol hydrate was added with stirring.

Replacing a solid surfactant (glycerol monostearate) with a sorbitan ester which is liquid results in a significant reduction in foam quality. Liquid sorbitan esters on their own did not result in foams of quality.

Example 13

Comparison of Four Surfactants, Two from Glycerol Fatty Acid Derivatives—and Two from Alkyl Alcohol/Alkyl Glucosides

| Ingredients | 04-C | 038 | 040 | 039 | 045 |
|---|---|---|---|---|---|
| Procedure | (I) Rapid to 30-35° C. (II) RT | (I) Rapid to 27-30° C. (II) RT | | | |
| Heavy Mineral Oil | 86.00 | 86.00 | 86.00 | 86.00 | 86.00 |
| Glycerol monostearate | 4.00 | | | | |
| Glycerol oleate (Monomuls 90-018) | | 4.00 | | | |
| Montanov 68 (cetearyl alcohol and cetearyl glucosides) | | | 4.00 | | |
| Montanov L (C14-C22 Alkylalcohol and C12-20 Alkylglucoside) | | | | 4.00 | |
| Glycerol palmitostearate | | | | | 4.00 |
| Cyclomethicone 5-NF | 10.00 | 10.00 | 10.00 | 10.00 | 10.00 |
| Total | 100.00 | 100.00 | 100.00 | 100.00 | 100.00 |
| Propellant(propane + butane + isobutene) A70 | 8.00 | 8.00 | 8.00 | 8.00 | 8.00 |
| RESULTS PFF | | | | | |
| Viscosity (10 RPM) | 4958.94 | 984.79 | 797.83 | 486.9 | Not tested |
| Foam | | | | | |
| Foam Quality | Excellent | Fair | Fairly good | Fairly good | Excellent |
| Color | white | white | white | white | white |
| Odor | No odor | No odor | No odor | No odor | No odor |
| Shakability | Good | Good | Good | Good | Good |
| Density (g/mL) | 0.150 | NA | NA | 0.147 | 0.118 |
| Hardness | NA | NA | 5.37 | 7.52 | Not tested |

Mineral oil was heated to ~60-65° C., followed by the addition of glycerol stearate, until fully dissolved. The mixture was cooled instantly to 27-30° C. using an ice bath. Cyclomethicone 5-NF was added with vigorous agitation at 30° C. The mixture was cooled to room temperature.

Surprisingly, when a surfactant from the same family (glycerides of fatty acids)—Glycerol monooleate (Monomuls) was used, the foam quality was fairly good namely, it produced a poorer foam structure and was less effective than glycerol monostearate which consistently and unexpectedly produced foam of at least good quality. Viscosity was reduced in comparison to formulation 040. It may be assumed that the structural difference between oleate and stearate plays a role in the foam stability.

When Montanov family (68 and L) glycosides and fatty alcohols were employed (Montanov L which contains coco-glucoside and Montanov 68 which contains cetearyl alcohol and cetearyl glucoside—a combination of surfactant and foam adjuvant), the foam quality was fairly good to good namely foam quality was reduced compared to glycerol monostearate. Viscosity was also reduced in comparison to formulation 04-C. Interestingly Glycerol palmitostearate also produced foam of high quality.

Without being bound to any theory, it appears that glycerol monostearate plays a crucial part in the establishment of foam quality of oil/silicone formulations. This unique success of both glycerol monostearate and also glycerol palmitostearate alone is quite unexpected since it is known that glycerol mono and di stearate and other fatty acid monoesters are not efficient surfactants.

Example 14

Comparison of Fatty Acids Derivative Cetearyl Alcohol

| Ingredients | 041 |
|---|---|
| Procedure | (I) Rapid to 27-30° C. (II) to RT |
| Heavy Mineral Oil | 86.00 |
| Cetearyl alcohol | 4.00 |
| Cyclomethicone 5-NF | 10.00 |
| Total | 100.00 |
| Propellant(propane + butane + isobutene) A46 | 8.00 |
| RESULTS PFF | |
| Viscosity (10 RPM) | 768.84 |
| Foam | |
| Foam Quality | Fairly good |
| Color | White |
| Odor | No odor |
| Shakability | Good |
| Density | 0.168 |
| Hardness | 13.07 |

Mineral oil was heated to ~60-65° C., followed by the addition of glycerol stearate, until fully dissolved. The mixture was cooled instantly to 27-30° C. using an ice bath. Cyclomethicone 5-NF was added with vigorous agitation at 30° C. The mixture was cooled to room temperature.

This example presents the formulations prepared with fatty acids derivative Cetearyl alcohol and as foam adjuvant and surfactant respectively.

It appears that cetearyl alcohol which is a foam adjuvant alone provides foam of fairly good quality. The viscosity of the PFF was low in comparison to formulation 04.

Example 15

Surfactant Studies Glycerol Monostearate+PEG 100 Stearate

| Ingredients | 019-081027 |
|---|---|
| Heavy mineral oil | 86.00 |
| Glycerol monostearate + PEG 100 stearate | 4.00 |
| Cyclomethicone 5-NF | 10.00 |
| Total | 100.00 |
| Propellant | 8.00 |
| Results PFF | |
| Viscosity 10 RPM | |
| Foam | |
| Quality | Good |
| Color | white |
| Odor | No odor |
| Shakability | good |
| Density | 0.010 |
| Hardness | 9.62 |
| Babble size | 84 |

Procedure: Mineral oil was heated to ~60° C., followed by the addition of glycerol stearate, until fully dissolved. The mixture was cooled instantly to 30° C. using an ice bath. Cyclomethicone 5-NF was added with vigorous agitation at 30° C. The mixture was cooled to room temperature.

Foam quality surprisingly was good using GMS PEG 100 monostearate although it is more hydrophilic properties compared to glycerol monostearate solely. Density was low compared to glycerol monostearate alone.

Example 16

Heavy Mineral Oil, Cyclomethicone 5-NF and Sorbitan Ester Surfactants

A) Solid Span Surfactants

| Ingredients | 25 | 28 |
|---|---|---|
| Procedure | (I) Slow to 35-40° C. (II) Slow to RT | |
| Heavy Mineral Oil | 86.00 | 86.00 |
| Span 60 | 4.00 | |
| Span 40 | | 4.00 |
| Cyclomethicone 5-NF | 10.00 | 10.00 |
| Total | 100.00 | 100.00 |
| Propellant (A46 a mixture of propane, butane and isobutane) | 12.00 | 12.00 |
| RESULTS FOAM | | |
| Foam Quality | Fair | Fair |
| Color | White | White |
| Odor | No Odor | No Odor |
| Shakability | Good | Good |

Formulations with sorbitan ester surfactants alone did not produce foams of quality.

B) Other Solid Surfactants

| Ingredients | 24 | 26 | 27 |
|---|---|---|---|
| Procedure | (I) Slow to 35-40° C. (II) Slow to RT | | |
| Heavy Mineral Oil | 86.00 | 86.00 | 86.00 |
| steareth-2 | 4.00 | | |
| methyl glucose sesquistearate | | 4.00 | |
| sufhope SE D-1805 | | | 4.00 |
| Cyclomethicone 5-NF | 10.00 | 10.00 | 10.00 |
| Total | 100.00 | 100.00 | 100.00 |
| Propellant(propane + butane + isobutene) A46 | 12.00 | 12.00 | 12.00 |
| RESULTS FOAM | | | |
| Foam Quality | Fair | Fair | Fair |
| Color | White | White | White |
| Odor | No Odor | No Odor | No Odor |
| Shakability | Good | Good | Good |

Procedure for (24-27): Heavy mineral oil was heated to about 50-55° C. followed by the addition of Surfactant until fully dissolved. The mixture was cooled to about 35-40° C. Cyclomethicone was added with vigorous agitation and cooled to room temperature.

The formulations above demonstrate that not all solid surfactants are appropriate.

Section 3—Oils

Example 17

Ratios of Light and Heavy Mineral Oil

Following the results in example 18, studies were performed to investigate different ratios of light and heavy mineral oil role in formulation

| Ingredients | 08 | 09 | 010 | 011 |
|---|---|---|---|---|
| Procedure | Slow to 40° C. | Instant cooling to 30° C. | | |
| Light mineral oil | 86.00 | 86.00 | 43.00 | 28.50 |
| Heavy mineral oil | | | 43.00 | 57.50 |
| Glycerol monostearate | 4.00 | 4.00 | 4.00 | 4.00 |
| Cyclomethicone 5-NF | 10.00 | 10.00 | 10.00 | 10.00 |
| Total | 100.00 | 100.00 | 100.00 | 100.00 |
| Propellant | 8.00 | 8.00 | 8.00 | 8.00 |
| Results PFF | | | | |
| Viscosity 10 RPM | 85 | 1024 | 1758 | 1778 |

| Ingredients | 08 | 09 | 010 | 011 |
|---|---|---|---|---|
| Foam | | | | |
| Quality | Good | Excellent | Excellent | Excellent |
| Color | white | white | white | white |
| Odor | No odor | No odor | No odor | No odor |
| Shakability | good | Good | Good | Good |
| Density | 0.210 | 0.205 | 0.230 | 0.230 |
| Hardness | 11.50 | 16.50 | 15.46 | 14.93 |
| Greasiness | Low | Low | Medium | High |

Procedure 08: Mineral oil was heated to ~60 C, followed by the addition of glycerol monostearate until fully dissolved. The mixture was cooled slowly to 40-45° C. Cyclomethicone 5-NF was added with vigorous agitation at 40-45° C. The mixture was cooled to room temperature.

Procedure 09; 010; 011: Mineral oil was heated to ~60° C., followed by the addition of glycerol stearate until fully dissolved. The mixture was cooled rapidly to 30° C. using an ice bath. Cyclomethicone 5-NF was added with vigorous agitation at 30° C. The mixture was cooled to room temperature while stirring.

Foam quality: Light mineral oil using the slow cooling procedure, produced foam which was qualified as good compared to excellent in the fast cooling. Mixtures of the two produced high quality foam. Incorporation of light Mineral Oil improved foam quality.

These formulations were graded and placed on skin to determine impact on feeling. Scale was as follows: High—unpleasant greasy feeling; Medium—bearable medium greasy; Low—pleasant feeling. When light mineral oil was the major component, the foam was less greasy compared to foams in which heavy mineral oil was used in the high percentage.

Density—No major differences in density were observed. However, when using light solely or in combination, density is lower.

Viscosity—Interestingly when light mineral oil was the only oil used in the slow procedure, separation was detected in the PFF and its viscosity was extremely low. The presence of light mineral oil reduced the viscosity of the PFF compared to heavy mineral oil.

When light mineral oil was used in comparison to heavy mineral oil, the foam quality was high. However, the PFF demonstrated low viscosity and separation of oil and silicone components. When a combination of heavy and light was used in ratios 1:1 and 1:2. respectively, the viscosity increased and the foam demonstrated high quality and enhanced feeling.

Example 18

Comparison Between Heavy Mineral Oil and MCT Oil

| Ingredients | 18C | 20C | 31 |
|---|---|---|---|
| | (I) Rapid cooling to 40-45° C., (II) RT | (I) Rapid to 40-45° C. (II) Rapid to RT | (I) Rapid to 40-45° C. (II) Rapid to RT |
| Heavy Mineral Oil | 84.28 | | |
| MCT Oil | | 84.28 | |
| Octyldodecanol | | | 84.00 |
| Glycerol monostearate | 3.92 | 3.92 | 4.00 |
| Cyclomethicone 5-NF | 9.80 | 9.80 | 10.00 |
| Clindamycin Phosphate | 2.00 | 2.00 | 2.00 |
| Total | 100.00 | 100.00 | 100.00 |

| Ingredients | 18C | 20C | 31 |
|---|---|---|---|
| Propellant(propane + butane + isobutene) A46 | 12.00 | 12.00 | 12.00 |
| RESULTS PFF | | | |
| Viscosity (10 RPM) | 767.84 | 1095.77 | 146.97 |
| FOAM | | | |
| Foam quality | Good | Good- | Fairly Good |
| Color | White | White | White |
| Odor | No odor | No odor | No odor |
| Shakability | Good | Good | Good |
| Density | 0.103 | 0.085 | N/M |
| Collapse Time (36 C.-Sec.) | >300/FG | 100/F | N/M |
| Bubble Mean Size (Mm) | 89.00 | N/M | N/M |
| Bubbles Above 500 Mm (%) | 0.00 | N/M | N/M |

N/M = Not measured

Procedure for 18C—see example 1

Procedure for 20C—MCT oil was heated to about 50-55° C. followed by the addition of glycerol stearate until fully dissolved. The mixture was cooled rapidly to about 40-45° C. Cyclomethicone 5-NF was added with vigorous agitation and cooled rapidly to room temperature. API was added with stirring.

Procedure for 31: Octyldodecanol was heated to about 50-55° C. followed by the addition of glycerol stearate until fully dissolved. The mixture was cooled rapidly to about 40-45° C. Cyclomethicone 5-NF was added with vigorous agitation and cooled rapidly to room temperature. Clindamycin Phosphate was added with stirring.

Replacement of mineral oil by MCT oil does not significantly influence foam quality but substituting octyldodecanol does result in a foam quality reduction. Interestingly, collapse time with mineral oil is substantially longer.

Example 19

Heavy and Light Mineral Oil Mixture and Silicone Carrier with Solid Fatty Alcohol

| Ingredient name | 002 |
|---|---|
| Procedure | Rapid to 40-45° C. |
| Light Mineral oil | 25.00 |
| Heavy mineral oil | 54.00 |
| Glycerol monostearate | 6.50 |
| Cyclomethicone 5-NF | 10.00 |
| Myristyl Alcohol | 2.00 |
| Total: | 97.50 |
| Propellant AP-70 | 8.00 |

| Ingredient name | 002 |
|---|---|
| Results | |
| Foam Quality | Excellent |
| Color | White |
| Odor | No Odor |
| Shakability | Good |
| Collapse time | >180 sec/G* |
| FTC results | |
| Quality | Good |
| Color | White |
| Odor | No odor |
| Shakability | Good |
| Density [g/mL] | 0.079 |
| Collapse time at 36° C. (sec) | >180 |

Light mineral oil, heavy mineral oil and Myristyl Alcohol were mixed and heated to 60-65° C. followed by the addition of glycerol stearate until fully dissolved. The mixture was cooled rapidly to about 40-45° C. Cyclomethicone 5-NF was added with vigorous agitation and cooled rapidly to 5-10° C.

Mixed mineral oil plus silicone oil with added solid fatty alcohol provides excellent stable low density, shakable, breakable foam, which is capable of being subjected to four freeze-thaw (FTC) cycles. The carrier can be used to provide a homogenous suspension of API as well as dissolving oil soluble API's. As shown above, the carrier produces a stable, breakable foam which does not collapse after more than 3 minutes in the absence of applied mechanical shear force.

Example 20

Oil: PPG-15 Stearyl Ether, Octyldododecanol and Silicone Carrier Using the Rapid Cooling Procedure Ex 22 PART A)

| Ingredient name | 001P % w/w | 002P % w/w | 003P % w/w | 004P % w/w | 005P % w/w | 006P % w/w | 007P % w/w |
|---|---|---|---|---|---|---|---|
| PPG-15 Stearyl Ether | | | | 15.00 | 15.00 | 15.00 | 15.00 |
| Octyldodecanol | | | | 6.00 | 4.00 | 4.00 | 6.00 |
| Light mineral oil | 25.00 | 25.00 | 25.00 | 23.00 | 22.00 | 22.50 | 25.50 |
| Heavy mineral oil | 50.90 | 50.90 | 51.90 | 31.40 | 38.50 | 38.50 | 31.40 |
| Glycerol monostearate | 4.00 | 4.00 | 4.00 | 10.00 | 6.00 | 4.00 | 8.00 |
| Myristyl alcohol | | | | | | 2.40 | 2.40 |

-continued

| Ingredient name | 001P % w/w | 002P % w/w | 003P % w/w | 004P % w/w | 005P % w/w | 006P % w/w | 007P % w/w |
|---|---|---|---|---|---|---|---|
| Paraffin 51-53 | | | | | | 1.50 | |
| Cetostearyl alcohol | | | | 2.50 | | | 2.00 |
| Stearyl alcohol | 1.00 | 1.00 | | | | | |
| Cyclomethicone 5-NF | 10.00 | 10.00 | 10.00 | 3.00 | 3.00 | 3.00 | 3.00 |
| Triethanol amine | 0.10 | 0.10 | 0.10 | 0.10 | 0.10 | 0.10 | 0.10 |
| PPG 15 stearyl ether | 8.9604 | | | | | | |
| Capric caprylic triglyceride | | 8.9604 | 8.9604 | 8.9604 | 8.9604 | 8.9604 | 8.9604 |
| Butyleated hydroxytoluen | 0.0396 | 0.0396 | 0.0396 | 0.0396 | 0.0396 | 0.0396 | 0.0396 |
| Total: | 100.00 | 100.00 | 100.00 | 100.00 | 100.00 | 100.00 | 100.00 |
| Propellant AP-70 | 8.00 | 8.00 | 8.00 | 8.00 | 8.00 | 8.00 | 8.00 |
| Foam appearance of placebo (without API) | FG | FG | FG | Excellent | Good | Good- | Excellent |
| Shakability of placebo (without API) | Good | Good | Good | Not shakable but flowable | Good | Good | Moderate |

Surprisingly it appears that the presence of about 9% Capric/caprylic triglyceride (MCT oil) reduces the foam quality to fairly good and it may be that a small amount of Triethanolamine also has a negative impact on foam quality. Addition of PPG-15 stearyl ether with octyldodecanol into the formulation appears to counteract this capric caprylic triglyceride effect. It may be that PPG-15 Stearyl Ether or Octyldodecanol are effective alone.

Further results for formulations 005 and 007 in which the API is present are provided in the tables below in Parts C TO F:

Ex 20 PART B)

| Ingredient name | 005 % w/w | 007 % w/w |
|---|---|---|
| PPG-15 Stearyl Ether | 15.00 | 15.00 |
| Octyldodecanol | 4.00 | 6.00 |
| Light mineral oil | 22.00 | 25.50 |

-continued

| Ingredient name | 005 % w/w | 007 % w/w |
|---|---|---|
| Heavy mineral oil | 38.50 | 31.40 |
| Glycerol monostearate | 6.00 | 8.00 |
| Myristyl alcohol | 2.40 | |
| Cetostearyl alcohol | | 2.00 |
| Stearyl alcohol | | |
| Cyclomethicone 5-NF | 3.00 | 3.00 |
| Triethanol amine | 0.10 | 0.10 |
| Capric caprylic triglyceride | 8.9595 | 8.9595 |
| Butyleated hydroxytoluene | 0.0396 | 0.0396 |
| Calcitriol | 0.0009 | 0.0009 |
| Total: | 100.00 | 100.00 |
| Propellant AP-70 | 8.00 | 8.00 |

Ex 20 PART C) Foam Product (Pressurized Formulation)

| Formulation | Shakability | Appearance Quality* | Appearance Color | Appearance Odor | Density [g/mL] | Collapse time at 36° C. [sec] | Hardness [g] | Product homogeneous and redispersibile after shaking (when viewed in pressurized glass bottle) |
|---|---|---|---|---|---|---|---|---|
| 005 | 1 | E | 1 | 2 | 0.104 | 180 | 13.43 | Yes |
| 007 | 2 | E | 1 | 2 | 0.105 | >300 | 16.50 | Yes |

*After at least 24 hours following manufacture

Ex 20 PART D) Short Term Physical Stability, Test Results

| Formulation | Shakability | | | Appearance Quality (scoring) | | | Appearance Color (scoring) | | | Appearance Odor (scoring) | | | Density (g/mL) | | |
|---|---|---|---|---|---|---|---|---|---|---|---|---|---|---|---|
| | T-0 | FTC | 3 weeks, 40° C. | T-0 | FTC | 4 weeks, 40° C. | T-0 | FTC | 3 weeks, 40° C. | T-0 | FTC | 3 weeks, 40° C. | T-0 | FTC | 3 weeks, 40° C. |
| 005 | 1 | 2 | 2 | E | G | FG | 1 | 1 | 1 | 2 | 2 | 2 | 0.104 | 0.111 | 0.112 |
| 007 | 2 | 2 | 2 | E | G | G | 1 | 1 | 1 | 2 | 2 | 2 | 0.105 | 0.112 | 0.112 |

Ex 20 PART E) Short Term Physical Stability, Test Results—Continued

|  | Collapse time (sec) | | Product homogeneous and redispersible after shaking(when viewed in pressurized glass bottle) | | Corrosion & deterioration |
|---|---|---|---|---|---|
| Formulation | T-0 | 3 weeks, 40° C. | T-0 | 3 wk | 3 weeks, 40° C. |
| 005 | 180 | 180 | Yes | Yes | None observed |
| 007 | >300 | >300 | Yes | Yes | None observed |

Ex 20 PART F) The codes for foam color, foam odor and shakability are as provided below:

|  | Score |
|---|---|
| Foam Color | |
| White to faint yellow (acceptable) | 1 |
| Darker than yellow (not acceptable) | 0 |
| Foam Odor | |
| No odor | 2 |
| Very faint -Typical odor | 1 |
| Noticeable odor | 0 |
| Shakability | |
| Good shakability (acceptable) | 2 |
| Moderate shakability (acceptable) | 1 |
| Not shakable (not acceptable) | 0 |

Ex 20 PART G) Formulations 5, 6, 7 are preferred and show how relatively small changes in the composition can substantially affect the foam produced. The data also demonstrate the stability of the formulations and the ability of the formulations to withstand strenuous environmental conditions.

A batch of formulation 007 was prepared. Prior to the cooling step the batch was divided into two. One part was subjected to fast cooling by immersing the container into an ice bath with stirring to reach room temperature whilst another part was merely left to cool in the room to room temperature with stirring without any external bath.

| Cf Section 3 below | 007 | 007 |
|---|---|---|
| Procedure | Slow cooling to 25-30° C. | Rapid cooling to 25-30° C. |
| Ingredient name | % w/w | % w/w |
| PPG-15 Stearyl Ether | 15.00 | 15.00 |
| Octyldodecanol | 6.00 | 6.00 |
| Light mineral oil | 25.50 | 25.50 |
| Heavy mineral oil | 31.40 | 31.40 |
| Glycerol monostearate | 8.00 | 8.00 |
| Cetostearyl alcohol | 2.00 | 2.00 |
| Cyclomethicone 5-NF | 3.00 | 3.00 |
| Triethanol amine | 0.10 | 0.10 |
| Stock Solution (as per Example 12) | 9.00 | 9.00 |
| Total: | 100.00 | 100.00 |
| Propellant AP-70 | 8.00 | 8.00 |
| Results | | |
| PFF (before addition of propellant) | | |
| Appearance | Rich Milky Cream | Cloudy Ointment |
| Feel | Creamy | Oily Ointment |
| Foam | | |
| Quality | E | E |
| Color | white | white |
| Odor | no odor | no odor |
| Shakability | Good | Good |
| Density [g/mL)] | 0.110 | 0.105 |
| Collapse time at 36 C. [sec] | >180/G | >180/G |

Whilst the PFF was externally visually different (FIG. 1) and also displayed a different feel there was no apparent difference in the physical properties of the resultant foam after addition of propellant and release of the formulations from a sealed canister. Unexpectedly, the slow cooled formulation provided a cosmetically elegant creamy feel whilst the fast cooled formulation was more oily and ointment like in sensation. On a microscopic level whilst both PFF's contained some bubble or vesicle like structures the slow cooled formulation displayed a higher number of such bodies. These bodies had within them a bubble like structure.

Section 4—Miscellaneous

Example 21

Rate of Cooling Experiments

A 100 g batch of formulation was prepared in each case according to the cooling methods described herein. It is noted that larger batch sizes will require a longer time duration for cooling using the same size and quantity ice bath and, accordingly, the rate of cooling will be slower. The rate of cooling can be increased by using a supercooled mixture of water, ice and salt or acid. Such mixtures can readily reach temperatures of minus 10° C. Care is taken to ensure that the formulation is stirred rapidly and the temperature does not fall below room temperature. Thus, by simply having a larger temperature gradient rapid cooling can be accelerated. Lower temperatures can be achieved by using a colder substance such as a slurry of dry ice provided their use is very carefully controlled such that the temperature does not fall below room temperature and that freeing is not induced. Other means of improving cooling, as known in the art can be used such a a cooling jacket through which is pumped cold water.

Part A—Rapid

The formulation 043 below was prepared and subjected to rapid cooling as follows:

| Ingredients | 043-Rapid % w/w |
|---|---|
| Heavy Mineral Oil | 86.00 |
| Glycerol Monostearate | 4.00 |
| Cyclomethicone | 10.00 |
| Control: | 100.00 |
| Propellant 1681 | 8.00 |

Manufacturing Procedure (Rapid Cooling Protocol):

Step 1: Mixing of Oily Ingredients and Surfactant

Heat up the Heavy mineral oil to 60-65° C.

Add Glycerol monostearate under mixing by homogenizer for 15-20 min.

Mix till completely dissolution. Allow to reach ~65° C.

Step 2: Cooling of PFF

Cool down the PFF from Step 1 to 33-35° C. by plunging the container into an ice bath while stirring.

The time it took for the composition to cool to certain temperatures was measured:

Temperature drop from 65° C. to 55° C.: 1 min 16 sec (7.9 degrees/minute);

Temperature drop from 55° C. to 45° C.: 1 min 30 sec (6.7 degrees/minute);

Temperature drop from 45° C. to 35° C.: 2 min 20 sec (2.2 degrees/minute);

Step 3: Add Cyclomethicone by Mixing.

Continue Cooling down to the room temperature with stirring using the ice bath.

Temperature drop from 35° C. to 25° C.: 2 min 30 sec (2.2 degrees/minute);

Cool to room temperature Mix well the whole preparation for 15-20 min.

The formulation 043 below was prepared and subjected to slow cooling as follows:

Part B

A second batch of composition (044-Slow) was prepared and cooled according to the slow cooling procedure described herein.

| Ingredients | 044-Slow % w/w |
| --- | --- |
| Heavy Mineral Oil | 86.00 |
| Glycerol Monostearate | 4.00 |
| Cyclomethicone | 10.00 |
| Control: | 100.00 |
| Propellant 1681 | 8.00 |

Manufacturing Procedure (Slow Cooling Protocol):

Step 1: Mixing of Oily Ingredients and Surfactant

Heat up the Heavy mineral oil to 60-65° C.

Add Glycerol monostearate under mixing by homogenizer for 15-20 min.

Mix until complete dissolution. Allow to reach ~65° C.

Step 2: Cooling of PFF

Cool down the PFF from Step 1 to 33-35° C. by standing on air (i.e., room temperature) by stirring.

The time it took for the composition to cool to certain temperatures was measured: Temperature drop from 65° C. to 55° C.: 2 min 30 sec (2.2 degrees/minute);

Temperature drop from 55° C. to 45° C.: 5 min 30 sec (1.8 degrees/minute);

Temperature drop from 45° C. to 35° C.: 8 min 30 sec (1.2 degrees/minute);

Step 3: Add Cyclomethicone by Mixing.

Continue cooling down to room temperature with stirring using the ice bath.

Temperature drop from 35° C. to 25° C.: 26 min (0.4 degrees/minute);

Cool to room temperature. Mix well the whole preparation for 15-20 min.

Part C—Super fast cooling by insertion into alcohol—water circulating bath at –10° C.

A batch of composition (046-Super Fast) was prepared and cooled according to the super fast cooling procedure described herein.

| Ingredients | 046 Super Fast % w/w |
| --- | --- |
| Heavy Mineral Oil | 86.00 |
| Glycerol monostearate | 4.00 |
| Cyclomethicone | 10.00 |
| Control: | 100.00 |
| Propellant 1681 | 8.00 |

Manufacturing Procedure (Super Fast Cooling Protocol):

Step 1: Mixing of Oily Ingredients and Surfactant

Heat up the Heavy mineral oil to 65° C. Allow to reach ~65° C.

Add glycerol monostearate under mixing by homogenizer for 15-20 min.

Mix till completely dissolution. Allow to reach ~65° C.

Step 2: Cooling of PFF

Cool down the PFF from Step 1 to 33-35° C. by plunging the container into an Lauda RE206 alcohol-water bath at (–10° C.) by plunging the container into an alcohol-water circulating bath at –10° C. while stirring.

The time it took for the composition to cool to certain temperatures was measured:

Temperature drop from 65° C. to 55° C.: 1 min (10 degrees/minute)

Temperature drop from 55° C. to 45° C.: 1 min (10 degrees/minute)

Temperature drop from 45° C. to 35° C.: 1 min 30 sec (6.7 degrees/minute)

Add Cyclomethicone by mixing.

Continue cooling down to the room temperature (23° C.) with stirring using the alcohol water bath.

Temperature drop from 35° C. to 25° C. (RT): 2 min 30 sec (4 degrees/minute)

Cool to room temperature. Mix well the whole preparation for 15-20 min.

Conclusions:

All formulations -043 and -044 and -046 were tested for foam quality. Rapid and super rapid produced good quality foam whilst slow cooling produce foam of a lower quality, namely fairly good. These experiments clearly show that the foam quality of formulations prepared by fast cooling and extremely fast cooling methods were better than that produced by the slow cooling method.

The total time to cool from 65° C. to room temperature for rapid cooling with a regular ice bath took 7 minutes 36 seconds and was approximately almost six fold faster overall when compared to slow cooling, which took 42 minutes 30 seconds. The initial temperature drop to 55° C. took less than half the time than that for slow cooling. Each stage thereafter took progressively longer for slow cooling. When a super cool bath was used the cooling rate was reduced by about 25% to six minutes when compared to the rapid procedure.

Section 5—Rapid Collapse Prior Art Example

Example 24

US 2005/0287081 provides examples of high silicone lipophilic formulations with liquid surfactant and beeswax. The formulation of Example 1 of the "081" application set out below was made in duplicate as described below.

All ingredients are weighed in a vessel and it is heated to 70-75° C., and mixed well until uniform. It is then cooled to ambient and pressurized in an aerosol can with Hydrofluorocarbon in the ratio: Base: 85%, Propellant: 15%.

| Ingredient | % w/w |
|---|---|
| Caprylic/Capric Triglyceride | 20.00 |
| Mineral Oil | 8.00 |
| Cyclomethicone 5-NF | 31.25 |
| Sorbitan Oleate | 5.00 |
| Polyoxyl 40 Hydrogenated Castor Oil | 4.00 |
| Petrolatum | 30.00 |
| Beeswax | 0.75 |
| Hydrogenated Castor Oil | 1.00 |

The foam quality for the formulation prepared accordingly to the Examples of US 2005/0287081, in both cases with propellant AP70, was fair (which is not considered acceptable for pharmaceutical formulations). Notably, the foam started to collapse almost immediately upon dispensing, and fully collapsed after approximately 10 seconds. The formulation was prepared again, with a different propellant (Dymel), with very similar results.

Discussion

Surprisingly single phase mixture of a surfactant-glycerol monostearate and oil were capable of producing high foam quality. glycerol monostearate and other fatty acid monoesters are not efficient emulsifiers as sited from Handbook of pharmaceutical excipients $5^{th}$ edition. In some embodiments, when glycerol monostearate was replaced by other surfactants, foam quality was reduced, emphasizing the effect of this unique surfactant.

As described herein foamable carriers containing glycerol monosterate, which is highly soluble in mineral oil, produced foam of high quality. Interestingly, foamable carriers containing glycerol palmitostearate, which is not soluble in oil also produced high quality foam. Indeed mixing mineral oil and glyceryl palmitostearate formed two phases in comparison to a single phase GMS/oil system. Nevertheless, glycerol palmitostearate is an esterification product of stearic and palmitic acids. Therefore it may be assumed that partial solubility may be demonstrated. Moreover, without being bound to any theory, it may be assumed that addition of cyclomethicone to a compositions containing glycerol palmitostearate may increase the solubility of glycerol palmitostearate in oil. This is in concordance with the common polarity index of both emollients: mineral oil approximately 43.7 mN/m and cyclomethicone approximately 20 mN/m. Mixing of both increases the polar environment required for enhanced solubility of palmitostearate.

The addition of a silicone to the oil and glycerol monostearate mixture—whilst having defoaming and destabilizing properties—was able to lower surface tension to provide the foam with an improved and elegant feel and a drying effect.

Surprisingly cyclomethicone can act to improve foam quality at certain ratios with oil and yet at other ratios it acts to destroy the foam structure. Unexpectedly, when cyclomethicone was introduced into formulations with some of the other surfactants (other than glycerol monostearate) it slightly improved foam quality compared to foam produced from the same formulations without cyclomethicone.

Foam quality depends on spatial structure of silicones: cyclic and highly substituted linear silicones create a stearic hindrance and may not penetrate to any significant or substantial degree into the stable mineral oil/Glycerol monostearate structure.

Apparently, in order to produce foam of quality, the selection of surfactant is important and the ratio between Glycerol monostearate and Cyclomethicone 5-NF in formulation can be approximately in the range of 1:1 to 1:4 respectively.

The manufacturing procedure is highly significant. Introduction of a rapid cooling step improved foam quality when compared to the foam of the same formulation produced using slow cooling. Thus, rapid cooling of oil/silicone single phase formulations unexpectedly results in the production of high quality foam. It was noted that rapid cooling of mineral oil/silicone/Glycerol monostearate mixture from 60° C. to minimum 30° C. significantly and visibly improved foam quality. Moreover a continuum of cooling step following the addition of silicones of stearic hindrance improves foam quality. Changes (visual) in the pre-foam formulation appearance and in its viscosity were surprisingly noted depending on whether fast or slow cooling was used.

Not only was fast cooling preferred but addition of the silicone is surprisingly preferred the closer the temperature is to room temperature. In other word Silicone is best added after the rapid cooling is completed.

Mixtures of oils were unexpectedly better. Also mixtures were less susceptible to the destabilizing effects of silicones. Similarly formulations with many ingredients were less susceptible to the effects of silicones than formulations with few ingredients—perhaps without being bound by any theory there are more options available to the silicones other than say mineral oil/surfactant arrangements.

Section 6—Prophetic Examples

Example 25

Prophetic a) Foamable Oil and Silicone Compositions, Containing a Steroid Drug

The following steroids can be included in carriers, compositions and foams: betamethasone valerate 0.12%, clobetasol propionate 0.05%, betamethasone dipropionate 0.05%, fluocinolone acetonide 0.025%, hydrocortisone acetate 0.5% and hydrocortisone butyrate 0.1%.

b) Foamable Oil and Silicone Compositions, Containing a Vitamin and a Steroid Drug Additionally, one or more of the following vitamins can be included in the carriers, compositions and foams: vitamin C (ascorbic acid) between 0.1 and 5% say, 0.1% 1%, 2% 3%, 4%, or 5%; vitamin C (magnesium ascorbyl phosphate) 3%, retinol 1%, retinoic acid 0.1%, niacinamide 2% and tocopherol 1% and Vitamin K. between 0.1 and 2% say, 0.1% or 1% or 2%.

Example 18

Prophetic Foamable Vitamin Compositions with an Additional Therapeutic Agent

Foamable vitamin compositions at either say 1%, 2%, 3%, 4%, or 5%, by weight of composition are made up with an active agent and added to any of the compositions illustrated in Examples 1-12 and 16 below with or without the active agents listed in the Examples wherein the percentage amount of solvent is reduced by an approximately equivalent amount by weight in the composition.

Example 26

Prophetic Foamable Therapeutic Agent Compositions

More particularly exemplary concentrations of additional therapeutic agents in foamable compositions are set out in the table below. Each active agent is added into, for example, any of the carriers listed in any of Examples 1-12 above and 16 below in a therapeutically effective concentration and amount with or without the active agents listed in the Examples. The methodology of addition is well known to those of the art. The composition is adjusted in each case so that it is made up to 100% w/w as appropriate by solvent.

Exemplary Concentrations of Examples of Active Agents

| Additional therapeutic agent | Exemplary Concentration | Exemplary Use |
|---|---|---|
| Hydrocortisone acetate | 1% | Steroid responsive inflammation and psoriasis or atopic dermatitis |
| Betamethasone valerate | 0.1% | |
| Clobetasol propionate | 0.05% | |
| Acyclovir | 5% | Viral infection, herpes |
| Ciclopirox | 1% | Fungal infection, seborrhea, dandruff, |
| Clindamycin | 2% | Bacterial infection, acne, rosacea, |
| Azelaic acid | 15% | Acne, rosacea, pigmentation disorder and various dermatoses |
| Metronidazol | 0.25%-2% | Rosacea, bacterial infections and parasite infestations |
| Diclofenac | 1% | Osteoarthritis, joint pain |
| Tacrolimus | 0.2% | Atopic dermatitis, eczema and inflammation |
| Benzoyl peroxide | 1%-10% | Acne |
| Alpha-hydroxy acids | 1%-20% | Aging, wrinkles |
| Salicylic acid | 1%-10% | Acne |
| Hydroquinone | 1%-10% | Pigmentation disorders |
| Caffeine | 1%-10% | Anti Cellulite |
| Coenzyme Q 10 | 0.1%-10% | Aging, pigmentation |
| Clotrimazole | 1% | Fungal infection |
| Lidocaine base | 2% | Local anesthetic |
| Terbinafine HCL | 1% | Fungal infection |
| Gentamycin | 0.1% | Bacterial skin infections, burns or ulcers |
| Dexpanthenol | 5% | Wounds, ulcers, minor skin infections |
| Urea | 5-10% | Emollient and keratolytic Atopic dermatitis, eczema, ichthyosis and hyperkeratotic skin disorders |
| Ammonium lactate | 12%-17.5% | Dry scaly conditions of the skin including ichthyosis |
| Povidone-iodine | 10% | Antimicrobial - antiseptic |
| Calcitriol | ~0.005% | Psoriasis |
| Calcipotriol | ~0.005% | Psoriasis |
| Imiquimod | 5% | Treatment of external genital and perianal warts, superficial basal cell carcinomas and actinic keratoses |
| Estradiol | 0.005% | Treatment of vaginal atrophy caused by menopause |
| Minocycline Hydrochloride | 1% | Treatment of acne |
| Doxycycline Monohydrate | 1% | Treatment of acne |
| Doxycycline Hyclate | 1% | Treatment of acne |

The above examples represent different drug classes and it is to be understood that other drugs belonging to each of the classes represented above may be included and used in the compositions in a safe and effective amount.

Example 27

Prophetic Foamable Compositions Comprising Microsponges

A microsponge is added into, for example, any of the carriers listed in any of Examples 1-11 above. The microsponges are loaded with active agents in a therapeutically effective concentration and amount and the microsponges are incorporated into one of the said carriers. The methodology of addition is known to those of the art. The composition is adjusted in each case so that it is made up to 100% w/was appropriate by solvent. Care should be taken in selecting and preparing the formulation such that the microsponges are distributed substantially homogenously and so that any aggregation of microsponges is minimized such that they do not block the canister valve and thereby prevent release of foam.

Example 27A

Prophetic Hydrophobic Solvent Foamable Formulation Comprising Microsponges Loaded with Active Agent

| Ingredients | % w/w | % w/w |
|---|---|---|
| Drug Microsponge ® | 10 | 10 |
| Heavy Mineral Oil | To 100 | |
| Light Mineral Oil | | To 100 |
| Volatile Silicone* | 1-25 | 1-25 |
| Glycerol monostearate | 1-5 | 1-5 |
| Propellant | 12.00 | 12.00 |

*volatile silicone can be for example Cyclomethicone.

This prophetic formulation can be adapted for a high range of hydrophobic solvent content of up to about 95%.

The amount of microsponges may be varied from about 1% to about 25% of the formulation by increasing or decreasing the amount of the hydrophobic solvent.

Any active agent suitable for loading in microsponges may be used. Non-limiting examples are benzyl peroxide, tretinoin, hydroquinone and the like or any of the active agents described in Examples 1 to 11 above.

In an embodiment the microsponges are loaded with one or more vitamins or with one or more flavonoids or combinations thereof.

The liquefied or gas propellant can be added at a concentration of about 3% to about 35%, for example in a ratio of carrier composition to propellant of at least about 100:3, or about 100:3 to about 100:35.

It is appreciated that certain features, which are, for clarity, described in the context of separate embodiments, may also be provided in combination in a single embodiment. Conversely, various features, which are, for brevity, described in the context of a single embodiment, may also be provided separately or in any suitable subcombination. Although the invention has been described in conjunction with specific embodiments thereof, it is evident that many alternatives, modifications and variations will be apparent to those skilled in the art.

What is claimed is:

1. A waterless foamable pharmaceutical composition, comprising a foamable carrier and at least one liquefied or compressed gas propellant, wherein the foamable carrier comprises:
    a) about 60% to about 95% by weight of the foamable carrier of at least one liquid oil selected from the group comprising a mineral oil, a MCT oil, a liquid paraffin, a vegetable oil, an essential oil, an organic oil, a lipid, or a mixture of two or more thereof comprising about 60-90% mineral oil;
    b) about 0.5% to about 15% by weight of the foamable carrier of a silicone; and
    c) about 0.01% to about 25% by weight of the foamable carrier of at least one foam stabilizing agent comprising glyceryl monostearate;
    wherein the foamable carrier is a single phase;
    wherein the foam stabilizing agent optionally comprises at least one foam adjuvant;
    wherein the silicone is selected from the group consisting of a siloxane compound having 4-6 Si—O groups in its backbone, a cyclomethicone, a cyclotetrasiloxane, a cyclopentasiloxane, a cyclohexasiloxane, a phenyl trimethicone, a stearyl dimethicone, a cetyl dimethicone, a caprylyl methicone, a PEG/PPG 18/18 dimethicone, a dimethiconol, and a mixture of any two or more thereof;
    wherein the composition is essentially free of water;
    wherein the ratio of the foamable carrier to the propellant is 100:3 to 100:35;
    wherein the resultant foam does not collapse immediately upon release and is breakable on mechanical shear;
    wherein the waterless foamable pharmaceutical composition comprises a minocycline or a doxycycline or both; and
    wherein the minocycline or the doxycycline is stable for at least 3 weeks at 25° C. in the waterless foamable pharmaceutical composition.

2. The waterless foamable pharmaceutical composition of claim 1, wherein the oil is a mixture of heavy mineral oil and light mineral oil having a weight ratio from about 1:5 to about 25:1.

3. The waterless foamable pharmaceutical composition of claim 1, further comprising an emollient selected from the group consisting of cocoglycerides, PPG 15 stearyl alcohol, octyldodecanol, isopropyl myristate, diisopropyl adipate, cetearyl octanoate isohexadecanol, diisopropyl adipate, and a mixture of any two or more thereof.

4. The waterless foamable pharmaceutical composition of claim 1, further comprising a solid wax or solid oil selected from the group consisting of a solid paraffin, a hydrogenated oil, a hydrogenated emollient, palmitic acid, stearic acid, arachidic acid, behenic acid, and a mixture of any two or more thereof.

5. The waterless foamable pharmaceutical composition of claim 1, wherein the foam adjuvant comprises a fatty alcohol and a fatty acid.

6. The waterless foamable pharmaceutical composition of claim 1, wherein the foam stabilizing agent is in combination with a foam adjuvant selected from the group consisting of stearyl alcohol, cetyl alcohol, cetostearyl alcohol, myristyl alcohol, palmitoleyl alcohol, arachidyl alcohol, benhyl alcohol, and a mixture of any two or more thereof.

7. The waterless foamable pharmaceutical composition of claim 1, wherein the foam stabilizing agent is in combination with a foam adjuvant, wherein said foam adjuvant comprises oleyl alcohol.

8. The waterless foamable pharmaceutical composition of claim 1, wherein the weight ratio of foam stabilizing agent to silicone ranges from about 1:1 to about 1:4.

9. The waterless foamable pharmaceutical composition of claim 1, comprising by weight of the foamable carrier:
    a) about 60-90% mineral oil;
    b) about 1-15% of a silicone, where the silicone is selected from the group consisting of a cyclomethicone, a cyclohexasiloxane, a cyclopentasiloxane, a cyclytetrasiloxane, a dimethiconol, a phenyl trimethicone, a stearyl dimethicone and a mixture of any two or more thereof;
    c) about 1-8% glycerol monostearate; and
    d) about 1-8% myristyl alcohol or cetostearyl alcohol.

10. A waterless foamable pharmaceutical composition according to claim 1, further comprising an active agent in addition to a minocycline and or a doxycycline.

11. The waterless foamable pharmaceutical composition according to claim 10, wherein the active agent is selected from the group consisting of active herbal extracts, acaricides, age spot removing agents, keratose removing agents, allergen, analgesics, local anesthetics, antiacne agents, antiallergic agents, antiaging agents, antibacterials, antibiotic agents, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents, antiseborrheic agents, antiseptic, antiswelling agents, antiviral agents, anti-yeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, scabicides, self tanning agents, skin whitening agents, vasoconstrictors, vasodilators, vitamin A, vitamin A derivatives, vitamin B, vitamin B derivatives, vitamin C, vitamin C derivatives, vitamin D, vitamin D derivatives, vitamin E, vitamin E derivatives, vitamin K, vitamin K derivatives wound healing agents, wart removers, and a mixture of any two or more thereof.

12. The waterless foamable pharmaceutical composition according to claim 10, wherein the additional active agent is selected from the group consisting of acyclovir, azaleic acid, clindamycin phosphate, pimicrolimus, diclofenac potassium, calcipotriol, calcitriol, vitamin A acetate, betamethasone 17-valerate, alpha tocopherol, imiquimod, ciclopiroxolamine, and a mixture of any two or more thereof.

13. A method for treating or ameliorating a disorder comprising administering to a target site a pharmaceutically effective amount of the waterless foamable pharmaceutical composition according to claim 1, wherein the target site is selected from the group consisting of the skin, a body cavity, a mucosal surface, the nose, the mouth, the eye, the ear canal, the respiratory system, the vagina, and the rectum.

14. A method according to claim 13, wherein the waterless foamable pharmaceutical composition comprises at least one additional active agent.

15. The waterless foamable pharmaceutical composition according to claim 1, wherein the resultant foam displays all of the following characteristics:
   a. does not collapse immediately upon release;
   b. is breakable on mechanical shear;
   c. has a viscosity below about 13,000 cps;
   d. has an average bubble size below 200 microns;
   e. has a hardness between about 5 to about 35;
   f has a collapse time in excess of about 180 seconds; and
   g. has a density below about 0.2g/ml.

16. The waterless foamable pharmaceutical composition according to claim 1, further comprising up to 5% or about 5% by weight of at least one polymeric agent alone or in combination with a foam adjuvant.

17. The waterless foamable pharmaceutical composition according to claim 10, wherein the foamable carrier including the active agent is a homogenous suspension.

18. A method for preparing a single phase waterless foamable pharmaceutical composition according to claim 1, the method comprising the steps of either:
   (a) combining the at least one liquid oil with the at least one foam stabilizing agent at a temperature of at least 50° C. or about 50° C.;
   (b) rapidly cooling the combination of one liquid oil and at least one foam stabilizing agent to less than 40° C.;
   (c) adding the silicone and the minocycline or the doxycycline or both to the cooled combination to make a prefoam formulation; and
   (d) combining the prefoam formulation with a compressed gas propellant in a weight ratio of 100:3 to 100:35 to form the waterless foamable pharmaceutical composition;

or (i) preparing a prefoam formulation by combining at a temperature of at least 50° C. or about 50° C.:
     the at least one liquid oil;
     the silicone; and
     the at least one foam stabilizing agent;
   (ii) rapidly cooling the prefoam formulation to less than 40° C.;
   (iii) adding the minocycline or the doxycycline or both to the prefoam formulation; and
   (iv) combining the prefoam formulation with a compressed gas propellant in a weight ratio of 100:3 to 100:35 to form the waterless foamble pharmaceutical composition.

19. The method of claim 18, wherein the cooling step is carried out by placing the combination of one liquid oil and at least one foam stabilizing agent in an ice bath, or in an alcohol water bath, or in a water bath or jacket.

20. The method of claim 18, wherein the combination of one liquid oil and at least one foam stabilizing agent is cooled at a rate of at least 5 degrees/minute or about 5 degrees/minute.

21. The method of claim 18, wherein the combination of one liquid oil and at least one foam stabilizing agent is cooled to a temperature of at least 25° C. or about 25° C.

22. The method of claim 18, wherein the foam stabilizing agent is a monoglyceride, diglyceride, or triglyceride, or a mixture of any two or more thereof, wherein the side chain of the monoglyceride, diglyceride, or triglyceride is a saturated hydrocarbon.

23. The method of claim 18, wherein the foam stabilizing agent is glycerol monostearate and glycerol palmitostearate.

\* \* \* \* \*